US009809651B2

(12) United States Patent
Govindappa et al.

(10) Patent No.: US 9,809,651 B2
(45) Date of Patent: Nov. 7, 2017

(54) METHOD OF TREATING CANCER WITH AN EGFR TARGETED IMMUNOMODULATORY FUSION PROTEIN

(71) Applicant: BIOCON LIMITED, Bangalore (IN)

(72) Inventors: Nagaraj Govindappa, Karnataka (IN); Kedarnath Sastry, Karnataka (IN); Maria Melina Soares, Karnatake (IN)

(73) Assignee: BIOCON LIMITED (IN)

( * ) Notice: Subject to any disclaimer, the term of this patent is extended or adjusted under 35 U.S.C. 154(b) by 0 days.

(21) Appl. No.: 15/047,062

(22) Filed: Feb. 18, 2016

(65) Prior Publication Data
US 2016/0168260 A1 Jun. 16, 2016

Related U.S. Application Data

(60) Continuation of application No. 14/458,674, filed on Aug. 13, 2014, which is a division of application No. 13/779,409, filed on Mar. 13, 2013, now Pat. No. 8,815,247.

(30) Foreign Application Priority Data

Apr. 30, 2012 (IN) ............ 1689/CHE/2012
Apr. 30, 2012 (IN) ............ 1690/CHE/2012

(51) Int. Cl.
C07K 16/28 (2006.01)
A61K 38/10 (2006.01)
A61K 38/17 (2006.01)
A61K 39/395 (2006.01)
C07K 14/495 (2006.01)
C07K 14/71 (2006.01)
C07K 14/00 (2006.01)
C07K 14/65 (2006.01)
C07K 14/705 (2006.01)
C07K 16/32 (2006.01)
G01N 33/68 (2006.01)
A61K 45/06 (2006.01)
C07K 7/08 (2006.01)
C07K 16/30 (2006.01)
A61K 39/00 (2006.01)
A61K 38/00 (2006.01)

(52) U.S. Cl.
CPC .......... C07K 16/2818 (2013.01); A61K 38/10 (2013.01); A61K 38/179 (2013.01); A61K 39/39558 (2013.01); A61K 45/06 (2013.01); C07K 7/08 (2013.01); C07K 14/00 (2013.01); C07K 14/495 (2013.01); C07K 14/65 (2013.01); C07K 14/70532 (2013.01); C07K 14/70596 (2013.01); C07K 14/71 (2013.01); C07K 16/2863 (2013.01); C07K 16/2866 (2013.01); C07K 16/2878 (2013.01); C07K 16/2887 (2013.01); C07K 16/30 (2013.01); C07K 16/32 (2013.01); G01N 33/6854 (2013.01); A61K 38/00 (2013.01); A61K 2039/505 (2013.01); C07K 2317/14 (2013.01); C07K 2317/24 (2013.01); C07K 2317/31 (2013.01); C07K 2317/51 (2013.01); C07K 2317/515 (2013.01); C07K 2317/732 (2013.01); C07K 2319/00 (2013.01); C07K 2319/02 (2013.01); C07K 2319/33 (2013.01)

(58) Field of Classification Search
None
See application file for complete search history.

(56) References Cited

U.S. PATENT DOCUMENTS 7,141,651 B2  11/2006  Gillies et al.

FOREIGN PATENT DOCUMENTS

| WO | WO 1998/33914 | 8/1998 | |
|---|---|---|---|
| WO | WO 2009/039409 | 3/2009 | |
| WO | WO 2009/114110 | 9/2009 | |
| WO | WO2011/109789 | * 9/2011 | |
| WO | WO 2011/109789 | 9/2011 | |
| WO | WO2012/033953 | * 3/2012 | ............ C07K 16/30 |

OTHER PUBLICATIONS

Birch, J. R. et al. "Antibody production." Advanced Drug Delivery Reviews, vol. 58, No. 5-6, Aug. 7, 2006.
Carton et al. "Codon engineering for improved antibody expression in mammalian cells." Protein Expression and Purification, Academic Press, vol. 55, No. 2, Sep. 8, 2007.
Casi, Giulio et al. "Antibody drug conjugates: Basic concepts, examples and future perspectives." Journal of Controlled Release, vol. 161, No. 2, Jan. 10, 2012.
Kalwy, S. et al. "Toward more efficient protein expression." Molecular Biotechnology, Humana Press, Inc., vol. 34, No. 2, Sp. Iss. SI, Oct. 1, 2006.
Kotsopoulou, E. et al. "Optimised mammalian expression through the coupling of codon adaptation with gene amplification; maximum yields with minimum effort." Journal of Biotechnology, vol. 146, No. 4, Apr. 15, 2010.
Ortiz-Sanchez, Elizabeth et al. "Antibody cytokine fusion proteins: applications in cancer therapy." Expert Opinion on Biological Therapy, vol. 8, No. 5, May 1, 2008.
Liu, H. et al. "Heterogenecity of monoclonal antibodies." Pharmaceutical Sciences, American Pharmaceutical Assoc., 2007, vol. 97, No. 7, pp. 2426-2447.

(Continued)

Primary Examiner — Elly-Gerald Stoica
(74) Attorney, Agent, or Firm — Marianne Fuierer; Moore & Van Allen, PLLC

(57) ABSTRACT

The present invention relates generally to the field of generating fusion proteins to be used in cancer therapy, and more specifically, to nucleotide sequences encoding the fusion proteins, wherein the chimeric fusion proteins comprises at least one targeting moiety and at least one immunomodulatory moiety that counteracts the immune tolerance of cancer cells.

6 Claims, 65 Drawing Sheets

(56) References Cited

OTHER PUBLICATIONS

Office Action, issued by the European Patent Office for corresponding European Patent Application No. 1373158.2, dated Jun. 6, 2017.
Cocco, E. et al. "hI-con1, a factor for VII-IgGFc chimeric protein targeting tissue factor for immunotherapy of uterine serous papillary carcinoma." Br. J. Cancer, 2010, vol. 3, is. 6. pp. 812-819, the abstract, pp. 813-818.
Office Action, issued by the Russian Patent Office for corresponding Russian Patent Application No. 2014145158, dated Feb. 14, 2017.

\* cited by examiner

Anti-HER2/neu-TGFβRII fusion protein at LC constant region

Amino acid sequence of Anti-HER2/neu heavy chain:

EVQLVESGGGLVQPGGSLRLSCAASGFNIKDTYIHWVRQAPGK
GLEWVARIYPTNGYTRYADSVKGRFTISADTSKNTAYLQMNSL
RAEDTAVYYCSRWGGDGFYAMDYWGQGTLVTVSSASTKGPS
VFPLAPSSKSTSGGTAALGCLVKDYFPEPVTVSWNSGALTSGV
HTFPAVLQSSGLYSLSSVVTVPSSSLGTQTYICNVNHKPSNTKV
DKKVEPKSCDKTHTCPPCPAPELLGGPSVFLFPPKPKDTLMISR
TPEVTCVVVDVSHEDPEVKFNWYVDGVEVHNAKTKPREEQYN
STYRVVSVLTVLHQDWLNGKEYKCKVSNKALPAPIEKTISKAKG
QPREPQVYTLPPSREEMTKNQVSLTCLVKGFYPSDIAVEWESN
GQPENNYKTTPPVLDSDGSFFLYSKLTVDKSRWQQGNVFSCS
VMHEALHNHYTQKSLSLSPG

Amino acid sequence of Anti-HER2/neu light chain fusion protein:

DIQMTQSPSSLSASVGDRVTITCRASQDVNTAVAWYQQKPGKA
PKLLIYSASFLYSGVPSRFSGSRSGTDFTLTISSLQPEDFATYYC
QQHYTTPPTFGQGTKVEIKRTVAAPSVFIFPPSDEQLKSGTASV
VCLLNNFYPREAKVQWKVDNALQSGNSQESVTEQDSKDSTYS
LSSTLTLSKADYEKHKVYACEVTHQGLSSPVTKSFNRGECGGG
*GSGGGGSGGGGS***TIPPHVQKSVNNDMIVTDNNGAVKFPQLCK
FCDVRFSTCDNQKSCMSNCSITSICEKPQEVCVAVWRKNDENI
TLETVCHDPKLPYHDFILEDAASPKCIMKEKKKPGETFFMCSC
SSDECNDNIIFSEEYNTSNPD**

Figure 1

Anti-EGFR1-TGFβRII fusion protein at LC constant region

Amino acid sequence of Anti-EGFR1 heavy chain:

QVQLKQSGPGLVQPSQSLSITCTVSGFSLTNYGVHWVRQSPG
KGLEWLGVIWSGGNTDYNTPFTSRLSINKDNSKSQVFFKMNSL
QSNDTAIYYCARALTYYDYEFAYWGQGTLVTVSAASTKGPSVF
PLAPSSKSTSGGTAALGCLVKDYFPEPVTVSWNSGALTSGVHT
FPAVLQSSGLYSLSSVVTVPSSSLGTQTYICNVNHKPSNTKVDK
RVEPKSCDKTHTCPPCPAPELLGGPSVFLFPPKPKDTLMISRTP
EVTCVVVDVSHEDPEVKFNWYVDGVEVHNAKTKPREEQYNST
YRVVSVLTVLHQDWLNGKEYKCKVSNKALPAPIEKTISKAKGQP
REPQVYTLPPSRDELTKNQVSLTCLVKGFYPSDIAVEWESNGQ
PENNYKTTPPVLDSDGSFFLYSKLTVDKSRWQQGNVFSCSVM
HEALHNHYTQKSLSLSPG

Amino acid sequence of Anti-EGFR1 light chain fusion protein:

DILLTQSPVILSVSPGERVSFSCRASQSIGTNIHWYQQRTNGSP
RLLIKYASESISGIPSRFSGSGSGTDFTLSINSVESEDIADYYCQQ
NNNWPTTFGAGTKLELKRTVAAPSVFIFPPSDEQLKSGTASVVC
LLNNFYPREAKVQWKVDNALQSGNSQESVTEQDSKDSTYSLS
STLTLSKADYEKHKVYACEVTHQGLSSPVTKSFNRGEC*GGGGS
GGGGSGGGGS*TIPPHVQKSVNNDMIVTDNNGAVKFPQLCKFC
DVRFSTCDNQKSCMSNCSITSICEKPQEVCVAVWRKNDENITL
ETVCHDPKLPYHDFILEDAASPKCIMKEKKKPGETFFMCSCSS
DECNDNIIFSEEYNTSNPD

Figure 2

Anti-CTLA4-TGFβRII fusion protein at LC constant region

Amino acid sequence of anti-CTLA4 heavy chain:

QVQLVESGGGVVQPGRSLRLSCAASGFTFSSYTMHWVRQAP
GKGLEWVTFISYDGNNKYYADSVKGRFTISRDNSKNTLYLQMN
SLRAEDTAIYYCARTGWLGPFDYWGQGTLVTVSSASTKGPSVF
PLAPSSKSTSGGTAALGCLVKDYFPEPVTVSWNSGALTSGVHT
FPAVLQSSGLYSLSSVVTVPSSSLGTQTYICNVNHKPSNTKVDK
RVEPKSCDKTHTCPPCPAPELLGGPSVFLFPPKPKDTLMISRTP
EVTCVVVDVSHEDPEVKFNWYVDGVEVHNAKTKPREEQYNST
YRVVSVLTVLHQDWLNGKEYKCKVSNKALPAPIEKTISKAKGQP
REPQVYTLPPSRDELTKNQVSLTCLVKGFYPSDIAVEWESNGQ
PENNYKTTPPVLDSDGSFFLYSKLTVDKSRWQQGNVFSCSVM
HEALHNHYTQKSLSLSPG

Amino acid sequence of anti-CTLA4 light chain fusion protein:

EIVLTQSPGTLSLSPGERATLSCRASQSVGSSYLAWYQQKPGQ
APRLLIYGAFSRATGIPDRFSGSGSGTDFTLTISRLEPEDFAVYY
CQQYGSSPWTFGQGTKVEIKRTVAAPSVFIFPPSDEQLKSGTA
SVVCLLNNFYPREAKVQWKVDNALQSGNSQESVTEQDSKDST
YSLSSTLTLSKADYEKHKVYACEVTHQGLSSPVTKSFNRGECG
*GGGSGGGGSGGGGS*TIPPHVQKSVNNDMIVTDNNGAVKFPQ
LCKFCDVRFSTCDNQKSCMSNCSITSICEKPQEVCVAVWRKN
DENITLETVCHDPKLPYHDFILEDAASPKCIMKEKKKPGETFFM
CSCSSDECNDNIIFSEEYNTSNPD

Figure 3

Anti-HER2/neu HC-4-1BB and LC-TGFβRII fusion protein:

Amino acid sequence of heavy chain-4-1BB fusion protein:

EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSRW
GGDGFYAMDYWGQGTLVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSL
SLSPGGGGSGGGGSGGGGSACPWAVSGARASPGSAASPRLREGPE
LSPDDPAGLLDLRQGMFAQLVAQNVLLIDGPLSWYSDPGLAGVSLTG
GLSYKEDTKELVVAKAGVYYVFFQLELRRVVAGEGSGSVSLALHLQPLR
SAAGAAALALTVDLPPASSEARNSAFGFQGRLLHLSAGQRLGVHLHT
EARARHAWQLTQGATVLGLFRVTPEIPAGLPSPRSE

Amino acid sequence of light chain-TGFβRII fusion protein:

DIQMTQSPSSLSASVGDRVTITCRASQDVNTAVAWYQQKPGKAPKLLIYS
ASFLYSGVPSRFSGSRSGTDFTLTISSLQPEDFATYYCQQHYTTPPTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGECGGGGSGGGGSGGGGSTIPPHVQKSVNNDMIVTD
NNGAVKFPQLCKFCDVRFSTCDNQKSCMSNCSITSICEKPQEVCVAVW
RKNDENITLETVCHDPKLPYHDFILEDAASPKCIMKEKKKPGETFFMCSC
SSDECNDNIIFSEEYNTSNPD

Figure 4

Anti-EGFR1 HC-4-1BB and LC-TGFβRII fusion protein:

Amino acid sequence of heavy chain-4-1BB fusion protein:

QVQLKQSGPGLVQPSQSLSITCTVSGFSLTNYGVHWVRQSPGKGLEWL
GVIWSGGNTDYNTPFTSRLSINKDNSKSQVFFKMNSLQSNDTAIYYCARA
LTYYDYEFAYWGQGTLVTVSAASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPGGGGSGGGGSGGGGS*ACPWAVSGARASPGSAASPRLREGPEL*
*SPDDPAGLLDLRQGMFAQLVAQNVLLIDGPLSWYSDPGLAGVSLTGG*
*LSYKEDTKELVVAKAGVYYVFFQLELRRVVAGEGSGSVSLALHLQPLRS*
*AAGAAALALTVDLPPASSEARNSAFGFQGRLLHLSAGQRLGVHLHTE*
*ARARHAWQLTQGATVLGLFRVTPEIPAGLPSPRSE*

Amino acid sequence of light chain-TGFβRII fusion protein:

DILLTQSPVILSVSPGERVSFSCRASQSIGTNIHWYQQRTNGSPRLLIKYA
SESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKVD
NALQSGNSQESVTEQDSKDSTYSLSSTLTLSKADYEKHKVYACEVTHQG
LSSPVTKSFNRGECGGGGSGGGGSGGGGSTIPPHVQKSVNNDMIVTDN
NGAVKFPQLCKFCDVRFSTCDNQKSCMSNCSITSICEKPQEVCVAVWR
KNDENITLETVCHDPKLPYHDFILEDAASPKCIMKEKKKPGETFFMCSCS
SDECNDNIIFSEEYNTSNPD

Figure 5

Anti-CTLA4 HC-4-1BB and LC-TGFβRII fusion protein:

Amino acid sequence of heavy chain-4-1BB fusion protein:

QVQLVESGGGVVQPGRSLRLSCAASGFTFSSYTMHWVRQAPGKGLEW
VTFISYDGNNKYYADSVKGRFTISRDNSKNTLYLQMNSLRAEDTAIYYCA
RTGWLGPFDYWGQGTLVTVSSASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPGGGGSGGGGSGGGGS*ACPWAVSGARASPGSAASPRLREGPEL
SPDDPAGLLDLRQGMFAQLVAQNVLLIDGPLSWYSDPGLAGVSLTGG
LSYKEDTKELVVAKAGVYYVFFQLELRRVVAGEGSGSVSLALHLQPLRS
AAGAAALALTVDLPPASSEARNSAFGFQGRLLHLSAGQRLGVHLHTE
ARARHAWQLTQGATVLGLFRVTPEIPAGLPSPRSE*

Amino acid sequence of light chain-TGFβRII fusion protein:

EIVLTQSPGTLSLSPGERATLSCRASQSVGSSYLAWYQQKPGQAPRLLIY
GAFSRATGIPDRFSGSGSGTDFTLTISRLEPEDFAVYYCQQYGSSPWTF
GQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGECGGGGSGGGGSGGGG**STIPPHVQKSVNNDMIV
TDNNGAVKFPQLCKFCDVRFSTCDNQKSCMSNCSITSICEKPQEVCVAV
WRKNDENITLETVCHDPKLPYHDFILEDAASPKCIMKEKKKPGETFFMC
SCSSDECNDNIIFSEEYNTSNPD**

Figure 6

Anti-HER2/neu HC-PD1 and LC-TGFβRII fusion protein:

Amino acid sequence of heavy chain-PD1 fusion protein:

EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSRW
GGDGFYAMDYWGQGTLVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSL
SLSPGGGGSGGGGSGGGGS*PGWFLDSPDRPWNPPTFSPALLVVTE*
*GDNATFTCSFSNTSESFVLNWYRMSPSNQTDKLAAFPEDRSQPGQD*
*CRFRVTQLPNGRDFHMSVVRARRNDSGTYLCGAISLAPKAQIKESL*
*RAELRVTERRAEVPTAHPSPSRPAGQFQTLV*

Amino acid sequence of light chain-TGFβRII fusion protein:

DIQMTQSPSSLSASVGDRVTITCRASQDVNTAVAWYQQKPGKAPKLLIYS
ASFLYSGVPSRFSGSRSGTDFTLTISSLQPEDFATYYCQQHYTTPPTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGECGGGGSGGGGSGGGGS**TIPPHVQKSVNNDMIVTD
NNGAVKFPQLCKFCDVRFSTCDNQKSCMSNCSITSICEKPQEVCVAVW
RKNDENITLETVCHDPKLPYHDFILEDAASPKCIMKEKKKPGETFFMCSC
SSDECNDNIIFSEEYNTSNPD**

Figure 7

Anti-EGFR1 HC-PD1 and LC-TGFβRII fusion protein:

Amino acid sequence of heavy chain-PD1 fusion protein:

QVQLKQSGPGLVQPSQSLSITCTVSGFSLTNYGVHWVRQSPGKGLEWL
GVIWSGGNTDYNTPFTSRLSINKDNSKSQVFFKMNSLQSNDTAIYYCARA
LTYYDYEFAYWGQGTLVTVSAASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPGGGGSGGGGSGGGGS*PGWFLDSPDRPWNPPTFSPALLVVTEG
DNATFTCSFSNTSESFVLNWYRMSPSNQTDKLAAFPEDRSQPGQDC
RFRVTQLPNGRDFHMSVVRARRNDSGTYLCGAISLAPKAQIKESLR
AELRVTERRAEVPTAHPSPSPRPAGQFQTLV*

Amino acid sequence of light chain-TGFβRII fusion protein:

DILLTQSPVILSVSPGERVSFSCRASQSIGTNIHWYQQRTNGSPRLLIKYA
SESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKVD
NALQSGNSQESVTEQDSKDSTYSLSSTLTLSKADYEKHKVYACEVTHQG
LSSPVTKSFNRGEC*GGGGSGGGGSGGGGS***TIPPHVQKSVNNDMIVTDN
NGAVKFPQLCKFCDVRFSTCDNQKSCMSNCSITSICEKPQEVCVAVWR
KNDENITLETVCHDPKLPYHDFILEDAASPKCIMKEKKKPGETFFMCSCS
SDECNDNIIFSEEYNTSNPD**

Figure 8

Anti-CTLA4 HC-PD1 and LC-TGFβRII fusion protein:

Amino acid sequence of heavy chain-PD1 fusion protein:

QVQLVESGGGVVQPGRSLRLSCAASGFTFSSYTMHWVRQAPGKGLEW
VTFISYDGNNKYYADSVKGRFTISRDNSKNTLYLQMNSLRAEDTAIYYCA
RTGWLGPFDYWGQGTLVTVSSASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPG*GGGGSGGGGSGGGGSPGWFLDSPDRPWNPPTFSPALLVVTEG
DNATFTCSFSNTSESFVLNWYRMSPSNQTDKLAAFPEDRSQPGQDC
RFRVTQLPNGRDFHMSVVRARRNDSGTYLCGAISLAPKAQIKESLR
AELRVTERRAEVPTAHPSPSPRPAGQFQTLV*

Amino acid sequence of light chain-TGFβRII fusionprotein:

EIVLTQSPGTLSLSPGERATLSCRASQSVGSSYLAWYQQKPGQAPRLLIY
GAFSRATGIPDRFSGSGSGTDFTLTISRLEPEDFAVYYCQQYGSSPWTF
GQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC*GGGGSGGGGSGGGGS*TIPPHVQKSVNNDMIV
TDNNGAVKFPQLCKFCDVRFSTCDNQKSCMSNCSITSICEKPQEVCVAV
WRKNDENITLETVCHDPKLPYHDFILEDAASPKCIMKEKKKPGETFFMC
SCSSDECNDNIIFSEEYNTSNPD

Figure 9

Anti-HER2/neu HC-TGFβRII-4-1BB fusion protein

Amino acid sequence of heavy chain-TGFβRII-4-1BB fusion protein:

EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSRW
GGDGFYAMDYWGQGTLVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSL
SLSPGKGGGGSGGGGSGGGGSTIPPHVQKSVNNDMIVTDNNGAVKFP
QLCKFCDVRFSTCDNQKSCMSNCSITSICEKPQEVCVAVWRKNDENITL
ETVCHDPKLPYHDFILEDAASPKCIMKEKKKPGETFFMCSCSSDECNDN
IIFSEEYNTSNPD*EPKSCDKACPWAVSGARASPGSAASPRLREGPELSP*
*DDPAGLLDLRQGMFAQLVAQNVLLIDGPLSWYSDPGLAGVSLTGGLS*
*YKEDTKELVVAKAGVYYVFFQLELRRVVAGEGSGSVSLALHLQPLRSA*
*AGAAALALTVDLPPASSEARNSAFGFQGRLLHLSAGQRLGVHLHTEA*
*RARHAWQLTQGATVLGLFRVTPEIPAGLPSPRSE*

Amino acid sequence of light chain:

DIQMTQSPSSLSASVGDRVTITCRASQDVNTAVAWYQQKPGKAPKLLIYS
ASFLYSGVPSRFSGSRSGTDFTLTISSLQPEDFATYYCQQHYTTPPTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC

Figure 10

Anti-EGFR1 HC-TGFβRII-4-1BB fusion protein

Amino acid sequence of heavy chain-TGFβRII-4-1BB fusion protein:

QVQLKQSGPGLVQPSQSLSITCTVSGFSLTNYGVHWVRQSPGKGLEWL
GVIWSGGNTDYNTPFTSRLSINKDNSKSQVFFKMNSLQSNDTAIYYCARA
LTYYDYEFAYWGQGTLVTVSAASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPGKGGGGSGGGGSGGGGS**TIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNIIF
SEEYNTSNPD***EPKSCDKACPWAVSGARASPGSAASPRLREGPELSPD
DPAGLLDLRQGMFAQLVAQNVLLIDGPLSWYSDPGLAGVSLTGGLSY
KEDTKELVVAKAGVYYVFFQLELRRVVAGEGSGSVSLALHLQPLRSAA
GAAALALTVDLPPASSEARNSAFGFQGRLLHLSAGQRLGVHLHTEAR
ARHAWQLTQGATVLGLFRVTPEIPAGLPSPRSE*

Amino acid sequence of light chain:

DILLTQSPVILSVSPGERVSFSCRASQSIGTNIHWYQQRTNGSPRLLIKYA
SESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKVD
NALQSGNSQESVTEQDSKDSTYSLSSTLTLSKADYEKHKVYACEVTHQG
LSSPVTKSFNRGEC

Figure 11

Anti-CTLA4 HC-TGFβRII-4-1BB fusion protein

Amino acid sequence of heavy chain-TGFβRII-4-1BB fusion protein:

QVQLVESGGGVVQPGRSLRLSCAASGFTFSSYTMHWVRQAPGKGLEW
VTFISYDGNNKYYADSVKGRFTISRDNSKNTLYLQMNSLRAEDTAIYYCA
RTGWLGPFDYWGQGTLVTVSSASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPGK*GGGGSGGGGSGGGGS*TIPPHVQKSVNNDMIVTDNNGAVKFPQL
**CKFCDVRFSTCDNQKSCMSNCSITSICEKPQEVCVAVWRKNDENITLET
VCHDPKLPYHDFILEDAASPKCIMKEKKKPGETFFMCSCSSDECNDNIIF
SEEYNTSNPD**EPKSCDKACPWAVSGARASPGSAASPRLREGPELSPD
DPAGLLDLRQGMFAQLVAQNVLLIDGPLSWYSDPGLAGVSLTGGLSY
KEDTKELVVAKAGVYYVFFQLELRRVVAGEGSGSVSLALHLQPLRSAA
GAAALALTVDLPPASSEARNSAFGFQGRLLHLSAGQRLGVHLHTEAR
ARHAWQLTQGATVLGLFRVTPEIPAGLPSPRSE

Amino acid sequence of light chain:

EIVLTQSPGTLSLSPGERATLSCRASQSVGSSYLAWYQQKPGQAPRLLIY
GAFSRATGIPDRFSGSGSGTDFTLTISRLEPEDFAVYYCQQYGSSPWTF
GQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC

Figure 12

Anti-HER2/neu HC-TGFβRII-PD1 fusion protein

Amino acid sequence of heavy chain-TGFβRII-PD1 fusion protein:

EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSRW
GGDGFYAMDYWGQGTLVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSL
SLSPGK*GGGGSGGGGSGGGGS*TIPPHVQKSVNNDMIVTDNNGAVKFP
QLCKFCDVRFSTCDNQKSCMSNCSITSICEKPQEVCVAVWRKNDENITL
ETVCHDPKLPYHDFILEDAASPKCIMKEKKKPGETFFMCSCSSDECNDN
IIFSEEYNTSNPD*EPKSCDKPGWFLDSPDRPWNPPTFSPALLVVTEGD*
*NATFTCSFSNTSESFVLNWYRMSPSNQTDKLAAFPEDRSQPGQDCRF*
*RVTQLPNGRDFHMSVVRARRNDSGTYLCGAISLAPKAQIKESLRAEL*
*RVTERRAEVPTAHPSPSPRPAGQFQTLV*

Amino acid sequence of light chain:

DIQMTQSPSSLSASVGDRVTITCRASQDVNTAVAWYQQKPGKAPKLLIYS
ASFLYSGVPSRFSGSRSGTDFTLTISSLQPEDFATYYCQQHYTTPPTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC

Figure 13

Anti-EGFR1 HC-TGFβRII-PD1 fusion protein:

Amino acid sequence of heavy chain-TGFβRII-PD1 fusion protein:

QVQLKQSGPGLVQPSQSLSITCTVSGFSLTNYGVHWVRQSPGKGLEWL
GVIWSGGNTDYNTPFTSRLSINKDNSKSQVFFKMNSLQSNDTAIYYCARA
LTYYDYEFAYWGQGTLVTVSAASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPGKGGGGSGGGGSGGGG**STIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNIIF
SEEYNTSNPD**EPKSCDKPGWFLDSPDRPWNPPTFSPALLVVTEGDNA
TFTCSFSNTSESFVLNWYRMSPSNQTDKLAAFPEDRSQPGQDCRFRV
TQLPNGRDFHMSVVRARRNDSGTYLCGAISLAPKAQIKESLRAELRV
TERRAEVPTAHPSPSPRPAGQFQTLV

Amino acid sequence of light chain:

DILLTQSPVILSVSPGERVSFSCRASQSIGTNIHWYQQRTNGSPRLLIKYA
SESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKVD
NALQSGNSQESVTEQDSKDSTYSLSSTLTLSKADYEKHKVYACEVTHQG
LSSPVTKSFNRGEC

Figure 14

Anti-CTLA4 HC-TGFβRII-PD1 fusion protein

Amino acid sequence of heavy chain-TGFβRII-PD1 fusion protein:

QVQLVESGGGVVQPGRSLRLSCAASGFTFSSYTMHWVRQAPGKGLEW
VTFISYDGNNKYYADSVKGRFTISRDNSKNTLYLQMNSLRAEDTAIYYCA
RTGWLGPFDYWGQGTLVTVSSASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPGKGGGGSGGGGSGGGGS**TIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNIIF
SEEYNTSNPD**EPKSCDKPGWFLDSPDRPWNPPTFSPALLVVTEGDNA
TFTCSFSNTSESFVLNWYRMSPSNQTDKLAAFPEDRSQPGQDCRFRV
TQLPNGRDFHMSVVRARRNDSGTYLCGAISLAPKAQIKESLRAELRV
TERRAEVPTAHPSPSPRPAGQFQTLV

Amino acid sequence of light chain:

EIVLTQSPGTLSLSPGERATLSCRASQSVGSSYLAWYQQKPGQAPRLLIY
GAFSRATGIPDRFSGSGSGTDFTLTISRLEPEDFAVYYCQQYGSSPWTF
GQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC

Figure 15

Nucleotide sequence of Anti-HER2/neu heavy chain constant region with linker:

```
   1 gctagcacca agggcccctc cgtgttccct ctggccccct ccagcaagtc cacctctggc
  61 ggcaccgccg ctctgggctg cctggtcaag gactacttcc ccgagcccgt gaccgtgtcc
 121 tggaactctg gcgctctgac ctccggcgtg cacaccttcc ctgccgtgct gcagtcctcc
 181 ggcctgtact ccctgtcctc cgtcgtgacc gtgccctcca gctctctggg cacccagacc
 241 tacatctgca acgtgaacca caagccctcc aacaccaagg tggacaagaa ggtggaaccc
 301 aagtcctgcg acaagaccca cacctgtccc cctgccctg ccctgagct cctgggaggc
 361 cctagcgtgt tcctgttccc cccaaagccc aaggacaccc tgatgatctc ccggaccccc
 421 gaagtgacct gcgtggtggt ggacgtgtcc cacgaggacc ctgaagtgaa gttcaattgg
 481 tacgtggacg gcgtggaagt gcacaacgcc aagaccaagc ccagagagga acagtacaac
 541 tccacctacc gggtggtgtc cgtgctgacc gtgctgcacc aggactggct gaacggcaaa
 601 gagtacaagt gcaaggtgtc caacaaggcc ctgcctgccc catcgaaaa gaccatctcc
 661 aaggccaagg gccagccccg cgagcctcag gtgtacaccc tgccccctag ccgggaagag
 721 atgaccaaga accaggtgtc cctgacctgt ctggtcaagg gcttctaccc ctccgatatc
 781 gccgtggaat gggagtccaa cggccagccc gagaacaact acaagaccac ccccccctgtg
 841 ctggactccg acggctcatt cttcctgtac tccaagctga ccgtggacaa gtcccggtgg
 901 cagcagggca acgtgttctc ctgctccgtg atgcacgagg ccctgcacaa ccactacacc
 961 cagaagtccc tgtccctgag cccaggcaaa ggcggaggcg gatctggcgg cggaggatct
...1021 ggtggcg gatcc
```

Nucleotide sequence of TGFβRII ECD:

```
   1 ggatccacca tcccccccaca cgtgcagaaa tccgtgaaca acgacatgat cgtgaccgac
  61 aacaacggcg ctgtgaagtt cccccagctg tgcaagttct gcgacgtgcg gttctctacc
 121 tgcgacaacc agaaatcctg catgtccaac tgctccatca cctccatctg cgagaagccc
 181 caggaagtgt gcgtcgccgt ctggcggaag aacgacgaga acatcaccct ggaaaccgtg
 241 tgccacgacc ccaagctgcc ctaccacgac ttcatcctgg aagatgccgc ctcccccaag
 301 tgcatcatga aggaaaagaa gaagcccggc gagactttct catgtgcag ctgctcctcc
 361 gacgagtgca acgacaacat catcttctcc gaagagtaca cacctccaa ccccgactga
 421 agctt
```

Figure 16

Nucleotide sequence of Anti-HER2/neu heavy chain variable region

```
  1 gcggccgcca tgaacttcgg cctgcggctg atcttcctgg tgctgaccct gaagggcgtg
 61 cagtgcgagg tgcagctggt ggaatccggc ggaggcctgg tccagcctgg cggatctctg
121 agactgtcct gcgccgcctc cggcttcaac atcaaggaca cctacatcca ctgggtccga
181 caggcccctg gcaagggcct ggaatgggtg gcccggatct acccaccaa cggctacacc
241 agatacgccg actccgtgaa gggccggttc accatctccg ccgacacctc caagaacacc
301 gcctacctgc agatgaactc cctgcgggcc gaggacaccg ccgtgtacta ctgctccaga
361 tggggaggcg acggcttcta cgccatggac tactggggcc agggcaccct ggtcaccgtg
421    ctccgcta gc
```

Nucleotide sequence of Anti-HER2/neu light chain variable region

```
  1 gcggccgcca tggaatccca gacccaggtg ctgatctccc tgctgttctg ggtgtccggc
 61 acctgtggcg acatccagat gacccagtcc cctccagcc tgtccgcctc tgtgggcgac
121 agagtgacca tcacctgtcg ggcctcccag gacgtgaaca ccgccgtggc ctggtatcag
181 cagaagcccg gcaaggcccc caagctgctg atctactccg cctccttcct gtactccggc
241 gtgccctccc ggttctccgg ctctagatcc ggcaccgact tacctgac catctccagc
301 ctgcagcccg aggacttcgc cacctactac tgccagcagc actacaccac ccccccacc
361 tttggccagg gcaccaaggt ggaaatcaag cggaccgtgg ccgctccctc cgtgttcatc
421    cccaccct ccgacgagca gctg
```

Nucleotide sequence of Anti-EGFR1 heavy chain constant region with linker:

```
  1 gctagcacca agggcccctc cgtgtttccc ctggcccct ccagcaagtc cacctctggc
 61 ggcaccgccg ctctgggctg cctggtcaag gactacttcc ccgagcccgt gaccgtgtcc
121 tggaactctg gcgctctgac ctccggcgtg cacaccttcc ctgccgtgct gcagtcctcc
181 ggcctgtact ccctgtcctc cgtcgtgacc gtgccctcca gctctctggg cacccagacc
241 tacatctgca acgtgaacca caagccctcc aacaccaagg tggacaagcg ggtggaaccc
301 aagtcctgcg acaagaccca cacctgtccc cctgccctg cctgaact gctgggaggc
361 ccttccgtgt tcctgttccc cccaaagccc aaggacaccc tgatgatctc ccggacccc
421 gaagtgacct gcgtggtggt ggacgtgtcc cacgaggacc ctgaagtgaa gttcaattgg
481 tacgtggacg gcgtggaagt gcacaacgcc aagaccaagc ccagagagga acagtacaac
541 tccacctacc gggtggtgtc cgtgctgacc gtgctgcacc aggactggct gaacggcaaa
601 gagtacaagt gcaaggtgtc caacaaggcc ctgcctgcc ccatcgaaaa gaccatctcc
661 aaggccaagg ccagcccg cgagcctcag gtgtacaccc tgcctcccag ccgggacgag
721 ctgaccaaga accaggtgtc cctgacctgt ctggtcaagg gcttctaccc ctccgatatc
781 gccgtggaat gggagtccaa cggccagccc gagaacaact acaagaccac cccccctgtg
841 ctggactccg acggctcatt cttcctgtac tccaagctga ccgtggacaa gtccggtgg
901 cagcagggca acgtgttctc ctgctccgtg atgcacgagg ccctgcacaa ccactacacc
961 cagaagtccc tgtctctgag ccccggcaaa ggcggcggag gatctggcgg tggcggatca
1021    ggcggag gatcc
```

Figure 17

Nucleotide sequence of Anti-EGFR1 heavy chain variable region

```
  1 gcggccgcca tgaacttcgg cctgcggctg atcttcctgg tgctgaccct gaagggcgtg
 61 cagtgccagg tgcagctgaa gcagtccgga cctggcctgg tgcagccttc ccagtccctg
121 tccatcacct gtaccgtgtc cggcttctcc ctgaccaact acggcgtgca ctgggtccga
181 cagtccccag gcaagggcct ggaatggctg ggagtgattt ggagcggcgg caacaccgac
241 tacaacaccc ccttcacctc ccggctgtcc atcaacaagg acaactccaa gtcccaggtg
301 ttcttcaaga tgaactccct gcagtccaac gacaccgcca tctactactg cgccagagcc
361 ctgacctact atgactacga gttcgcctac tggggacagg gcaccctggt caccgtgtct
421    cgctagc
```

Nucleotide sequence of Anti-EGFR1light chain variable region

```
  1 gcggccgcca tggaatccca gacccaggtg ctgatctccc tgctgttctg ggtgtccggc
 61 acctgtggcg acatcctgct gacccagtcc cccgtgatcc tgtccgtgtc tcctggcgag
121 cgggtgtcct tctcctgccg ggcctcccag tccatcggca ccaacatcca ctggtatcag
181 cagcggacca acggctcccc tcggctgctg attaagtacg cctccgagtc tatctccggc
241 atccctccc ggttctccgg ctctggctcc ggcaccgact tcaccctgtc catcaactcc
301 gtggaatccg aggatatcgc cgactactac tgccagcaga caacaactg gcccaccacc
361 ttcggcgctg gcaccaagct ggaactgaag cggaccgtgg ccgctccctc cgtgttcatc
421    cccaccct ccgacgagca gctg
```

Nucleotide sequence of Anti-CTLA4 heavy chain variable region

```
  1 gcggccgcca tgaacttcgg cctgcggctg atcttcctgg tgctgaccct gaagggcgtg
 61 cagtgccagg tgcagctggt ggaatccggc ggaggcgtgg tgcagcctgg cagatccctg
121 agactgtcct gcgccgcctc cggcttcacc ttctccagct acaccatgca ctgggtccga
181 caggcccctg gcaagggcct ggaatgggtc accttcatca gctacgacgg caacaacaag
241 tactacgccg actccgtgaa gggccggttc accatctccc gggacaactc caagaacacc
301 ctgtacctgc agatgaactc cctgcgggcc gaggacaccg ccatctacta ctgcgcccgg
361 accggctggc tgggcccttt tgattactgg ggccagggca ccctggtcac cgtgtcctcc
421    tagc
```

Nucleotide sequence of Anti-CTLA4light chain variable region

```
  1 gcggccgcca tggaatccca gacccaggtg ctgatctccc tgctgttctg ggtgtccggc
 61 acctgtggcg agatcgtgct gacccagtcc cccggcaccc tgtctctgag ccctggcgag
121 agagccaccc tgtcctgcag agcctccag tccgtgggct cctcctacct ggcttggtat
181 cagcagaagc ccggccaggc ccctcggctg ctgatctacg gcgctttctc tcgggccacc
241 ggcatccctg accggttctc tggctccggc tccggcaccg acttcaccct gaccatctcc
301 cggctggaac ccgaggactt cgccgtgtac tactgccagc agtacggctc ctcccctgg
361 acctttggcc agggcaccaa ggtggaaatc aagcggaccg tggccgctcc ctccgtgttc
421    cttcccac cctccgacga gcagctg
```

Figure 18

Nucleotide sequence of Anti CD20 IgG1 molecule:

```
   1 gctagcacaa agggccctag tgtgtttcct ctggctccct cttccaaatc cacttctggt
  61 ggcactgctg ctctgggatg cctggtgaag gattactttc ctgaacctgt gactgtctca
 121 tggaactctg gtgctctgac ttctggtgtc cacactttcc ctgctgtgct gcagtctagt
 181 ggactgtact ctctgtcatc tgtggtcact gtgccctctt catctctggg aacccagacc
 241 tacatttgta atgtgaacca caaaccatcc aacactaaag tggacaaaaa agccgaaccc
 301 aaatcctgtg acaaaaccca cacctgccca ccttgtcctg cccctgaact gctgggagga
 361 ccttctgtgt ttctgttccc accaaaacca aaagataccc tgatgatctc tagaacccct
 421 gaggtgacat gtgtggtggt ggatgtgtct catgaggacc ctgaggtcaa atttaattgg
 481 tacgtcgatg gagtggaagt ccacaatgcc aaaaccaagc ctagagagga acagtacaat
 541 tcaacctaca gagtcgtcag tgtgctgact gtgctgcatc aggattggct gaatggcaag
 601 gaatacaagt gtaaagtctc aaacaaggcc ctgcctgctc caattgagaa aacaatctca
 661 aaggccaagg gacagcctag ggaacccag gtctacaccc tgccaccttc acgcgacgaa
 721 ctgaccaaaa accaggtgtc cctgacatgc ctggtcaaag gcttctaccc ttctgacatt
 781 gctgtggagt gggagtcaaa tggacagcct gagaacaact acaaaacaac cccccctgtg
 841 ctggattctg atggctcttt cttctgtac tccaaactga ctgtggacaa gtctagatgg
 901 cagcagggga atgtcttttc ttgctctgtc atgcatgagg ctctgcataa ccactacact
 961 cagaaatccc tgtctctgtc tcccgggaaa ggcggcggag gatctggcgg aggcggttct
1021 ggtggtggcg gatcc
```

Nucleotide sequence of Anti-CD20 heavy chain variable region

```
   1 gcggccgcca tgaattttgg actgaggctg attttcctgg tgctgaccct gaaaggcgtc
  61 cagtgtcagg tgcagctgca gcagcctggt gccgagctcg tgaaacctgg cgcctccgtg
 121 aagatgtcct gcaaggcctc cggctacacc ttcaccagct acaacatgca ctgggtcaag
 181 cagacccccg gcagaggcct ggaatggatc ggcgctatct accccggcaa cggcgacacc
 241 tcctacaacc agaagttcaa gggcaaggcc accctgaccg ccgacaagtc ctcttccacc
 301 gcctacatgc agctgtcctc cctgacctcc gaggactccg ccgtgtacta ctgcgcccgg
 361 tctacctact acggcggcga ctggtacttc aacgtgtggg gcgctggcac caccgtgacc
 421 gtgtctgctg ctagc
```

Nucleotide sequence of Anti-CD20 light chain variable region

```
   1 gcggccgcca tgaattttgg actgaggctg attttcctgg tgctgaccct gaaaggcgtc
  61 cagtgtcaga tcgtgctgtc ccagtcccct gccatcctgt ctgctagccc tggcgagaaa
 121 gtgacaatga cctgccgggc ctcctcctcc gtgtcctaca tccactggtt ccagcagaag
 181 cccggctcca gcccaagcc ttggatctac gccacctcca acctggcctc tggcgtgcca
 241 gtgcggtttt ccggctctgg ctctggcacc tcctactccc tgaccatctc tcgggtggaa
 301 gccgaggatg ccgccaccta ctactgccag cagtggacca gcaaccccc cacatttggc
 361 ggaggcacca agctggaaat caagcggacc gtggcggcgc cctct
```

Figure 19

Nucleotide sequence of 4-1BB.

```
  1  ggatccgcct gtccttgggc cgtgtccggc gctagagcct ctcctggctc tgccgcctcc
 61  cccagactga gagagggccc tgagctgtcc cctgacgatc ctgccggcct gctggacctg
121  agacagggca tgtttgccca gctggtggcc cagaacgtgc tgctgatcga cggcccctg
181  tcctggtact ctgatcctgg cctggccggc gtgtccctga ccggcggact gtcctacaaa
241  gaggacacca agaactggt ggtggccaag gctggcgtgt actacgtgtt ctttcagctg
301  gaactgcggc gggtggtggc cggcgagggc tctggatctg tgtccctggc cctgcatctg
361  cagcccctga gatctgccgc tggcgccgct gctctggccc tgacagtgga tctgcctcct
421  gcctcctccg aggcccggaa ctccgcattc gggtttcagg gccggctgct gcacctgtct
481  gctggccaga gactgggagt gcatctgcac accgaggcca gagccagaca cgcctggcag
541  ctgacccagg gcgctaccgt gctgggcctg ttcagagtga ccccgagat cccagccggc
601  ctgcccagcc ctagatccga gtgataagct t
```

Nucleotide sequence of Anti-IL6R heavy chain:

```
   1  gcggccgcca tgaattttgg actgaggctg attttcctgg tgctgaccct gaaaggcgtc
  61  cagtgtcagg tgcagctgca ggaatctggc cctggactcg tgcggccttc ccaaaccctg
 121  tctctgacct gtaccgtgtc cggctactcc atcacctccg accacgcctg gtcttgggtg
 181  cgacagcctc ctggcagagg cctggaatgg atcggctaca tctcctactc cggcatcacc
 241  acctacaacc cagcctgaa gtccagagtg accatgctgc gggacaccct caagaaccag
 301  ttctccctgc ggctgtcctc cgtgaccgct gctgataccg ccgtgtacta ctgcgccaga
 361  tctctggcca ggaccaccgc catggattac tggggccagg gtccctcgt gaccgtgtcc
 421  tctgctagca ccaagggccc ctccgtgttc cctctggccc ttcctctaa atctacctct
 481  ggcggcaccg ccgctctggg ctgcctcgtg aaggactact ccccgagcc cgtgacagtg
 541  tcttggaact ctggcgccct gacctccggc gtgcacacct tccagctgt gctgcagtcc
 601  tccggcctgt actccctgtc cagcgtcgtg actgtgccct cctcatctct gggcacccag
 661  acctacatct gcaacgtgaa ccacaagccc tccaacacca aggtggacaa gaaggtggaa
 721  cccaagtcct gcgacaagac ccacacctgt cccccttgtc ctgccctga actgctgggc
 781  ggaccctctg tgttcctgtt cccaccaaaa ccgaaagaca ccctgatgat ctcccggacc
 841  cccgaagtga cctgcgtggt ggtggatgtg tccacgagg accctgaagt gaagttcaat
 901  tggtacgtgg acggcgtgga agtgcacaac gccaagacca gcctagaga ggaacagtac
 961  aactccacct accgggtggt gtccgtgctg accgtgctgc accaggattg gctgaacggc
1021  aaagagtaca agtgcaaggt gtccaacaag gccctgcctg cccccatcga aagaccatc
1081  tccaaggcca agggccagcc acgggaaccc caggtgtaca cactgccccc tagccgcgac
1141  gagctgacca agaatcaggt gtccctgaca tgcctgtgac aaggcttcta cccctccgat
1201  atcgccgtgg aatgggagtc caacggccag cctgagaaca actacaagac cacccccct
1261  gtgctggact ccgacggctc attcttcctg tactcaaagc tgacagtgga caagtcccgg
1321  tggcagcagg gcaacgtgtt ctcctgctcc gtgatgcacg aggccctgca caaccactac
1381  acccagaagt ccctgtccct gagccccggg aaaggcggcg aggatctgg cggaggcggt
1441  tctggtggtg gcggatcc
```

Figure 20

Nucleotide sequence of Anti-IL6R light chain variable region:

```
  1 gcggccgcca tgaattttgg actgaggctg attttcctgg tgctgaccct gaaaggcgtc
 61 cagtgtgaca tccagatgac ccagtccccc tccagcctgt ctgcctctgt gggcgacaga
121 gtgaccatca cctgtcgggc ctcccaggac atctcctcct acctgaactg gtatcagcag
181 aagcccggca aggcccccaa gctgctgatc tactacacct cccggctgca ctccggcgtg
241 ccctctagat tttccggctc tggctccggc accgacttta ccttcaccat cagctccctg
301 cagcccgagg atatcgccac ctactactgc cagcaaggca caccctgcc ctacaccttt
361 ggccagggca ccaaggtgga aatcaagcgg accgtggcgg cgccc
```

Nucleotide sequence of Anti-4-1BB heavy chain

```
   1 gcggccgcca tgaattttgg actgaggctg attttcctgg tgctgaccct gaaaggcgtc
  61 cagtgtcagg tgcagctgca gcagtgggga gctggactgc tgaagccctc cgagacactg
 121 tctctgacct gcgctgtgta cggcggctcc ttctccggct actactggtc ctggattcgg
 181 cagtcccctg agaagggcct ggaatggatc ggcgagatca ccacggcgg ctacgtgacc
 241 tacaacccca gcctggaatc cagagtgacc atctccgtgg acacctccaa gaaccagttc
 301 tccctgaagc tgtcctccgt gaccgccgct gataccgccg tgtactactg cgccagagac
 361 tacggccctg caactacga ctggtacttc gacctgtggg gcagaggcac cctcgtgacc
 421 gtgtcctctg ctagcaccaa gggcccctcc gtgtttcctc tggccccttg ctcacgctcc
 481 acctccgaat ctaccgccgc tctgggctgc ctcgtgaagg actacttccc cgagcccgtg
 541 actgtgtctt ggaactctgg cgccctgacc tccggcgtgc acacctttcc agctgtgctg
 601 cagtcctccg gcctgtactc cctgtccagc gtcgtgacag tgccctccag ctctctgggc
 661 accaagacct acacctgtaa cgtggaccac aagccctcca acaccaaggt ggacaagcgg
 721 gtggaatcta atacggccc tcctgccct ccttgcccag ccctgaatt tctggcgga
 781 ccttccgtgt tcctgttccc cccaaaaccc aaggacaccc tgatgatctc ccggacccc
 841 gaagtgacct gcgtggtggt ggatgtgtcc caggaagatc ccgaggtgca gttcaattgg
 901 tacgtggacg gcgtggaagt gcacaacgcc aagaccaagc ctagagagga acagttcaac
 961 tccacctacc gggtggtgtc cgtgctgacc gtgctgcacc aggattggct gaacggcaaa
1021 gagtacaagt gcaaggtgtc caacaagggc ctgcccagct ccatcgaaaa gaccatcagc
1081 aaggccaagg ccagccccg gaacccag gtgtacacac tgcctccaag ccaggaagag
1141 atgaccaaga tcaggtgtc cctgacctgt ctcgtgaaag gcttctaccc ctccgatatc
1201 gccgtggaat gggagtccaa cggccagcct gagaacaact acaagaccac cccccctgtg
1261 ctggactccg acggcagctt cttcctgtac tctcgcctga ccgtggacaa gtcccggtgg
1321 caggaaggca acgtgttctc tgctccgtg atgcacgagg ccctgcacaa ccactacacc
1381 cagaagtccc tgtccctgtc tctggggaaa ggcggcggag gatctggcgg aggcggttct
1441 ggtggtggcg gatcc
```

Nucleotide sequence of Anti-4-1BB light chain variable region

```
  1 gcggccgcca tgaattttgg actgaggctg attttcctgg tgctgaccct gaaaggcgtc
 61 cagtgtgaga tcgtgctgac ccagtctcct gccaccctgt ctctgagccc tggcgagaga
121 gctaccctgt cctgccgtgc ctcccaatcc gtgtcctctt acctggcctg gtatcagcaa
181 aagcccggcc aggctccccg gctgctgatc tacgatgcct ccaatagagc caccggcatc
241 cctgccagat ctccggctc tggctctggc accgacttta ccctgaccat ctcctctctg
301 gaacccgagg acttcgccgt gtactactgc cagcagcggt ccaactggcc tcccgccctg
361 acatttggcg gaggcaccaa ggtggaaatc aagcggaccg tggcggcgcc c
```

Figure 21

A
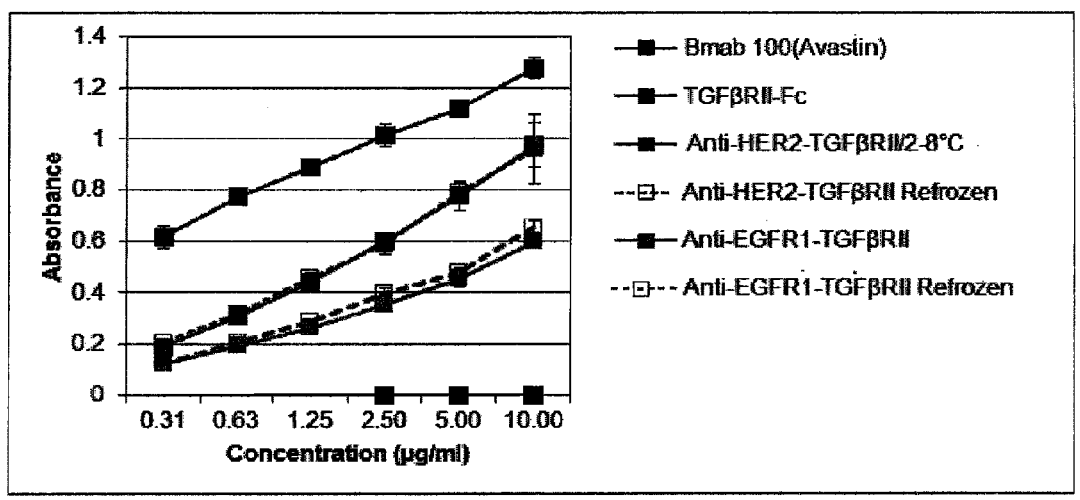
B
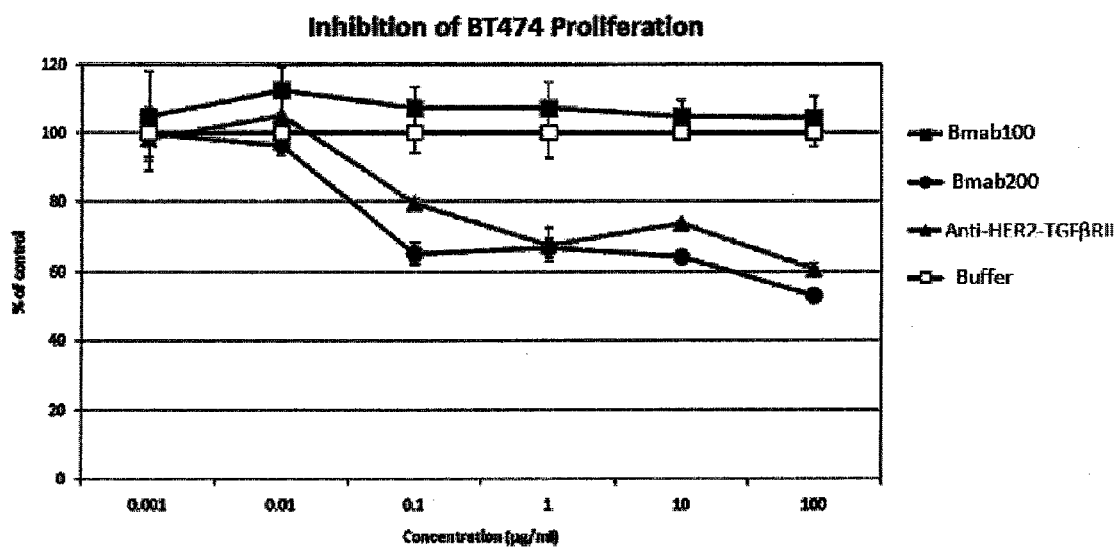
Figure 24

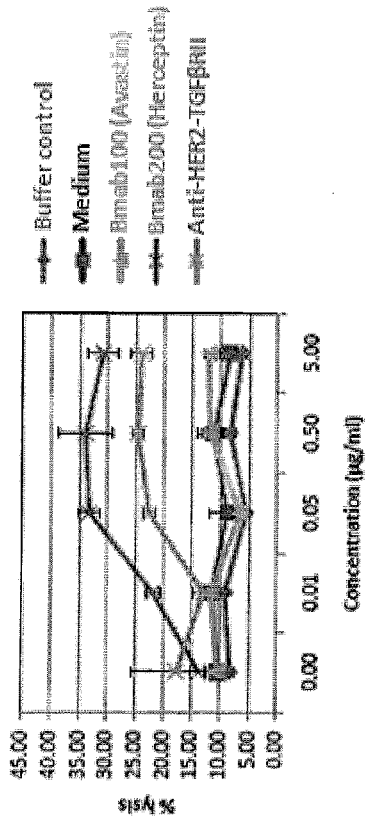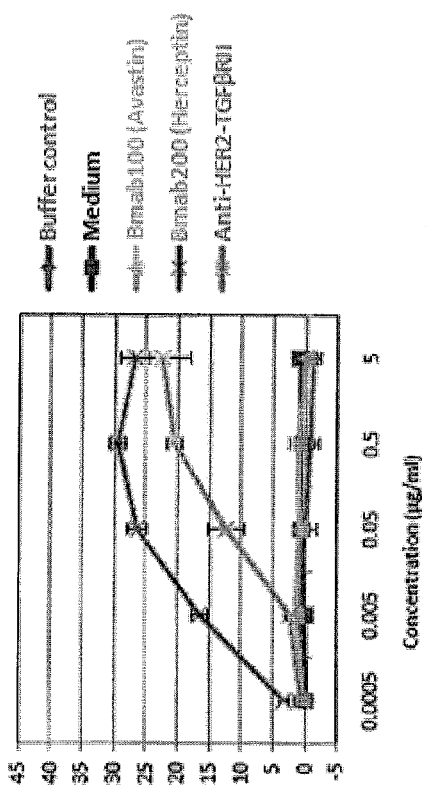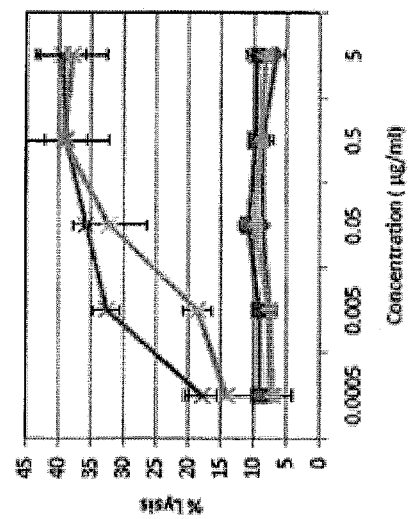
Figure 26

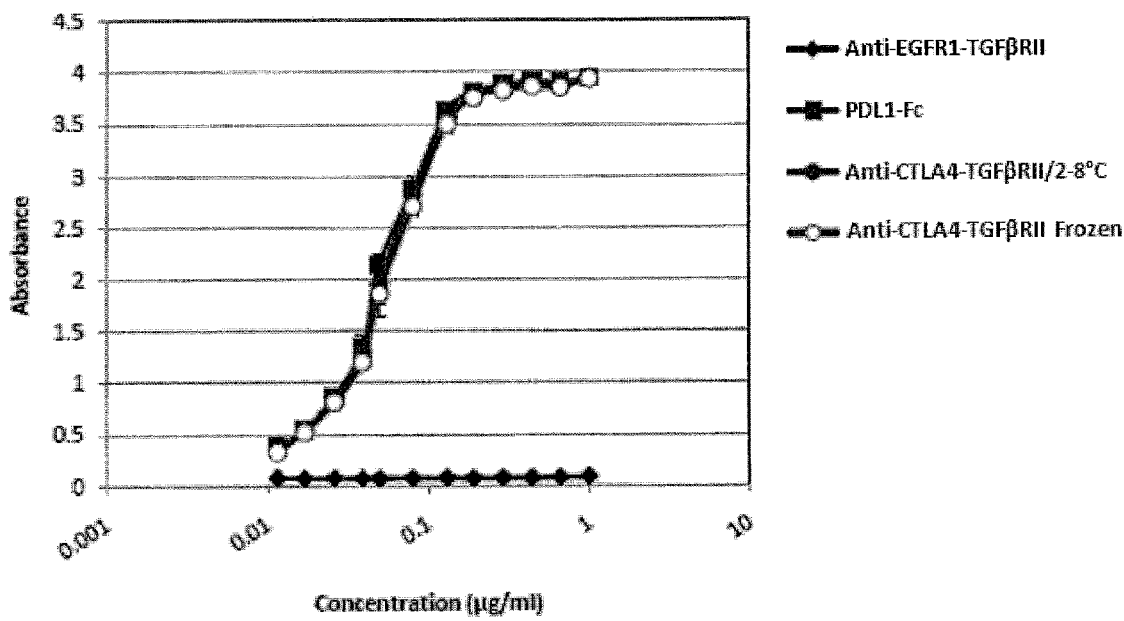
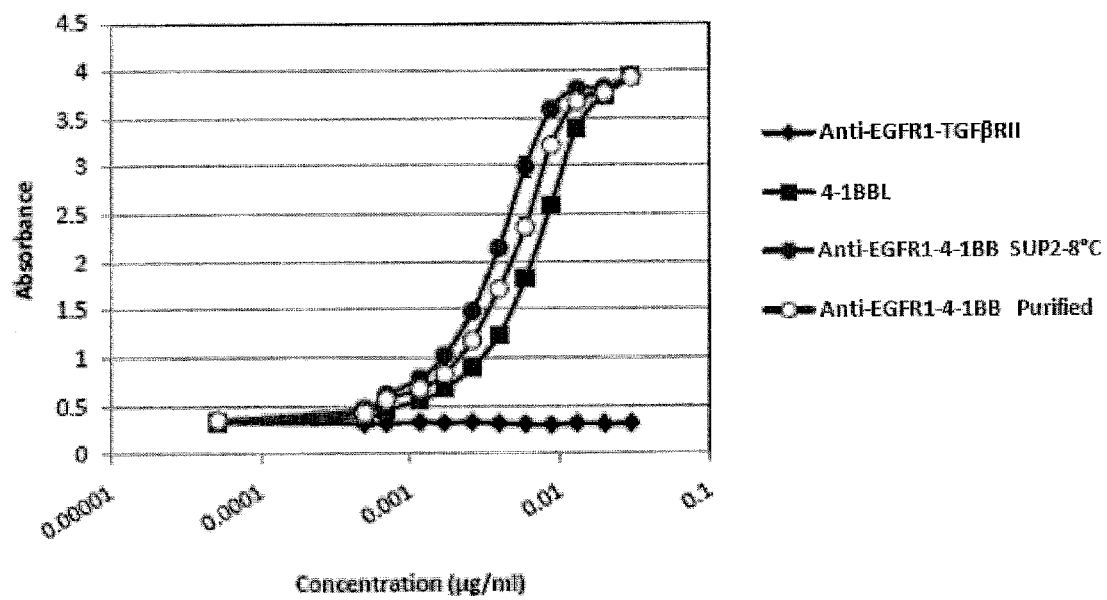
Figure 30

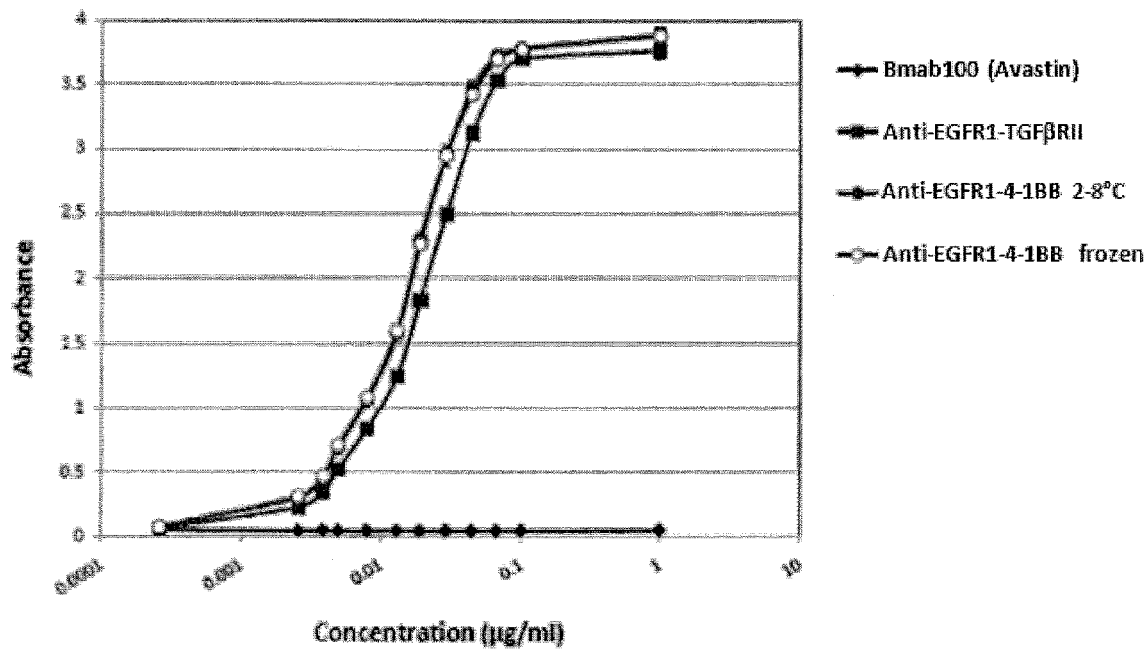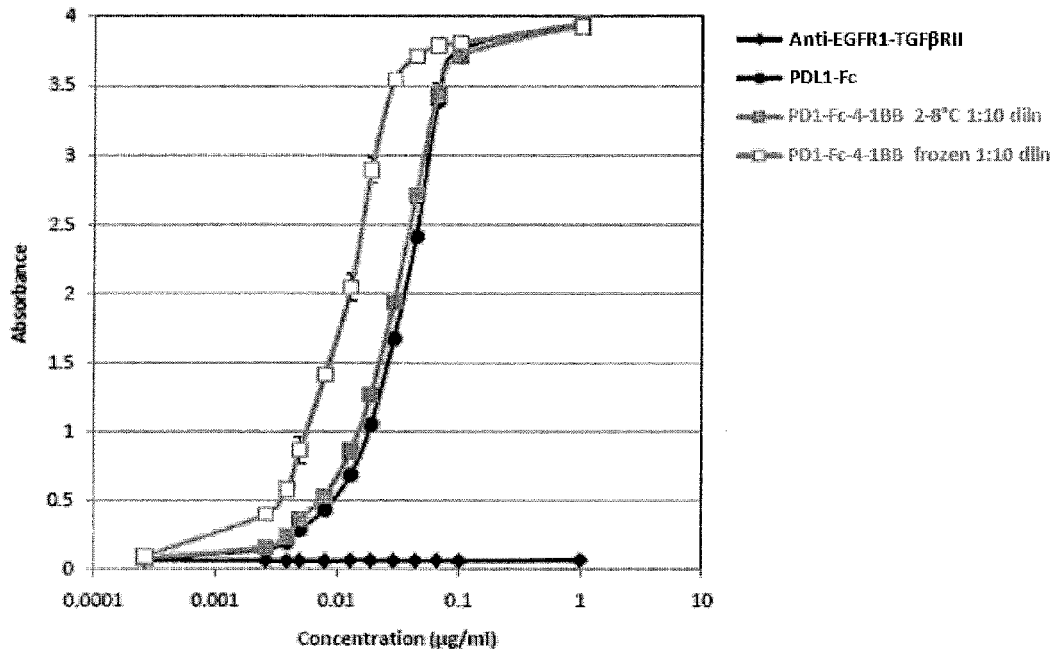
Figure 31

1. Measurement of whole protein Molecular weight, presence of Glycosylation
2. Reduction alkylation → Heavy and light chain and peptide digestion → primary Sequence Identification and confirmation
3. MS/MS of protein and peptides for proteome profiling, sequence and PTM confirmation
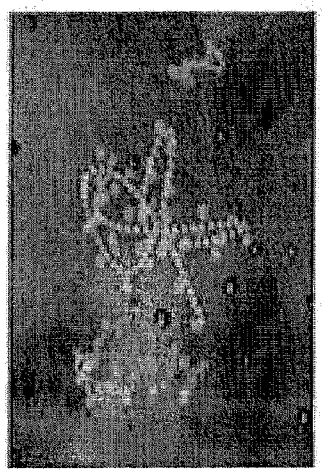
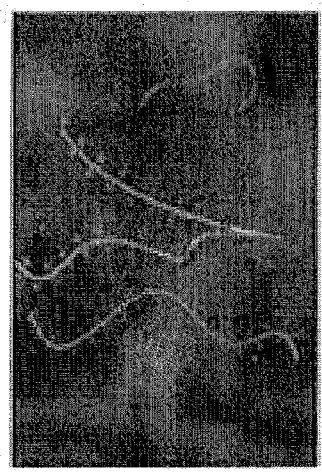
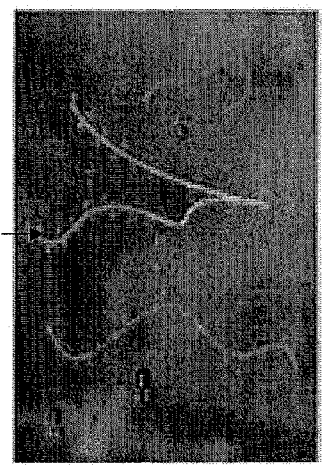
Figure 33

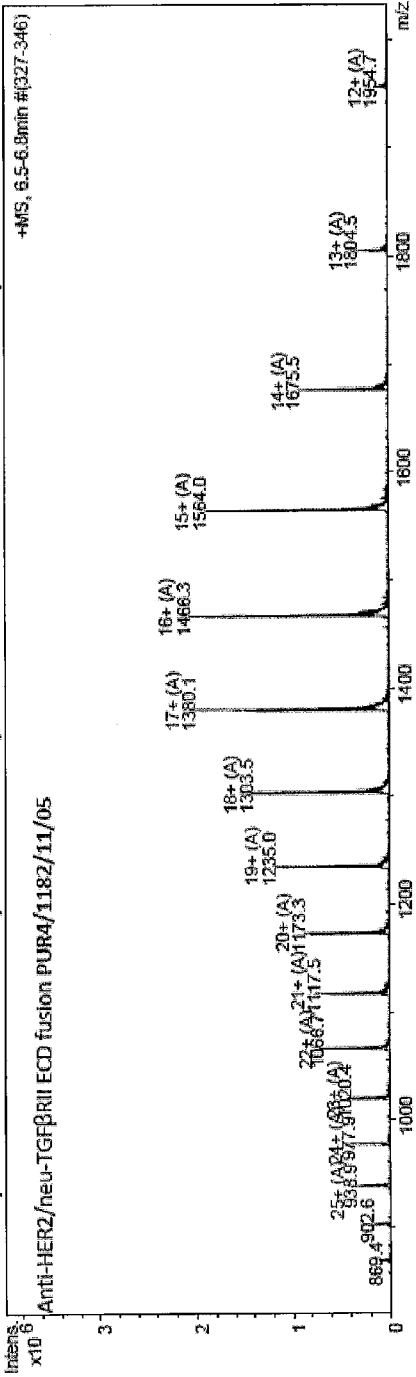
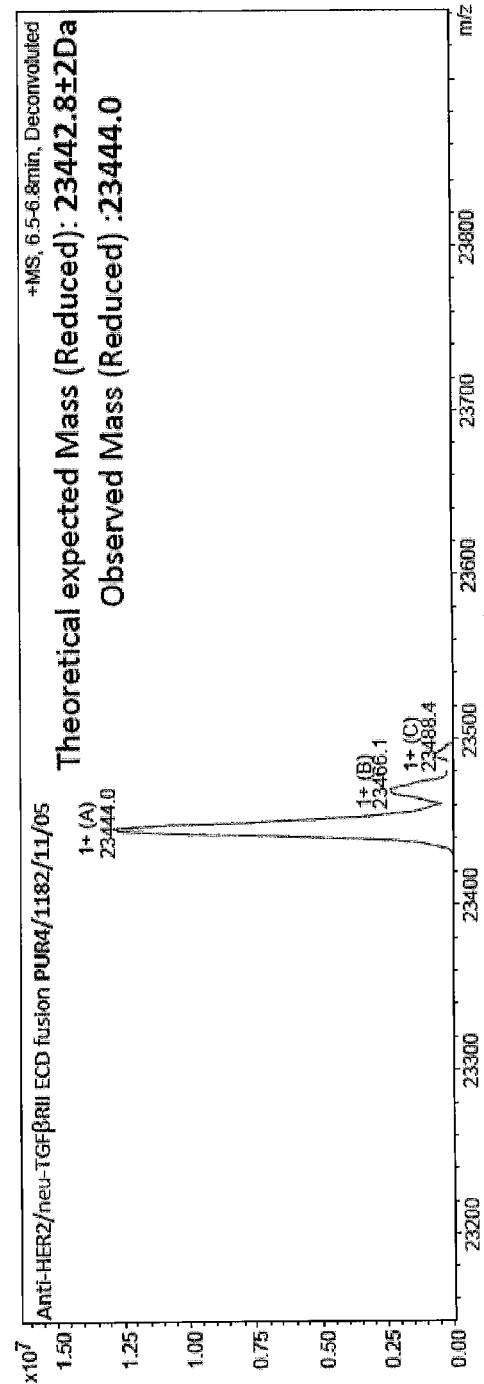
Figure 34

List of Expected/Observed Tryptic Peptide of LC of Anti-HER2/neu-TGFβRII ECD fusion

| S.No | Range | Sequence | Expected Mass (M+H)+ | Observed Mass (M+H)+ | RT(min) | MS/MS |
|---|---|---|---|---|---|---|
| 1 | LC(1-18) | DIQMTQSPSSLSASVGDR | 1878.9 | 1879.2, 940.1+2 | 57.3 | Yes |
| 2 | LC(19-24) | VTITCR | 749.3 | 749.4 | 31.7 | Yes |
| 3 | LC(25-42) | ASQDVNTAVAWYQQKPGK | 1990.9 | 1991.2, 996.1+2 | 58.1 | Yes |
| 4 | LC(43-45) | APK | 314.9 | 315.3 | 5.9 | Yes |
| 5 | LC(46-61) | LLIYSASFLYSGVPSR | 1772.9 | 1773.1 | 93.1 | Yes |
| 6 | LC(62-66) | FSGSR | 553.2 | 553.3 | 16.3 | Yes |
| 7 | LC(67-103) | SGTDFTLTISSLQPEDFATYYCQQHYT | 4187.9 | 4188.1 | 95.7 | NO |
| 8 | LC(104-107) | VEIK | 488.3 | 488.3 | 26.2 | Yes |
| 9 | LC(108-108) | R | 175.1 | Out of detection range | | |
| 10 | LC(109-126) | TVAAPSVFIFPPSDEQLK | 1946.02 | 1946.1 | 89.1 | Yes |
| 11 | LC(127-142) | SGTASVVCLLNNFYPR | 1797.8 | 1797.9 | 97.4 | Yes |
| 12 | LC(143-145) | EAK | 347.1 | Out of detection range | | |
| 13 | LC(146-149) | VQWK | 560.3 | 560.4 | 34.3 | Yes |
| 14 | LC(150-169) | VDNALQSGNSQESVTEQDSK | 2135.9 | 2136.2 | 35.6 | Yes |
| 15 | LC(170-183) | DSTYSLSSTLTLSK | 1502.7 | 1502.9 | 67.8 | Yes |
| 16 | LC(184-188) | ADYEK | 625.2 | 625.4 | 6.5 | Yes |
| 17 | LC(189-190) | HK | 284.1 | Out of detection range | | |
| 18 | LC(191-207) | VYACEVTHQGLSSPVTK | 1875.9 | 1876.1 | 52.3 | Yes |
| 19 | LC(208-211) | SFNR | 523.2 | 523.3 | 52.3 | Yes |
| 20 | LC(212-214) | GEC | 365.1 | Out of detection range | | |

Figure 39

List of Expected/Observed Tryptic Peptide of HC of Anti-HER2/neu-TGFβRII ECD fusior

| S.No | Range | Sequence | Expected Mass [(M+H)+] | Observed Mass [(M+H)+] | Rt(min) | MS/MS |
|---|---|---|---|---|---|---|
| 1 | HC(1-19) | EVQLVESGGGLVQPGGSLR | 1881.9 | 1882.2, 941.6+2 | 68.5 | YES |
| 2 | HC(20-30) | LSCAASGFNIK | 1167.5 | 1167.8, 584.4+2 | 55.2 | YES |
| 3 | HC(31-38) | DTYIHWVR | 1089.5 | 1089.6, 545.3+2 | 64.2 | YES |
| 4 | HC(39-43) | QAPGK | 500.2 | 500.3 | 7.4 | YES |
| 5 | HC(44-50) | GLEWVAR | 830.4 | 830.5 | 60.6 | YES |
| 6 | HC(51-59) | IYPTNGYTR | 1084.5 | 1084.6, 542.8+2 | 38.1 | YES |
| 7 | HC(60-65) | VADSVK | 682.3 | 682.4 | 21.6 | YES |
| 8 | HC(66-67) | GR | 232.1 | Out of detection range | | |
| 9 | HC(68-76) | FTISADTSK | 969.4 | 969.5, 485.3+2 | 45.3 | YES |
| 10 | HC(77-87) | NTAYLQMNSLR | 1310.6 | 1310.6, 655.8+2 | 61.4 | YES |
| 11 | HC(88-98) | AEDTAVYYCSR | 1334.6 | 1334.8, 667.9+2 | 38.9 | YES |
| 12 | HC(99-124) | WGGDGFYAMDYWGQGTLVTVSSASTK | 2784.2 | 2784.3, 1393.2+2 | 95.7 | YES |
| 13 | HC(125-136) | GPSVFPLAPSSK | 1186.6 | 1186.8, 593.9+2 | 67.1 | YES |
| 14 | HC(137-150) | STSGGTAALGCLVK | 1321.6 | 1321.8, 661.4+2 | 61.1 | YES |
| 15 | HC(151-213) | DYFPEPVTVSWNSGALTS....LGTQTYIC | 6713.3 | 6, 1679.7+4, 1343.8+5, 1120 | 102.6 | NO |
| 16 | HC(214-216) | VDK | 361.2 | Out of detection range | | |
| 17 | HC(217-217) | K | 147.1 | Out of detection range | | |
| 18 | HC(218-221) | VEPK | 472.2 | 472.3 | 11.5 | YES |
| 19 | HC(222-225) | SCDK | 509.1 | 509.4 | 5.2 | YES |
| 20 | HC(226-251) | THTCPPCPAPELLGGPSVFLFPPKPK | 2844.4 | 2844.6, 949.4+3 | 95.9 | YES |
| 21 | HC(252-258) | DTLMISR | 835.4 | 835.5 | 48.7 | YES |
| 22 | HC(259-277) | TPEVTCVVVDVSHEDPEVK | 2139.1 | 2139.2, 1070.1+2, 713.8+2 | 73.6 | YES |
| 23 | HC(278-291) | FNWYVDGVEVHNAK | 1677.7 | 1677.8, 839.5+2 | 73.1 | YES |
| 24 | HC(292-295) | TKPR | 501.3 | 501.3 | 7.2 | YES |
| 25 | HC(296-304) | EEQYNSTYR (GP) | 1189.5+1444 | 2633.5, 1317.6+2 | 25.1 | YES |
| 26 | HC(305-320) | VVSVLTVLHQDWLNGK | 1807.9 | 1808.1, 904.5+2 | 99.1 | YES |
| 27 | HC(321-323) | EYK | 439.2 | 439.3 | 5.2 | YES |
| 28 | HC(324-325) | CK | 307.1 | Out of detection range | | |
| 29 | HC(326-329) | VSNK | 447.2 | 447.3 | 5.4 | YES |
| 30 | HC(330-337) | ALPAPIEK | 838.4 | 838.5 | 47.5 | YES |
| 31 | HC(338-341) | TISK | 448.2 | 448.3 | 13.9 | YES |
| 32 | HC(342-343) | AK | 218.1 | | | |
| 33 | HC(344-347) | GQPR | 457.3 | 457.3 | 6.9 | YES |
| 34 | HC(348-358) | EPQVYTLPPSR | 1286.6 | 1286.7, 643.9+2 | 52.8 | YES |
| 35 | HC(359-363) | EEMTK | 637.2 | 637.4 | 6.2 | YES |
| 36 | HC(364-373) | NQVSLTCLVK | 1161.6 | 1161.7, 581.4+2 | 67.5 | YES |
| 37 | HC(374-395) | GFYPSDIAVEWESNGQPENNYK | 2545.1 | 2545.1, 1273.1+2, 849.1+3 | 81.1 | YES |
| 38 | HC(396-412) | TTPPVLDSDGSFFLYSK | 1873.9 | 1874.2, 937.6+2 | 85.8 | YES |
| 39 | HC(413-417) | LTVDK | 575.3 | 575.4 | 27.4 | YES |
| 40 | HC(418-419) | SR | 262.1 | Out of detection range | | |
| 41 | HC(420-442) | WQQGNVFSCSVMHEALHNHYTQK | 2801.2 | 2801.4, 1401.2+2, 934.5+3 | 77.4 | YES |
| 42 | HC(443-450) | SLSLSPGK | 788.4 | 788.5 | 44.3 | YES |

Figure 40

List of Expected/Observed Tryptic Peptide of LM* of Anti-HER2/neu-TGFβRII ECD fusion

| S.No | Range | Sequence | Expected Mass (M+H)+ | Observed Mass (M+H)+ | RT(min) | MS/MS |
|---|---|---|---|---|---|---|
| 1 | LM(1-23) | GGGGSGGGGSGGGGSTIPPHVQK | 1864.8 | 1864.2, 932.6+2 | 76.1 | NO |
| 2 | LM(24-39) | SVNNDMIVTDNNGAVK | 1690.7 | 1690.8, 846.1+2 | 49.3 | YES |
| 3 | LM(40-45) | FPQLCK | 792.4 | 792.5 | 51.3 | YES |
| 4 | LM(46-50) | FCDVR | 696.3 | 696.4 | 29.8 | YES |
| 5 | LM(51-58) | FSTCDNQK | 999.4 | 999.5 | 22.1 | YES |
| 6 | LM(59-82) | SCMSNCSITSICEKPQEVCIAVWR | 2901.2 | Not Detected | | |
| 7 | LM(83-83) | K | 147.1 | Out of detection range | | |
| 8 | LM(84-98) | NDENITLETVCHDPK | 1784.8 | 1785.1 | 54.2 | YES |
| 9 | LM(99-113) | LPYHDFILEDAASPK | 1715.8 | 1715.9 | 77.2 | YES |
| 10 | LM(114-117) | CIMK | 551.2 | 551.3 | 27.8 | YES |
| 11 | LM(118-119) | EK | 276.1 | Out of detection range | | |
| 12 | LM(120-120) | K | 147.1 | Out of detection range | | |
| 13 | LM(121-152) | KPGETFFMCSCSSDECNDNIIFSEEYNTSNPD | 3794.8 | Not Detected | | |

Figure 41

List of expected/observed peptides of Light Chain(LC) of Anti-EGFR1-TGFβRII ECD.

| S.No | Peptide | Sequence | Expected Mss(M+H)+ | Observed Mass (M+H)+ | RT(MIN) | MS/MS |
|---|---|---|---|---|---|---|
| 1 | LC(1-18) | DILLTQSPVILSVSPGER | 1924 | 1924 | 89.2 | Yes |
| 2 | LC(19-24) | VSFSCR | 755.3 | 755.4 | 35.9 | Yes |
| 3 | LC(25-39) | ASQSIGTNIHWYQQR | 1788.8 | 1789 | 61.7 | Yes |
| 4 | LC(40-45) | TNGSPR | 631.3 | 631.4 | 8.2 | Yes |
| 5 | LC(46-49) | LLIK | 486.3 | 486.3 | 47.9 | Yes |
| 6 | LC(50-61) | YASESISGIPSR | 1266.6 | 1266.6 | 48 | Yes |
| 7 | LC(62-103) | FSGSGSGTDFTLSINSVESED | 4565.9 | 4565.9 | 93.1 | NO |
| 8 | LC(104-107) | LELK | 502.3 | 502.4 | 37.8 | Yes |
| 9 | LC(108-108) | R | 174.1 | Out of detection range | | |
| 10 | LC(109-126) | TVAAPSVFIFPPSDEQLK | 1946 | 1946.2 | 89.5 | Yes |
| 11 | LC(127-142) | SGTASVVCLLNNFYPR | 1797.8 | 1797.2 | 97.1 | Yes |
| 12 | LC(143-145) | EAK | 347.1 | Out of detection range | | |
| 13 | LC(146-149) | VQWK | 560.3 | 560.4 | 34.3 | Yes |
| 14 | LC(150-169) | VDNALQSGNSQESVTEQDS | 2135.9 | 2136.2 | 35.6 | Yes |
| 15 | LC(170-183) | DSTYSLSSTLTLSK | 1502.7 | 1502.9 | 67.8 | Yes |
| 16 | LC(184-188) | ADYEK | 625.2 | 625.3 | 7 | Yes |
| 17 | LC(189-190) | HK | 284.1 | Out of detection range | | |
| 18 | LC(191-207) | VYACEVTHQGLSSPVTK | 1875.9 | 1876.2 | 52.5 | Yes |
| 19 | LC(208-211) | SFNR | 523.2 | 523.3 | 20.1 | Yes |
| 20 | LC(212-214) | GEC | 365.1 | Out of detection range | | |

Figure 43

List of expected/observed peptides of Heavy Chain(HC) of Anti-EGFR1-TGFβRII ECD

| S.No | Peptide | Sequence | Expected Mass (M+H)+ | Observed Mass (M+H)+ | RT (Min) | MS/MS |
|---|---|---|---|---|---|---|
| 1 | HC(1-5) | QVQLK | 615.3 | 598.4* | 37.1 | yes |
| 2 | HC(6-38) | QSGPGLVQPSQSLSITCTVSGFSLTNYGVH | 3564.9 | 3564.7 | 96.8 | yes |
| 3 | HC(39-43) | QSPGK | 516.2 | 516.3 | 6.4 | yes |
| 4 | HC(44-66) | GLEWLGVIWSGGNTDYNTPFTSR | 2571.7 | 2571.4 | 101.8 | YES |
| 5 | HC(67-71) | LSINK | 574.3 | 574.5 | 33.2 | YES |
| 6 | HC(72-75) | DNSK | 463.2 | Not Detected | | |
| 7 | HC(76-96) | SQVFFMNSLQSNDTAIYYCAR | 2515.1 | Not Detected | | |
| 8 | HC(97-122) | ALTYYDYEFAYWGQGTLVTVSAASTK | 2907.1 | Not Detected | | |
| 9 | HC(123-134) | GPSVFPLAPSSK | 1186.6 | 1186.8 | 66.9 | yes |
| 10 | HC(135-148) | STSGGTAALGCLVK | 1321.6 | 1321.8 | 61.1 | yes |
| 11 | HC(149-211) | DYFPEPVTVSWNSGALTSGVHTFPAVLQS | 6716.3 | 6715 | 102.6 | NO |
| 12 | HC(212-214) | VDK | 361.2 | Not Detected | | |
| 13 | HC(215-215) | R | 175.1 | Out of Detection Range | | |
| 14 | HC(216-219) | VEPK | 472.2 | 472.3 | 11.2 | yes |
| 15 | HC(220-223) | SCDK | 509.1 | Not Detected | | |
| 16 | HC(224-249) | THTCPPCPAPELLGGPSVFLFPPKPK | 2845.3 | 2845.6 | 95.8 | yes |
| 17 | HC(250-256) | DTLMISR | 835.4 | 835.5 | 48.9 | yes |
| 18 | HC(257-275) | TPEVTCVVVDVSHEDPEVK | 2139 | 2139.4 | 73.6 | yes |
| 19 | HC(276-289) | FNWYVDGVEVHNAK | 1677.7 | 1677.8 | 73.1 | yes |
| 20 | HC(290-293) | TKPR | 501.3 | 501.4 | 7.1 | yes |
| 21 | HC(294-302) | EEQYNSTYR | 1188.5 | (+1444)Da 2634.2 | 25 | yes |
| 22 | HC(303-318) | VVSVLTVLHQDWLNGK | 1809.1 | 1809.4 | 99 | YES |
| 23 | HC(319-321) | EYK | 439.2 | 439.3 | 5.4 | yes |
| 24 | HC(322-323) | CK | 307.1 | Out of Detection Range | | |
| 25 | HC(324-327) | VSNK | 447.2 | 447.3 | 5.4 | yes |
| 26 | HC(328-335) | ALPAPIEK | 838.4 | 838.5 | 47.9 | yes |
| 27 | HC(336-339) | TISK | 448.2 | 448.3 | 14 | yes |
| 28 | HC(340-341) | AK | 218.1 | Out of Detection Range | | |
| 29 | HC(342-345) | GQPR | 457.2 | 457.3 | 6.9 | yes |
| 30 | HC(346-356) | EPQVYTLPPSR | 1286.6 | 1286.7 | 52.8 | YES |
| 31 | HC(357-361) | DELTK | 605.3 | 605.4 | 11.3 | yes |
| 32 | HC(362-371) | NQVSLTCLVK | 1161.6 | 1161.7 | 67.4 | yes |
| 33 | HC(372-393) | GFYPSDIAVEWESNGQPENNYK | 2545.6 | 2545.4 | 80.8 | YES |
| 34 | HC(394-410) | TTPPVLDSDGSFFLYSK | 1873.9 | 1874 | 85.7 | yes |
| 35 | HC(411-415) | LTVDK | 575.3 | 575.4 | 27.2 | yes |
| 36 | HC(416-417) | SR | 262.1 | Out of Detection Range | | |
| 37 | HC(418-440) | WQQGNVFSCSVMHEALHNHYTQK | 2801.2 | 2801.4 | 77.4 | NO |
| 38 | HC(441-448) | SLSLSPGK | 788.4 | 788.5 | 44.2 | yes |

Figure 44

List of expected/observed peptides of Linked Motif (LM) of Anti-EGFR1-TGFβRII ECD

| S.No | Peptide | Sequence | Expected Mass (M+H)+ | Observed Mass (M+H)+ | RT (Min) | MS/MS |
|---|---|---|---|---|---|---|
| 1 | LM(1-23) | GGGGSGGGGSGGGGSGGGGSTPPHVQK | 1864.8 | 1864.2 | 76.3 | NO |
| 2 | LM(24-39) | SVNNDMIVTDNNGAVK | 1691.7 | 1691.8 | 49.2 | YES |
| 3 | LM(40-45) | FPQLCK | 792.4 | 792.5 | 51.5 | YES |
| 4 | LM(46-50) | FCDVR | 696.3 | 696.4 | 29.8 | YES |
| 5 | LM(51-58) | FSTQDNQK | 999.4 | 999.5 | 21.9 | YES |
| 6 | LM(59-82) | SCMSNCSITSICEKPQEVCVAVWR | 2903.3 | Not Detected | | |
| 7 | LM(83-83) | K | 147.1 | Out of Detection Range | | |
| 8 | LM(84-98) | NDENITLETVCHDPK | 1784.8 | 1784.8 | 54.3 | YES |
| 9 | LM(99-113) | LPYHDFILEDAASPK | 1715.8 | 1715.9 | 77.1 | YES |
| 10 | LM(114-117) | CIMK | 551.2 | 551.3 | 27.7 | YES |
| 11 | LM(118-119) | EK | 276.1 | Out of Detection Range | | |
| 12 | LM(120-120) | K | 147.1 | Out of Detection Range | | |
| 13 | LM(121-152) | KPGETFFMCSCSSDECNDNIIFSEEYNTSNPD | 3796.9 | Not Detected | | |

Figure 45

Cantuzumab -TGFβRII fusion protein at LC constant region

Amino acid sequence of Cantuzumab heavy chain:

QVQLVQSGAEVKKPGETVKISCKASDYTFTYYGMNWVKQAPGQGLKWMGWI
DTTTGEPTYAQKFQGRIAFSLETSASTAYLQIKSLKSEDTATYFCARRGPYNWYFD
VWGQGTTVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMH
EALHNHYTQKSLSLSPGK

Amino acid sequence of Cantuzumab light chain fusion protein:

DIVMTQSPLSVPVTPGEPVSISCRSSKSLLHSNGNTYLYWFLQRPGQSPQLLIYR
MSNLVSGVPDRFSGSGSGTAFTLRISRVEAEDVGVYYCLQHLEYPFTFGPGTKLE
LKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC
*GGGGSGGGGSGGGGS***TIPPHVQKSVNNDMIVTDNNGAVKFPQLCK
FCDVRFSTCDNQKSCMSNCSITSICEKPQEVCVAVWRKNDENI
TLETVCHDPKLPYHDFILEDAASPKCIMKEKKKPGETFFMCSC
SSDECNDNIIFSEEYNTSNPD**

Figure 46

Cixutumumab -TGFβRII fusion protein at LC constant region

Amino acid sequence of Cixutumumab heavy chain:

EVQLVQSGAEVKKPGSSVKVSCKASGGTFSSYAISWVRQAPGQGLEWMGGIIPI
FGTANYAQKFQGRVTITADKSTSTAYMELSSLRSEDTAVYYCARAPLRFLEWSTQ
DHYYYYMDVWGKGTTVTVSSASTKGPSVFPLAPSSKSTSGGTAALGCLVKDYF
PEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQGN
VFSCSVMHEALHNHYTQKSLSLSPGK

Amino acid sequence of Cixutumumab light chain fusion protein:

SSELTQDPAVSVALGQTVRITCQGDSLRSYYATWYQQKPGQAPILVIYGENKRPS
GIPDRFSGSSSGNTASLTITGAQAEDEADYYCKSRDGSGQHLVFGGGTKLTVLG
QPKAAPSVTLFPPSSEELQANKATLVCLISDFYPGAVTVAWKADSSPVKAGVETT
TPSKQSNNKYAASSYLSLTPEQWKSHRSYSCQVTHEGSTVEKTVAPAECS*GGGG
SGGGGSGGGGS*TIPPHVQKSVNNDMIVTDNNGAVKFPQLCKFCD
VRFSTCDNQKSCMSNCSITSICEKPQEVCVAVWRKNDENITLE
TVCHDPKLPYHDFILEDAASPKCIMKEKKKPGETFFMCSCSSD
ECNDNIIFSEEYNTSNPD

Figure 47

Clivatuzumab -TGFβRII fusion protein at LC constant region

Amino acid sequence of Clivatuzumab heavy chain:

QVQLQQSGAEVKKFGASVKVSCEASGYTFPSYVLHWVKQAPGQGLEWIGYINP
YNDGTQTNKKFKGKATLTRDTSINTAYMELSRLRSDDTAVYYCARGFGGSYGFA
YNGQGTLVTVSSASTKGPSVFPLAPSSKSTSGGTAALGCLVKDYFPEPVTVSWNS
GALTSGVNTFPAVLQSSGLYSLSSVVTVPSSSLGTQTYICNVNHKPSNTKVDKRV
EPKSCDKTHTCPPCPAPELLGGPSVFLFPPKPKDTLNISRTPEVTCVVVDVSHEDP
EVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVNHEAL
HNHYTQKSLSLSPGK

Amino acid sequence of Clivatuzumab light chain fusion protein:

DIQLTQSPSSLSASVGDRVTMTCSASSSVSSSYLYWYQQKPGKAPKLWIYSTSNL
ASGVPARFSGSGSGTDFTLTISSLQPEDSASYFCHQWNRYPYTFGGGTRLEIKRT
VAAPSVFIFPPSDEQLKSGTASVVCLLNNFYEAKVQWKVDNALQSGNSQESVTE
QDSKDSTYSLSSTLTLSPRKADYEKHKVYACEVTHQGLSSPVTKSFNRGEC*GGGG*
*SGGGGSGGGGS*TIPPHVQKSVNNDMIVTDNNGAVKFPQLCKFCD
VRFSTCDNQKSCMSNCSITSICEKPQEVCVAVWRKNDENITLE
TVCHDPKLPYHDFILEDAASPKCIMKEKKKPGETFFMCSCSSD
ECNDNIIFSEEYNTSNPD

Figure 48

Pritumumab-TGFβRII fusion protein at LC constant region

Amino acid sequence of Pritumumab heavy chain:

EVQLLESGGDLVQPGGSLRLSCAASGFTFSNYAMSWVRQAPGKGLEWVSAITP
SGGSTNYADSVKGRFTISRDNSQNTLYLQMNSLRVEDTAVYICGRVPYRSTWYP
LYWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMH
EALHNHYTQKSLSLSPGK

Amino acid sequence of Pritumumab light chain fusion protein:

DIQMTQSPSSLSASVGDRVTITCRASQDISNYLAWFQQKPGKAPKSLIYAASSLH
SKVPTQFSGSGSGTDFTLTISSLQPEDFATYYCLQYSTYPITFGGGTKVEIKRTVAA
PSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC*GGGGSGG
GGSGGGGS*TIPPHVQKSVNNDMIVTDNNGAVKFPQLCKFCDVRF
STCDNQKSCMSNCSITSICEKPQEVCVAVWRKNDENITLETVC
HDPKLPYHDFILEDAASPKCIMKEKKKPGETFFMCSCSSDECN
DNIIFSEEYNTSNPD

Figure 49

Cantuzumab HC-4-1BB and LC-TGFβRII fusion protein

Amino acid sequence of heavy chain-4-1BB fusion protein:

QVQLVQSGAEVKKPGETVKISCKASDYTFTYYGMNWVKQAPGQGLKWMGWI
DTTTGEPTYAQKFQGRIAFSLETSASTAYLQIKSLKSEDTATYFCARRGPYNWYFD
VWGQGTTVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMH
EALHNHYTQKSLSLSPGK*GGGGSGGGGSGGGGSACPWAVSGARASPGS
AASPRLREGPELSPDDPAGLLDLRQGMFAQLVAQNVLLID
GPLSWYSDPGLAGVSLTGGLSYKEDTKELVVAKAGVYYVFFQL
ELRRVVAGEGSGSVSLALHLQPLRSAAGAAALALTVDLPPAS
SEARNSAFGFQGRLLHLSAGQRLGVHLHTEARARHAWQLT
QGATVLGLFRVTPEIPAGLPSPRSE*

Amino acid sequence of Cantuzumab light chain fusion protein:

DIVMTQSPLSVPVTPGEPVSISCRSSKSLLHSNGNTYLYWFLQRPGQSPQLLIYR
MSNLVSGVPDRFSGSGSGTAFTLRISRVEAEDVGVYYCLQHLEYPFTFGPGTKLE
LKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC
*GGGGSGGGGSGGGGS***TIPPHVQKSVNNDMIVTDNNGAVKFPQLCK
FCDVRFSTCDNQKSCMSNCSITSICEKPQEVCVAVWRKNDENI
TLETVCHDPKLPYHDFILEDAASPKCIMKEKKKPGETFFMCSC
SSDECNDNIIFSEEYNTSNPD**

Figure 50

Cixutumumab HC-4-1BB and LC-TGFβRII fusion protein

Amino acid sequence of heavy chain-4-1BB fusion protein:

EVQLVQSGAEVKKPGSSVKVSCKASGGTFSSYAISWVRQAPGQGLEWMGGIIPI
FGTANYAQKFQGRVTITADKSTSTAYMELSSLRSEDTAVYYCARAPLRFLEWSTQ
DHYYYYMDVWGKGTTVTVSSASTKGPSVFPLAPSSKSTSGGTAALGCLVKDYF
PEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQGN
VFSCSVMHEALHNHYTQKSLSLSPGK*GGGGSGGGGSGGGGSACPWAVSG
ARASPGSAASPRLREGPELSPDDPAGLLDLRQGMFAQLVA
QNVLLIDGPLSWYSDPGLAGVSLTGGLSYKEDTKELVVAKAG
VYYVFFQLELRRVVAGEGSGSVSLALHLQPLRSAAGAAALAL
TVDLPPASSEARNSAFGFQGRLLHLSAGQRLGVHLHTEARA
RHAWQLTQGATVLGLFRVTPEIPAGLPSPRSE*

Amino acid sequence of Cixutumumab light chain fusion protein:

SSELTQDPAVSVALGQTVRITCQGDSLRSYYATWYQQKPGQAPILVIYGENKRPS
GIPDRFSGSSSGNTASLTITGAQAEDEADYYCKSRDGSGQHLVFGGGTKLTVLG
QPKAAPSVTLFPPSSEELQANKATLVCLISDFYPGAVTVAWKADSSPVKAGVETT
TPSKQSNNKYAASSYLSLTPEQWKSHRSYSCQVTHEGSTVEKTVAPAECS*GGGG
SGGGGSGGGGS***TIPPHVQKSVNNDMIVTDNNGAVKFPQLCKFCD
VRFSTCDNQKSCMSNCSITSICEKPQEVCVAVWRKNDENITLE
TVCHDPKLPYHDFILEDAASPKCIMKEKKKPGETFFMCSCSSD
ECNDNIIFSEEYNTSNPD**

Figure 51

Clivatuzumab HC-4-1BB and LC-TGFβRII fusion protein

Amino acid sequence of heavy chain -4-1BB fusion protein

QVQLQQSGAEVKKFGASVKVSCEASGYTFPSYVLHWVKQAPGQGLEWIGYINP
YNDGTQTNKKFKGKATLTRDTSINTAYMELSRLRSDDTAVYYCARGFGGSYGFA
YNGQGTLVTVSSASTKGPSVFPLAPSSKSTSGGTAALGCLVKDYFPEPVTVSWNS
GALTSGVNTFPAVLQSSGLYSLSSVVTVPSSSLGTQTYICNVNHKPSNTKVDKRV
EPKSCDKTHTCPPCPAPELLGGPSVFLFPPKPKDTLNISRTPEVTCVVVDVSHEDP
EVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVNHEAL
HNHYTQKSLSLSPGK*GGGGSGGGGSGGGGSACPWAVSGARASPGSAA
SPRLREGPELSPDDPAGLLDLRQGMFAQLVAQNVLLIDGPL
SWYSDPGLAGVSLTGGLSYKEDTKELVVAKAGVYYVFFQLELR
RVVAGEGSGSVSLALHLQPLRSAAGAAALALTVDLPPASSEA
RNSAFGFQGRLLHLSAGQRLGVHLHTEARARHAWQLTQG
ATVLGLFRVTPEIPAGLPSPRSE*

Amino acid sequence of Clivatuzumab light chain fusion protein:

DIQLTQSPSSLSASVGDRVTMTCSASSSVSSSYLYWYQQKPGKAPKLWIYSTSNL
ASGVPARFSGSGSGTDFTLTISSLQPEDSASYFCHQWNRYPYTFGGGTRLEIKRT
VAAPSVFIFPPSDEQLKSGTASVVCLLNNFYEAKVQWKVDNALQSGNSQESVTE
QDSKDSTYSLSSTLTLSPRKADYEKHKVYACEVTHQGLSSPVTKSFNRGEC*GGGG
SGGGGSGGGGS***TIPPHVQKSVNNDMIVTDNNGAVKFPQLCKFCD
VRFSTCDNQKSCMSNCSITSICEKPQEVCVAVWRKNDENITLE
TVCHDPKLPYHDFILEDAASPKCIMKEKKKPGETFFMCSCSSD
ECNDNIIFSEEYNTSNPD***

Figure 52

Pritumumab HC-4-1BB and LC-TGFβRII fusion protein

Amino acid sequence of heavy chain-4-1BB fusion protein:

EVQLLESGGDLVQPGGSLRLSCAASGFTFSNYAMSWVRQAPGKGLEWVSAITP
SGGSTNYADSVKGRFTISRDNSQNTLYLQMNSLRVEDTAVYICGRVPYRSTWYP
LYWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMH
EALHNHYTQKSLSLSPGK*GGGGSGGGGSGGGGS*ACPWAVSGARASPGS
AASPRLREGPELSPDDPAGLLDLRQGMFAQLVAQNVLLID
GPLSWYSDPGLAGVSLTGGLSYKEDTKELVVAKAGVYYVFFQL
ELRRVVAGEGSGSVSLALHLQPLRSAAGAAALALTVDLPPAS
SEARNSAFGFQGRLLHLSAGQRLGVHLHTEARARHAWQLT
QGATVLGLFRVTPEIPAGLPSPRSE

Amino acid sequence of Pritumumab light chain fusion protein:

DIQMTQSPSSLSASVGDRVTITCRASQDISNYLAWFQQKPGKAPKSLIYAASSLH
SKVPTQFSGSGSGTDFTLTISSLQPEDFATYYCLQYSTYPITFGGGTKVEIKRTVAA
PSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC*GGGGSGG
GGSGGGGS***TIPPHVQKSVNNDMIVTDNNGAVKFPQLCKFCDVRF
STCDNQKSCMSNCSITSICEKPQEVCVAVWRKNDENITLETVC
HDPKLPYHDFILEDAASPKCIMKEKKKPGETFFMCSCSSDECN
DNIIFSEEYNTSNPD**

Figure 53

Cantuzumab - HC-PD1 and LC-TGFβRII fusion protein

Amino acid sequence of heavy chain-PD1 fusion protein:

QVQLVQSGAEVKKPGETVKISCKASDYTFTYYGMNWVKQAPGQGLKWMGWI
DTTTGEPTYAQKFQGRIAFSLETSASTAYLQIKSLKSEDTATYFCARRGPYNWYFD
VWGQGTTVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMH
EALHNHYTQKSLSLSPGKGGGGSGGGGSGGGGS*PGWFLDSPDRPWNPPT
FSPALLVVTEGDNATFTCSFSNTSESFVLNWYRMSPSNQTDKLAAFPE
DRSQPGQDCRFRVTQLPNGRDFHMSVVRARRNDSGTYLCGAISLA
PKAQIKESLRAELRVTERRAEVPTAHPSPSPRPAGQFQTLV*

Amino acid sequence of Cantuzumab light chain fusion protein:

DIVMTQSPLSVPVTPGEPVSISCRSSKSLLHSNGNTYLYWFLQRPGQSPQLLIYR
MSNLVSGVPDRFSGSGSGTAFTLRISRVEAEDVGVYYCLQHLEYPFTFGPGTKLE
LKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC
*GGGGSGGGGSGGGGS***TIPPHVQKSVNNDMIVTDNNGAVKFPQLCK
FCDVRFSTCDNQKSCMSNCSITSICEKPQEVCVAVWRKNDENI
TLETVCHDPKLPYHDFILEDAASPKCIMKEKKKPGETFFMCSC
SSDECNDNIIFSEEYNTSNPD**

Cixutumumab HC-PD1 and LC-TGFβRII fusion protein

Amino acid sequence of heavy chain-PD1 fusion protein:

EVQLVQSGAEVKKPGSSVKVSCKASGGTFSSYAISWVRQAPGQGLEWMGGIIPI
FGTANYAQKFQGRVTITADKSTSTAYMELSSLRSEDTAVYYCARAPLRFLEWSTQ
DHYYYYYMDVWGKGTTVTVSSASTKGPSVFPLAPSSKSTSGGTAALGCLVKDYF
PEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQGN
VFSCSVMHEALHNHYTQKSLSLSPGK*GGGGSGGGGSGGGGSPGWFLDSPD
RPWNPPTFSPALLVVTEGDNATFTCSFSNTSESFVLNWYRMSPSNQT
DKLAAFPEDRSQPGQDCRFRVTQLPNGRDFHMSVVRARRNDSGTY
LCGAISLAPKAQIKESLRAELRVTERRAEVPTAHPSPSPRPAGQFQTL
V*

Amino acid sequence of Cixutumumab light chain fusion protein:

SSELTQDPAVSVALGQTVRITCQGDSLRSYYATWYQQKPGQAPILVIYGENKRPS
GIPDRFSGSSSGNTASLTITGAQAEDEADYYCKSRDGSGQHLVFGGGTKLTVLG
QPKAAPSVTLFPPSSEELQANKATLVCLISDFYPGAVTVAWKADSSPVKAGVETT
TPSKQSNNKYAASSYLSLTPEQWKSHRSYSCQVTHEGSTVEKTVAPAECS*GGGG
SGGGGSGGGGS***TIPPHVQKSVNNDMIVTDNNGAVKFPQLCKFCD
VRFSTCDNQKSCMSNCSITSICEKPQEVCVAVWRKNDENITLE
TVCHDPKLPYHDFILEDAASPKCIMKEKKKPGETFFMCSCSSD
ECNDNIIFSEEYNTSNPD**

Clivatuzumab HC-PD1 and LC-TGFβRII-fusion protein

Amino acid Amino acid sequence of heavy chain-PD1 fusion protein:

QVQLQQSGAEVKKFGASVKVSCEASGYTFPSYVLHWVKQAPGQGLEWIGYINP
YNDGTQTNKKFKGKATLTRDTSINTAYMELSRLRSDDTAVYYCARGFGGSYGFA
YNGQGTLVTVSSASTKGPSVFPLAPSSKSTSGGTAALGCLVKDYFPEPVTVSWNS
GALTSGVNTFPAVLQSSGLYSLSSVVTVPSSSLGTQTYICNVNHKPSNTKVDKRV
EPKSCDKTHTCPPCPAPELLGGPSVFLFPPKPKDTLNISRTPEVTCVVVDVSHEDP
EVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVNHEAL
HNHYTQKSLSLSPGK*GGGGSGGGGSGGGGSPGWFLDSPDRPWNPPTFSP
ALLVVTEGDNATFTCSFSNTSESFVLNWYRMSPSNQTDKLAAFPEDRS
QPGQDCRFRVTQLPNGRDFHMSVVRARRNDSGTYLCGAISLAPKA
QIKESLRAELRVTERRAEVPTAHPSPSPRPAGQFQTLV*

Amino acid sequence of Clivatuzumab light chain fusion protein:

DIQLTQSPSSLSASVGDRVTMTCSASSSVSSSYLYWYQQKPGKAPKLWIYSTSNL
ASGVPARFSGSGSGTDFTLTISSLQPEDSASYFCHQWNRYPYTFGGGTRLEIKRT
VAAPSVFIFPPSDEQLKSGTASVVCLLNNFYEAKVQWKVDNALQSGNSQESVTE
QDSKDSTYSLSSTLTLSPRKADYEKHKVYACEVTHQGLSSPVTKSFNRGEC*GGGG
SGGGGSGGGGS***TIPPHVQKSVNNDMIVTDNNGAVKFPQLCKFCD
VRFSTCDNQKSCMSNCSITSICEKPQEVCVAVWRKNDENITLE
TVCHDPKLPYHDFILEDAASPKCIMKEKKKPGETFFMCSCSSD
ECNDNIIFSEEYNTSNPD***

Figure 56

Pritumumab HC-PD1 and LC-TGFβRII fusion protein

Amino acid Amino acid sequence of heavy chain-PD1 fusion protein:

EVQLLESGGDLVQPGGSLRLSCAASGFTFSNYAMSWVRQAPGKGLEWVSAITP
SGGSTNYADSVKGRFTISRDNSQNTLYLQMNSLRVEDTAVYICGRVPYRSTWYP
LYWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMH
EALHNHYTQKSLSLSPGK*GGGGSGGGGSGGGGSPGWFLDSPDRPWNPPT*
*FSPALLVVTEGDNATFTCSFSNTSESFVLNWYRMSPSNQTDKLAAFPE*
*DRSQPGQDCRFRVTQLPNGRDFHMSVVRARRNDSGTYLCGAISLA*
*PKAQIKESLRAELRVTERRAEVPTAHPSPSPRPAGQFQTLV*

Amino acid sequence of Pritumumab light chain fusion protein:.

DIQMTQSPSSLSASVGDRVTITCRASQDISNYLAWFQQKPGKAPKSLIYAASSLH
SKVPTQFSGSGSGTDFTLTISSLQPEDFATYYCLQYSTYPITFGGGTKVEIKRTVAA
PSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC*GGGGSGG*
*GGSGGGGS*TIPPHVQKSVNNDMIVTDNNGAVKFPQLCKFCDVRF
STCDNQKSCMSNCSITSICEKPQEVCVAVWRKNDENITLETVC
HDPKLPYHDFILEDAASPKCIMKEKKKPGETFFMCSCSSDECN
DNIIFSEEYNTSNPD

Figure 57

Cantuzumab HC-TGFβRII-4-1BB fusion protein

Amino acid sequence of heavy chain-TGFβRII-4-1BB fusion protein:

QVQLVQSGAEVKKPGETVKISCKASDYTFTYYGMNWVKQAPGQGLKWMGWI
DTTTGEPTYAQKFQGRIAFSLETSASTAYLQIKSLKSEDTATYFCARRGPYNWYFD
VWGQGTTVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMH
EALHNHYTQKSLSLSPGK*GGGGSGGGGSGGGGS***TIPPHVQKSVNNDMIV
TDNNGAVKFPQLCKFCDVRFSTCDNQKSCMSNCSITSICEKPQ
EVCVAVWRKNDENITLETVCHDPKLPYHDFILEDAASPKCIMK
EKKKPGETFFMCSCSSDECNDNIIFSEEYNTSNPDepkscdk***AC
PWAVSGARASPGSAASPRLREGPELSPDDPAGLLDLRQGMF
AQLVAQNVLLIDGPLSWYSDPGLAGVSLTGGLSYKEDTKELV
VAKAGVYYVFFQLELRRWAGEGSGSVSLALHLQPLRSAAGA
AALALTVDLPPASSEARNSAFGFQGRLLHLSAGQRLGVHLH
TEARARHAWQLTQGATVLGLFRVTPEIPAGLPSPRSE*

Amino acid sequence of light chain

DIVMTQSPLSVPVTPGEPVSISCRSSKSLLHSNGNTYLYWFLQRPGQSPQLLIYR
MSNLVSGVPDRFSGSGSGTAFTLRISRVEAEDVGVYYCLQHLEYPFTFGPGTKLE
LKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC

Figure 58

Cixutumumab HC-TGFβRII-4-1BB fusion protein

Amino acid sequence of heavy chain-TGFβRII-4-1BB fusion protein:

EVQLVQSGAEVKKPGSSVKVSCKASGGTFSSYAISWVRQAPGQGLEWMGGIIPI
FGTANYAQKFQGRVTITADKSTSTAYMELSSLRSEDTAVYYCARAPLRFLEWSTQ
DHYYYYYMDVWGKGTTVTVSSASTKGPSVFPLAPSSKSTSGGTAALGCLVKDYF
PEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQGN
VFSCSVMHEALHNHYTQKSLSLSPGK*GGGGSGGGGSGGGGS***TIPPHVQKS
VNNDMIVTDNNGAVKFPQLCKFCDVRFSTCDNQKSCMSNCSI
TSICEKPQEVCVAVWRKNDENITLETVCHDPKLPYHDFILEDAA
SPKCIMKEKKKPGETFFMCSCSSDECNDNIIFSEEYNTSNPD***ep
kscdk****ACPWAVSGARASPGSAASPRLREGPELSPDDPAGLLD
LRQGMFAQLVAQNVLLIDGPLSWYSDPGLAGVSLTGGLSYK
EDTKELVVAKAGVYYVFFQLELRRVVAGEGSGSVSLALHLQP
LRSAAGAAALALTVDLPPASSEARNSAFGFQGRLLHLSAGQ
RLGVHLHTEARARHAWQLTQGATVLGLFRVTPEIPAGLPSP
RSE*

Amino acid sequence of light chain:

SSELTQDPAVSVALGQTVRITCQGDSLRSYYATWYQQKPGQAPILVIYGENKRPS
GIPDRFSGSSSGNTASLTITGAQAEDEADYYCKSRDGSGQHLVFGGGTKLTVLG
QPKAAPSVTLFPPSSEELQANKATLVCLISDFYPGAVTVAWKADSSPVKAGVETT
TPSKQSNNKYAASSYLSLTPEQWKSHRSYSCQVTHEGSTVEKTVAPAECS

Figure 59

Clivatuzumab HC-TGFβRII-4-1BB fusion protein

Amino acid sequence of heavy chain-TGFβRII-4-1BB fusion protein:

QVQLQQSGAEVKKFGASVKVSCEASGYTFPSYVLHWVKQAPGQGLEWIGYINP
YNDGTQTNKKFKGKATLTRDTSINTAYMELSRLRSDDTAVYYCARGFGGSYGFA
YNGQGTLVTVSSASTKGPSVFPLAPSSKSTSGGTAALGCLVKDYFPEPVTVSWNS
GALTSGVNTFPAVLQSSGLYSLSSVVTVPSSSLGTQTYICNVNHKPSNTKVDKRV
EPKSCDKTHTCPPCPAPELLGGPSVFLFPPKPKDTLNISRTPEVTCVVVDVSHEDP
EVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVNHEAL
HNHYTQKSLSLSPGK*GGGGSGGGGSGGGGS***TIPPHVQKSVNNDMIVTD
NNGAVKFPQLCKFCDVRFSTCDNQKSCMSNCSITSICEKPQEV
CVAVWRKNDENITLETVCHDPKLPYHDFILEDAASPKCIMKEK
KKPGETFFMCSCSSDECNDNIIFSEEYNTSNPD**epkscdk**ACPW*
*AVSGARASPGSAASPRLREGPELSPDDPAGLLDLRQGMFAQ*
*LVAQNVLLIDGPLSWYSDPGLAGVSLTGGLSYKEDTKELVVA*
*KAGVYYVFFQLELRRVVAGEGSGSVSLALHLQPLRSAAGAAA*
*LALTVDLPPASSEARNSAFGFQGRLLHLSAGQRLGVHLHTE*
*ARARHAWQLTQGATVLGLFRVTPEIPAGLPSPRSE*

Amino acid sequence of light chain:

DIQLTQSPSSLSASVGDRVTMTCSASSSVSSSYLYWYQQKPGKAPKLWIYSTSNL
ASGVPARFSGSGSGTDFTLTISSLQPEDSASYFCHQWNRYPYTFGGGTRLEIKRT
VAAPSVFIFPPSDEQLKSGTASVVCLLNNFYEAKVQWKVDNALQSGNSQESVTE
QDSKDSTYSLSSTLTLSPRKADYEKHKVYACEVTHQGLSSPVTKSFNRGEC

Figure 60

Pritumumab HC-TGFβRII-4-1BB fusion protein

Amino acid sequence of heavy chain-TGFβRII-4-1BB fusion protein:

EVQLLESGGDLVQPGGSLRLSCAASGFTFSNYAMSWVRQAPGKGLEWVSAITP
SGGSTNYADSVKGRFTISRDNSQNTLYLQMNSLRVEDTAVYICGRVPYRSTWYP
LYWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMH
EALHNHYTQKSLSLSPGK*GGGGSGGGGSGGGGS***TIPPHVQKSVNNDMIV
TDNNGAVKFPQLCKFCDVRFSTCDNQKSCMSNCSITSICEKPQ
EVCVAVWRKNDENITLETVCHDPKLPYHDFILEDAASPKCIMK
EKKKPGETFFMCSCSSDECNDNIIFSEEYNTSNPD*epkscdkAC
PWAVSGARASPGSAASPRLREGPELSPDDPAGLLDLRQGMF
AQLVAQNVLLIDGPLSWYSDPGLAGVSLTGGLSYKEDTKELV
VAKAGVYYVFFQLELRRVVAGEGSGSVSLALHLQPLRSAAGA
AALALTVDLPPASSEARNSAFGFQGRLLHLSAGQRLGVHLH
TEARARHAWQLTQGATVLGLFRVTPEIPAGLPSPRSE*

Amino acid sequence of light chain:

DIQMTQSPSSLSASVGDRVTITCRASQDISNYLAWFQQKPGKAPKSLIYAASSLH
SKVPTQFSGSGSGTDFTLTISSLQPEDFATYYCLQYSTYPITFGGGTKVEIKRTVAA
PSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

Figure 61

Cantuzumab HC-TGFβRII-PD1 fusion protein

Amino acid sequence of heavy chain-TGFβRII-PD1 fusion protein:

QVQLVQSGAEVKKPGETVKISCKASDYTFTYYGMNWVKQAPGQGLKWMGWI
DTTTGEPTYAQKFQGRIAFSLETSASTAYLQIKSLKSEDTATYFCARRGPYNWYFD
VWGQGTTVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMH
EALHNHYTQKSLSLSPGK*GGGGSGGGGSGGGGS***TIPPHVQKSVNNDMIV
TDNNGAVKFPQLCKFCDVRFSTCDNQKSCMSNCSITSICEKPQ
EVCVAVWRKNDENITLETVCHDPKLPYHDFILEDAASPKCIMK
EKKKPGETFFMCSCSSDECNDNIIFSEEYNTSNPD*epkscdkPG
WFLDSPDRPWNPPTFSPALLVVTEGDNATFTCSFSNTSESFVLNWYR
MSPSNQTDKLAAFPEDRSQPGQDCRFRVTQLPNGRDFHMSVVRAR
RNDSGTYLCGAISLAPKAQIKESLRAELRVTERRAEVPTAHPSPSPRP
AGQFQTLV*

Amino acid sequence of light chain:

DIVMTQSPLSVPVTPGEPVSISCRSSKSLLHSNGNTYLYWFLQRPGQSPQLLIYR
MSNLVSGVPDRFSGSGSGTAFTLRISRVEAEDVGVYYCLQHLEYPFTFGPGTKLE
LKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC

Figure 62

Cixutumumab HC-TGFβRII-PD1 fusion protein

Amino acid sequence of heavy chain-TGFβRII-PD1 fusion protein:

EVQLVQSGAEVKKPGSSVKVSCKASGGTFSSYAISWVRQAPGQGLEWMGGIIPI
FGTANYAQKFQGRVTITADKSTSTAYMELSSLRSEDTAVYYCARAPLRFLEWSTQ
DHYYYYMDVWGKGTTVTVSSASTKGPSVFPLAPSSKSTSGGTAALGCLVKDYF
PEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQGN
VFSCSVMHEALHNHYTQKSLSLSPGK*GGGGSGGGGSGGGGS***TIPPHVQKS
VNNDMIVTDNNGAVKFPQLCKFCDVRFSTCDNQKSCMSNCSI
TSICEKPQEVCVAVWRKNDENITLETVCHDPKLPYHDFILEDAA
SPKCIMKEKKKPGETFFMCSCSSDECNDNIIFSEEYNTSNPD**ep
kscdk*PGWFLDSPDRPWNPPTFSPALLVVTEGDNATFTCSFSNTSESF
VLNWYRMSPSNQTDKLAAFPEDRSQPGQDCRFRVTQLPNGRDFHM
SVVRARRNDSGTYLCGAISLAPKAQIKESLRAELRVTERRAEVPTAH
PSPSPRPAGQFQTLV*

Amino acid sequence of light chain:

SSELTQDPAVSVALGQTVRITCQGDSLRSYYATWYQQKPGQAPILVIYGENKRPS
GIPDRFSGSSSGNTASLTITGAQAEDEADYYCKSRDGSGQHLVFGGGTKLTVLG
QPKAAPSVTLFPPSSEELQANKATLVCLISDFYPGAVTVAWKADSSPVKAGVETT
TPSKQSNNKYAASSYLSLTPEQWKSHRSYSCQVTHEGSTVEKTVAPAECS

Figure 63

Clivatuzumab HC-TGFβRII-PD1 fusion protein

Amino acid sequence of heavy chain-TGFβRII-PD1 fusion protein:

QVQLQQSGAEVKKFGASVKVSCEASGYTFPSYVLHWVKQAPGQGLEWIGYINP
YNDGTQTNKKFKGKATLTRDTSINTAYMELSRLRSDDTAVYYCARGFGGSYGFA
YNGQGTLVTVSSASTKGPSVFPLAPSSKSTSGGTAALGCLVKDYFPEPVTVSWNS
GALTSGVNTFPAVLQSSGLYSLSSVVTVPSSSLGTQTYICNVNHKPSNTKVDKRV
EPKSCDKTHTCPPCPAPELLGGPSVFLFPPKPKDTLNISRTPEVTCVVVDVSHEDP
EVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVNHEAL
HNHYTQKSLSLSPGK*GGGGSGGGGSGGGGS***TIPPHVQKSVNNDMIVTD
NNGAVKFPQLCKFCDVRFSTCDNQKSCMSNCSITSICEKPQEV
CVAVWRKNDENITLETVCHDPKLPYHDFILEDAASPKCIMKEK
KKPGETFFMCSCSSDECNDNIIFSEEYNTSNPD*epkscdkPGWFL
DSPDRPWNPPTFSPALLVVTEGDNATFTCSFSNTSESFVLNWYRMSPS
NQTDKLAAFPEDRSQPGQDCRFRVTQLPNGRDFHMSVVRARRND
SGTYLCGAISLAPKAQIKESLRAELRVTERRAEVPTAHPSPSPRPAGQ
FQTLV*

Amino acid sequence of light chain:

DIQLTQSPSSLSASVGDRVTMTCSASSSVSSSYLYWYQQKPGKAPKLWIYSTSNL
ASGVPARFSGSGSGTDFTLTISSLQPEDSASYFCHQWNRYPYTFGGGTRLEIKRT
VAAPSVFIFPPSDEQLKSGTASVVCLLNNFYEAKVQWKVDNALQSGNSQESVTE
QDSKDSTYSLSSTLTLSPRKADYEKHKVYACEVTHQGLSSPVTKSFNRGEC

Figure 64

Pritumumab HC-TGFβRII-PD1 fusion protein

Amino acid sequence of heavy chain-TGFβRII-PD1 fusion protein:

EVQLLESGGDLVQPGGSLRLSCAASGFTFSNYAMSWVRQAPGKGLEWVSAITP
SGGSTNYADSVKGRFTISRDNSQNTLYLQMNSLRVEDTAVYICGRVPYRSTWYP
LYWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMH
EALHNHYTQKSLSLSPGK*GGGGSGGGGSGGGGS***TIPPHVQKSVNNDMIV
TDNNGAVKFPQLCKFCDVRFSTCDNQKSCMSNCSITSICEKPQ
EVCVAVWRKNDENITLETVCHDPKLPYHDFILEDAASPKCIMK
EKKKPGETFFMCSCSSDECNDNIIFSEEYNTSNPD*epkscdk**PG
WFLDSPDRPWNPPTFSPALLVVTEGDNATFTCSFSNTSESFVLNWYR
MSPSNQTDKLAAFPEDRSQPGQDCRFRVTQLPNGRDFHMSVVRAR
RNDSGTYLCGAISLAPKAQIKESLRAELRVTERRAEVPTAHPSPSPRP
AGQFQTLV*

Amino acid sequence of light chain:

DIQMTQSPSSLSASVGDRVTITCRASQDISNYLAWFQQKPGKAPKSLIYAASSLH
SKVPTQFSGSGSGTDFTLTISSLQPEDFATYYCLQYSTYPITFGGGTKVEIKRTVAA
PSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

Figure 65

SEQUENCE LISTING

```
<160> NUMBER OF SEQ ID NOS: 39

<210> SEQ ID NO 1
<211> LENGTH: 449
<212> TYPE: PRT
<213> ORGANISM: Artificial Sequence
<220> FEATURE:
<223> OTHER INFORMATION: Synthetic construct

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 2
<211> LENGTH: 214
<212> TYPE: PRT
<213> ORGANISM: Artificial Sequence
<220> FEATURE:
<223> OTHER INFORMATION: Synthetic construct

<400> SEQUENCE: 2

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 15
<212> TYPE: PRT
<213> ORGANISM: Artificial Sequence
<220> FEATURE:
<223> OTHER INFORMATION: Synthetic construct

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 137
<212> TYPE: PRT
<213> ORGANISM: Artificial Sequence
<220> FEATURE:
<223> OTHER INFORMATION: Synthetic construct

<400> SEQUENCE: 4

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80
```

```
Asp Pro Lys Leu Pro Tyr His Asp Phe Ile Leu Glu Asp Ala Ala Ser
            85                  90                  95

Pro Lys Cys Ile Met Lys Glu Lys Lys Pro Gly Glu Thr Phe Phe
        100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp
        130                 135

<210> SEQ ID NO 5
<211> LENGTH: 448
<212> TYPE: PRT
<213> ORGANISM: Artificial Sequence
<220> FEATURE:
<223> OTHER INFORMATION: Synthetic Construct

<400> SEQUENCE: 5

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 6
<211> LENGTH: 214
<212> TYPE: PRT
<213> ORGANISM: Artificial Sequence
<220> FEATURE:
<223> OTHER INFORMATION: Synthetic construct

<400> SEQUENCE: 6

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 7
<211> LENGTH: 447
<212> TYPE: PRT
<213> ORGANISM: Artificial Sequence
<220> FEATURE:
<223> OTHER INFORMATION: Synthetic construct

<400> SEQUENCE: 7

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

```
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
            405                 410                 415
Arg Trp Gln Gln Gly Asn Val Phe Ser Cys Ser Val Met His Glu Ala
        420                 425                 430
Leu His Asn His Tyr Thr Gln Lys Ser Leu Ser Leu Ser Pro Gly
        435                 440                 445
```

<210> SEQ ID NO 8
<211> LENGTH: 215
<212> TYPE: PRT
<213> ORGANISM: Artificial Sequence
<220> FEATURE:
<223> OTHER INFORMATION: Synthetic construct

<400> SEQUENCE: 8

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Gly Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Phe Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Trp Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215
```

<210> SEQ ID NO 9
<211> LENGTH: 205
<212> TYPE: PRT
<213> ORGANISM: Artificial Sequence
<220> FEATURE:
<223> OTHER INFORMATION: Synthetic construct

<400> SEQUENCE: 9

```
Ala Cys Pro Trp Ala Val Ser Gly Ala Arg Ala Ser Pro Gly Ser Ala
1               5                   10                  15
```

```
            1               5                  10                 15
         Ala Ser Pro Arg Leu Arg Glu Gly Pro Glu Leu Ser Pro Asp Asp Pro
                         20                 25                 30

Ala Gly Leu Leu Asp Leu Arg Gln Gly Met Phe Ala Gln Leu Val Ala
                         35                 40                 45

Gln Asn Val Leu Leu Ile Asp Gly Pro Leu Ser Trp Tyr Ser Asp Pro
                         50                 55                 60

Gly Leu Ala Gly Val Ser Leu Thr Gly Leu Ser Tyr Lys Glu Asp
         65                  70                 75                 80

Thr Lys Glu Leu Val Val Ala Lys Ala Gly Val Tyr Tyr Val Phe Phe
                              85                 90                 95

Gln Leu Glu Leu Arg Arg Val Val Ala Gly Glu Gly Ser Gly Ser Val
                         100                105                110

Ser Leu Ala Leu His Leu Gln Pro Leu Arg Ser Ala Ala Gly Ala Ala
                         115                120                125

Ala Leu Ala Leu Thr Val Asp Leu Pro Pro Ala Ser Ser Glu Ala Arg
         130                 135                140

Asn Ser Ala Phe Gly Phe Gln Gly Arg Leu Leu His Leu Ser Ala Gly
         145                 150                155                160

Gln Arg Leu Gly Val His Leu His Thr Glu Ala Arg Ala Arg His Ala
                             165                170                175

Trp Gln Leu Thr Gln Gly Ala Thr Val Leu Gly Leu Phe Arg Val Thr
                         180                185                190

Pro Glu Ile Pro Ala Gly Leu Pro Ser Pro Arg Ser Glu
                         195                200                205

<210> SEQ ID NO 10
<211> LENGTH: 150
<212> TYPE: PRT
<213> ORGANISM: Artificial Sequence
<220> FEATURE:
<223> OTHER INFORMATION: Synthetic construct

<400> SEQUENCE: 10

Pro Gly Trp Phe Leu Asp Ser Pro Asp Arg Pro Trp Asn Pro Pro Thr
         1               5                  10                 15

Phe Ser Pro Ala Leu Leu Val Val Thr Glu Gly Asp Asn Ala Thr Phe
                         20                 25                 30

Thr Cys Ser Phe Ser Asn Thr Ser Glu Ser Phe Val Leu Asn Trp Tyr
                         35                 40                 45

Arg Met Ser Pro Ser Asn Gln Thr Asp Lys Leu Ala Ala Phe Pro Glu
                         50                 55                 60

Asp Arg Ser Gln Pro Gly Gln Asp Cys Arg Phe Arg Val Thr Gln Leu
         65                  70                 75                 80

Pro Asn Gly Arg Asp Phe His Met Ser Val Val Arg Ala Arg Arg Asn
                             85                 90                 95

Asp Ser Gly Thr Tyr Leu Cys Gly Ala Ile Ser Leu Ala Pro Lys Ala
                         100                105                110

Gln Ile Lys Glu Ser Leu Arg Ala Glu Leu Arg Val Thr Glu Arg Arg
                         115                120                125

Ala Glu Val Pro Thr Ala His Pro Ser Pro Ser Pro Arg Pro Ala Gly
                         130                135                140

Gln Phe Gln Thr Leu Val
         145                 150
```

```
<210> SEQ ID NO 11
<211> LENGTH: 7
<212> TYPE: PRT
<213> ORGANISM: Artificial Sequence
<220> FEATURE:
<223> OTHER INFORMATION: Synthetic construct

<400> SEQUENCE: 11

Glu Pro Lys Ser Cys Asp Lys
1               5

<210> SEQ ID NO 12
<211> LENGTH: 1032
<212> TYPE: DNA
<213> ORGANISM: Artificial Sequence
<220> FEATURE:
<223> OTHER INFORMATION: Synthetic construct

<400> SEQUENCE: 12
gctagcacca agggcccctc cgtgttccct ctggccccct ccagcaagtc cacctctggc      60
ggcaccgccg ctctgggctg cctggtcaag gactacttcc ccgagcccgt gaccgtgtcc     120
tggaactctg gcgctctgac ctccggcgtg cacaccttcc ctgccgtgct gcagtcctcc     180
ggcctgtact ccctgtcctc cgtcgtgacc gtgccctcca gctctctggg cacccagacc     240
tacatctgca acgtgaacca caagccctcc aacaccaagg tggacaagaa ggtggaaccc     300
aagtcctgcg acaagaccca cacctgtccc cctgccctg ccctgaggc ctgggaggc       360 cctagcgtgt tcctgttccc cccaaagccc aaggacaccc tgatgatctc ccggaccccc     420
gaagtgacct gcgtggtggt ggacgtgtcc cacgaggacc ctgaagtgaa gttcaattgg     480
tacgtggacg gcgtggaagt gcacaacgcc aagaccaagc cagagagga acagtacaac     540 tccacctacc gggtggtgtc cgtgctgacc gtgctgcacc aggactggct gaacggcaaa     600
gagtacaagt gcaaggtgtc caacaaggcc ctgcctgccc catcgaaaa gaccatctcc      660 aaggccaagg ccagccccg cgagcctcag gtgtacaccc tgcccccctag ccgggaagag     720 atgaccaaga accaggtgtc cctgacctgt ctggtcaagg gcttctaccc ctccgatatc     780
gccgtggaat gggagtccaa cggccagccc gagaacaact acaagaccac cccccctgtg     840
ctggactccg acggctcatt cttcctgtac tccaagctga ccgtggacaa gtcccggtgg     900
cagcagggca cgtgttctc ctgctccgtg atgcacgagg ccctgcacaa ccactacacc      960
cagaagtccc tgtccctgag cccaggcaaa ggcggaggcg gatctggcgg cggaggatct    1020
ggtggcggat cc                                                        1032

<210> SEQ ID NO 13
<211> LENGTH: 425
<212> TYPE: DNA
<213> ORGANISM: Artificial Sequence
<220> FEATURE:
<223> OTHER INFORMATION: Synthetic construct

<400> SEQUENCE: 13
ggatccacca tccccccaca cgtgcagaaa tccgtgaaca acgacatgat cgtgaccgac      60
aacaacggcg ctgtgaagtt cccccagctg tgcaagttct cgcacgtgcg gttctctacc     120
tgcgacaacc agaaatcctg catgtccaac tgctccatca cctccatctg cgagaagccc     180
caggaagtgt gcgtcgccgt ctggcggaag aacgacgaga acatcaccct ggaaaccgtg     240
tgccacgacc ccaagctgcc ctaccacgac ttcatcctgg aagatgccgc ctcccccaag     300
tgcatcatga aggaaaagaa gaagcccggc gagactttct tcatgtgcag ctgctcctcc     360
```

```
gacgagtgca acgacaacat catcttctcc gaagagtaca acacctccaa ccccgactga    420
agctt                                                                425

<210> SEQ ID NO 14
<211> LENGTH: 430
<212> TYPE: DNA
<213> ORGANISM: Artificial Sequence
<220> FEATURE:
<223> OTHER INFORMATION: Synthetic construct

<400> SEQUENCE: 14
gcggccgcca tgaacttcgg cctgcggctg atcttcctgg tgctgaccct gaagggcgtg     60
cagtgcgagg tgcagctggt ggaatccggc ggaggcctgg tccagcctgg cggatctctg    120
agactgtcct gcgccgcctc cggcttcaac atcaaggaca cctacatcca ctgggtccga    180
caggcccctg gcaagggcct ggaatgggtg gcccggatct accccaccaa cggctacacc    240
agatacgccg actccgtgaa gggccggttc accatctccg ccgacacctc caagaacacc    300
gcctacctgc agatgaactc cctgcgggcc gaggacaccg ccgtgtacta ctgctccaga    360
tggggaggcg acggcttcta cgccatggac tactggggcc agggcaccct ggtcaccgtg    420
ctccgctagc                                                           430

<210> SEQ ID NO 15
<211> LENGTH: 442
<212> TYPE: DNA
<213> ORGANISM: Artificial Sequence
<220> FEATURE:
<223> OTHER INFORMATION: Synthetic construct

<400> SEQUENCE: 15
gcggccgcca tggaatccca gacccaggtg ctgatctccc tgctgttctg ggtgtccggc     60
acctgtggcg acatccagat gacccagtcc cctccagcc tgtccgcctc tgtgggcgac    120
agagtgacca tcacctgtcg ggcctcccag gacgtgaaca ccgccgtggc ctggtatcag    180
cagaagcccg gcaaggcccc caagctgctg atctactccg cctccttcct gtactccggc    240
gtgccctccc ggttctccgg ctctagatcc ggcaccgact ttaccctgac catctccagc    300
ctgcagcccg aggacttcgc cacctactac tgccagcagc actacaccac cccccccacc    360
tttggccagg gcaccaaggt ggaaatcaag cggaccgtgg ccgctcccte cgtgttcatc    420 cccacccctcc gacgagcagc tg                                            442

<210> SEQ ID NO 16
<211> LENGTH: 1032
<212> TYPE: DNA
<213> ORGANISM: Artificial Sequence
<220> FEATURE:
<223> OTHER INFORMATION: Synthetic construct

<400> SEQUENCE: 16
gctagcacca agggcccctc cgtgtttccc ctggcccccct ccagcaagtc cacctctggc     60
ggcaccgccg ctctgggctg cctggtcaag gactacttcc ccgagcccgt gaccgtgtcc    120
tggaactctg gcgctctgac ctccggcgtg cacaccttcc ctgccgtgct gcagtcctcc    180
ggcctgtact ccctgtcctc cgtcgtgacc gtgccctcca gctctctggg cacccagacc    240
tacatctgca acgtgaacca caagccctcc aacaccaagg tggacaagcg ggtggaaccc    300
aagtcctgcg acaagaccca cacctgtccc ccctgccctg ccctgaact gctggggaggc    360
```

```
ccttccgtgt tcctgttccc cccaaagccc aaggacaccc tgatgatctc ccggacccccc    420 gaagtgacct gcgtggtggt ggacgtgtcc cacgaggacc ctgaagtgaa gttcaattgg    480
tacgtggacg gcgtggaagt gcacaacgcc aagaccaagc ccagagagga acagtacaac    540
tccacctacc gggtggtgtc cgtgctgacc gtgctgcacc aggactggct gaacggcaaa    600
gagtacaagt gcaaggtgtc caacaaggcc ctgcctgccc ccatcgaaaa gaccatctcc    660
aaggccaagg gccagccccg cgagcctcag gtgtacaccc tgcctcccag ccgggacgag    720
ctgaccaaga accaggtgtc cctgacctgt ctggtcaagg gcttctaccc ctccgatatc    780
gccgtggaat gggagtccaa cggccagccc gagaacaact acaagaccac ccccctgtg     840 ctggactccg acggctcatt cttcctgtac tccaagctga ccgtggacaa gtcccggtgg    900
cagcagggca acgtgttctc ctgctccgtg atgcacgagg ccctgcacaa ccactacacc    960
cagaagtccc tgtctctgag ccccggcaaa ggcggcggag gatctggcgg tggcggatca   1020
ggcggaggat cc                                                        1032

<210> SEQ ID NO 17
<211> LENGTH: 427
<212> TYPE: DNA
<213> ORGANISM: Artificial Sequence
<220> FEATURE:
<223> OTHER INFORMATION: Synthetic construct

<400> SEQUENCE: 17
gcggccgcca tgaacttcgg cctgcggctg atcttcctgg tgctgacccc gaagggcgtg     60
cagtgccagg tgcagctgaa gcagtccgga cctggcctgg tgcagccttc ccagtccctg    120
tccatcacct gtaccgtgtc cggcttctcc ctgaccaact acggcgtgca ctgggtccga    180
cagtccccag gcaagggcct ggaatggctg ggagtgattt ggagcggcgg caacaccgac    240
tacaacaccc ccttcacctc ccggctgtcc atcaacaagg acaactccaa gtcccaggtg    300
ttcttcaaga tgaactccct gcagtccaac gacaccgcca tctactactg cgccagagcc    360
ctgacctact atgactacga gttcgcctac tggggacagg gcaccctggt caccgtgtct    420
cgctagc                                                              427

<210> SEQ ID NO 18
<211> LENGTH: 442
<212> TYPE: DNA
<213> ORGANISM: Artificial Sequence
<220> FEATURE:
<223> OTHER INFORMATION: Synthetic construct

<400> SEQUENCE: 18
gcggccgcca tggaatccca gacccaggtg ctgatctccc tgctgttctg ggtgtccggc     60
acctgtggcg acatcctgct gacccagtcc cccgtgatcc tgtccgtgtc tcctggcgag    120
cgggtgtcct ctcctgccg ggcctcccag tccatcggca ccaacatcca ctggtatcag    180
cagcggacca acggctcccc tcggctgctg attaagtacg cctccgagtc tatctccggc    240 atccccctccc ggttctccgg ctctggctcc ggcaccgact tcaccctgtc catcaactcc    300
gtggaatccg aggatatcgc cgactactac tgccagcaga caacaactg gcccaccacc     360 ttcggcgctg gcaccaagct ggaactgaag cggaccgtgg ccgctccctc cgtgttcatc    420 cccacccctcc gacgagcagc tg                                            442

<210> SEQ ID NO 19
<211> LENGTH: 424
```

<212> TYPE: DNA
<213> ORGANISM: Artificial Sequence
<220> FEATURE:
<223> OTHER INFORMATION: Synthetic construct

<400> SEQUENCE: 19

| | |
|---|---|
| gcggccgcca tgaacttcgg cctgcggctg atcttcctgg tgctgaccct gaagggcgtg | 60 |
| cagtgccagg tgcagctggt ggaatccggc ggaggcgtgg tgcagcctgg cagatccctg | 120 |
| agactgtcct gcgccgcctc cggcttcacc ttctccagct acaccatgca ctgggtccga | 180 |
| caggcccctg gcaagggcct ggaatgggtc accttcatca gctacgacgg caacaacaag | 240 |
| tactacgccg actccgtgaa gggccggttc accatctccc gggacaactc caagaacacc | 300 |
| ctgtacctgc agatgaactc cctgcgggcc gaggacaccg ccatctacta ctgcgcccgg | 360 |
| accggctggc tgggcccttt tgattactgg ggccagggca ccctggtcac cgtgtcctcc | 420 |
| tagc | 424 |

<210> SEQ ID NO 20
<211> LENGTH: 445
<212> TYPE: DNA
<213> ORGANISM: Artificial Sequence
<220> FEATURE:
<223> OTHER INFORMATION: Synthetic construct

<400> SEQUENCE: 20

| | |
|---|---|
| gcggccgcca tggaatccca gacccaggtg ctgatctccc tgctgttctg ggtgtccggc | 60 |
| acctgtggcg agatcgtgct gacccagtcc cccggcaccc tgtctctgag ccctggcgag | 120 |
| agagccaccc tgtcctgcag agcctcccag tccgtgggct cctcctacct ggcttggtat | 180 |
| cagcagaagc ccggccaggc ccctcggctg ctgatctacg cgctttctc tcgggccacc | 240 |
| ggcatccctg accggttctc tggctccggc tccggcaccg acttcaccct gaccatctcc | 300 |
| cggctggaac ccgaggactt cgccgtgtac tactgccagc agtacggctc ctccccctgg | 360 |
| acctttggcc agggcaccaa ggtggaaatc aagcggaccg tggccgctcc ctccgtgttc | 420 |
| cttcccaccc tccgacgagc agctg | 445 |

<210> SEQ ID NO 21
<211> LENGTH: 1035
<212> TYPE: DNA
<213> ORGANISM: Artificial Sequence
<220> FEATURE:
<223> OTHER INFORMATION: Synthetic construct

<400> SEQUENCE: 21

| | |
|---|---|
| gctagcacaa agggccctag tgtgtttcct ctggctccct cttccaaatc cacttctggt | 60 |
| ggcactgctg ctctgggatg cctggtgaag gattactttc ctgaacctgt gactgtctca | 120 |
| tggaactctg gtgctctgac ttctggtgtc cacactttcc ctgctgtgct gcagtctagt | 180 |
| ggactgtact ctctgtcatc tgtggtcact gtgccctctt catctctggg aacccagacc | 240 |
| tacatttgta atgtgaacca caaccatccc aacactaaag tggacaaaaa agccgaaccc | 300 |
| aaatcctgtg acaaaaccca cacctgccca ccttgtcctg ccctgaact gctgggagga | 360 |
| ccttctgtgt ttctgttccc accaaaacca aaagatacct gatgatctc tagaacccct | 420 |
| gaggtgacat gtgtggtggt ggatgtgtct catgaggacc ctgaggtcaa atttaattgg | 480 |
| tacgtcgatg gagtggaagt ccacaatgcc aaaaccaagc ctagagagga acagtacaat | 540 |
| tcaacctaca gagtcgtcag tgtgctgact gtgctgcatc aggattggct gaatggcaag | 600 |

```
gaatacaagt gtaaagtctc aaacaaggcc ctgcctgctc caattgagaa aacaatctca        660
aaggccaagg gacagcctag ggaaccccag gtctacaccc tgccaccttc acgcgacgaa        720
ctgaccaaaa accaggtgtc cctgacatgc ctggtcaaag gcttctaccc ttctgacatt        780
gctgtggagt gggagtcaaa tggacagcct gagaacaact acaaaacaac cccccctgtg        840
ctggattctg atggctcttt ctttctgtac tccaaactga ctgtggacaa gtctagatgg        900
cagcagggga atgtcttttc ttgctctgtc atgcatgagg ctctgcataa ccactacact        960
cagaaatccc tgtctctgtc tcccgggaaa ggcggcggag gatctggcgg aggcggttct       1020
ggtggtggcg gatcc                                                        1035
```

<210> SEQ ID NO 22
<211> LENGTH: 435
<212> TYPE: DNA
<213> ORGANISM: Artificial Sequence
<220> FEATURE:
<223> OTHER INFORMATION: Synthetic construct

<400> SEQUENCE: 22

```
gcggccgcca tgaattttgg actgaggctg attttcctgg tgctgaccct gaaaggcgtc         60
cagtgtcagg tgcagctgca gcagcctggt gccgagctcg tgaaacctgg cgcctccgtg        120
aagatgtcct gcaaggcctc cggctacacc ttcaccagct acaacatgca ctgggtcaag        180
cagacccccg gcagaggcct ggaatggatc ggcgctatct accccggcaa cggcgacacc        240
tcctacaacc agaagttcaa gggcaaggcc accctgaccg ccgacaagtc ctcttccacc        300
gcctacatgc agctgtcctc cctgacctcc gaggactccg ccgtgtacta ctgcgcccgg        360
tctacctact acggcggcga ctggtacttc aacgtgtggg gcgctggcac caccgtgacc        420
gtgtctgctg ctagc                                                        435
```

<210> SEQ ID NO 23
<211> LENGTH: 405
<212> TYPE: DNA
<213> ORGANISM: Artificial Sequence
<220> FEATURE:
<223> OTHER INFORMATION: Synthetic construct

<400> SEQUENCE: 23

```
gcggccgcca tgaattttgg actgaggctg attttcctgg tgctgaccct gaaaggcgtc         60
cagtgtcaga tcgtgctgtc ccagtcccct gccatcctgt ctgctagccc tggcgagaaa        120
gtgacaatga cctgccgggc ctcctcctcc gtgtcctaca tccactggtt ccagcagaag        180
cccggctcca gccccaagcc ttggatctac gccacctcca acctggcctc tggcgtgcca        240
gtgcggtttt ccggctctgg ctctggcacc tcctactccc tgaccatctc tcgggtggaa        300
gccgaggatg ccgccaccta ctactgccag cagtggacca gcaaccccccc cacatttggc       360 ggaggcacca agctggaaat caagcggacc gtggcggcgc cctct                       405
```

<210> SEQ ID NO 24
<211> LENGTH: 631
<212> TYPE: DNA
<213> ORGANISM: Artificial Sequence
<220> FEATURE:
<223> OTHER INFORMATION: Synthetic construct

<400> SEQUENCE: 24

```
ggatccgcct gtccttgggc cgtgtccggc gctagagcct ctcctggctc tgccgcctcc         60
cccagactga gagagggccc tgagctgtcc cctgacgatc ctgccggcct gctggacctg        120
```

```
agacagggca tgtttgccca gctggtggcc cagaacgtgc tgctgatcga cggcccctg    180 tcctggtact ctgatcctgg cctggccggc gtgtccctga ccggcggact gtcctacaaa    240
gaggacacca agaactggt ggtggccaag gctggcgtgt actacgtgtt ctttcagctg    300
gaactgcggc gggtggtggc cggcgagggc tctggatctg tgtccctggc cctgcatctg    360
cagcccctga gatctgccgc tggcgccgct gctctggccc tgacagtgga tctgcctcct    420
gcctcctccg aggcccggaa ctccgcattc gggtttcagg gccggctgct gcacctgtct    480
gctggccaga gactgggagt gcatctgcac accgaggcca gagccagaca cgcctggcag    540
ctgacccagg gcgctaccgt gctgggcctg ttcagagtga ccccgagat cccagccggc    600 ctgcccagcc ctagatccga gtgataagct t                                    631
```

<210> SEQ ID NO 25
<211> LENGTH: 1458
<212> TYPE: DNA
<213> ORGANISM: Artificial Sequence
<220> FEATURE:
<223> OTHER INFORMATION: Synthetic construct

<400> SEQUENCE: 25

```
gcggccgcca tgaattttgg actgaggctg attttcctgg tgctgaccct gaaaggcgtc      60
cagtgtcagg tgcagctgca ggaatctggc cctggactcg tgcggccttc ccaaaccctg     120
tctctgacct gtaccgtgtc cggctactcc atcacctccg accacgcctg gtcttgggtg     180
cgacagcctc ctggcagagg cctggaatgg atcggctaca tctcctactc cggcatcacc     240
acctacaacc ccagcctgaa gtccagagtg accatgctgc gggacacctc caagaaccag     300
ttctccctgc ggctgtcctc cgtgaccgct gctgataccg ccgtgtacta ctgcgccaga     360
tctctggcca ggaccaccgc catggattac tggggccagg gctccctcgt gaccgtgtcc     420
tctgctagca ccaagggccc ctccgtgttc cctctggccc cttcctctaa atctacctct     480
ggcggcaccg ccgctctggg ctgcctcgtg aaggactact ccccgagcc cgtgacagtg     540 tcttggaact ctggcgccct gacctccggc gtgcacacct tccagctgt gctgcagtcc     600 tccggcctgt actccctgtc cagcgtcgtg actgtgcccc ctcatctct gggcacccag     660 acctacatct gcaacgtgaa ccacaagccc tccaacacca aggtggacaa gaaggtggaa     720
cccaagtcct gcgacaagac ccacacctgt cccccttgtc ctgcccctga actgctgggc     780
ggaccctctg tgttcctgtt cccaccaaaa ccgaaagaca ccctgatgat ctcccggacc     840
cccgaagtga cctgcgtggt ggtggatgtg tcccacgagg accctgaagt gaagttcaat     900
tggtacgtgg acggcgtgga agtgcacaac gccaagacca gcctagaga ggaacagtac     960 aactccacct accgggtggt gtccgtgctg accgtgctgc accaggattg gctgaacggc    1020
aaagagtaca agtgcaaggt gtccaacaag gccctgcctg cccccatcga aaagaccatc    1080
tccaaggcca agggccagcc acgggaaccc caggtgtaca cactgccccc tagccgcgac    1140
gagctgacca agaatcaggt gtccctgaca tgcctcgtga aaggcttcta cccctccgat    1200
atcgccgtgg aatgggagtc caacggccag cctgagaaca actacaagac cacccccct    1260 gtgctggact ccgacggctc attcttcctg tactcaaagc tgacagtgga caagtcccgg    1320
tggcagcagg gcaacgtgtt ctcctgctcc gtgatgcacg aggccctgca caaccactac    1380
acccagaagt ccctgtccct gagccccggg aaaggcggcg aggatctgg cggaggcggt    1440 tctggtggtg gcggatcc                                                  1458
```

```
<210> SEQ ID NO 26
<211> LENGTH: 405
<212> TYPE: DNA
<213> ORGANISM: Artificial Sequence
<220> FEATURE:
<223> OTHER INFORMATION: Synthetic construct

<400> SEQUENCE: 26
gcggccgcca tgaattttgg actgaggctg attttcctgg tgctgaccct gaaaggcgtc      60
cagtgtgaca tccagatgac ccagtccccc tccagcctgt ctgcctctgt gggcgacaga     120
gtgaccatca cctgtcgggc ctcccaggac atctcctcct acctgaactg gtatcagcag     180
aagcccggca aggcccccaa gctgctgatc tactacacct cccggctgca ctccggcgtg     240
ccctctagat tttccggctc tggctccggc accgacttta ccttcaccat cagctccctg     300
cagcccgagg atatcgccac ctactactgc cagcaaggca cacccctgcc ctacaccttt     360
ggccagggca ccaaggtgga aatcaagcgg accgtggcgg cgccc                     405

<210> SEQ ID NO 27
<211> LENGTH: 1455
<212> TYPE: DNA
<213> ORGANISM: Artificial Sequence
<220> FEATURE:
<223> OTHER INFORMATION: Synthetic construct

<400> SEQUENCE: 27
gcggccgcca tgaattttgg actgaggctg attttcctgg tgctgaccct gaaaggcgtc      60
cagtgtcagg tgcagctgca gcagtgggga gctggactgc tgaagccctc cgagacactg     120
tctctgacct gcgctgtgta cggcggctcc ttctccggct actactggtc ctggattcgg     180
cagtcccctg agaagggcct ggaatggatc ggcgagatca ccacggcgg ctacgtgacc     240 tacaacccca gcctggaatc cagagtgacc atctccgtgg acacctccaa gaaccagttc     300
tccctgaagc tgtcctccgt gaccgccgct gataccgccg tgtactactg cgccagagac     360
tacggccctg caactacga ctggtacttc gacctgtggg gcagaggcac cctcgtgacc      420
gtgtcctctg ctagcaccaa gggcccctcc gtgtttcctc tggccccttg ctcacgctcc     480
acctccgaat ctaccgccgc tctgggctgc ctcgtgaagg actacttccc cgagcccgtg     540
actgtgtctt ggaactctgg cgccctgacc tccggcgtgc acacctttcc agctgtgctg     600
cagtcctccg gcctgtactc cctgtccagc gtcgtgacag tgccctccag ctctctgggc     660
accaagacct acacctgtaa cgtggaccac aagccctcca acaccaaggt ggacaagcgg     720
gtggaatcta aatacggccc tccctgccct ccttgcccag ccctgaatt tctgggcgga     780 ccttccgtgt tcctgttccc cccaaaaccc aaggacaccc tgatgatctc ccggaccccc     840
gaagtgacct gcgtggtggt ggatgtgtcc caggaagatc ccgaggtgca gttcaattgg     900
tacgtggacg gcgtggaagt gcacaacgcc aagaccaagc ctagagagga acagttcaac     960
tccacctacc gggtggtgtc cgtgctgacc gtgctgcacc aggattggct gaacggcaaa    1020
gagtacaagt gcaaggtgtc caacaagggc ctgcccagct ccatcgaaaa gaccatcagc    1080
aaggccaagg gccagccccg ggaaccccag gtgtacacac tgcctccaag ccaggaagag    1140
atgaccaaga atcaggtgtc cctgacctgt ctcgtgaaag gcttctaccc ctccgatatc    1200
gccgtggaat gggagtccaa cggccagcct gagaacaact acaagaccac ccccctgtg    1260 ctggactccg acggcagctt cttcctgtac tctcgcctga ccgtggacaa gtcccggtgg    1320
caggaaggca acgtgttctc ctgctccgtg atgcacgagg ccctgcacaa ccactacacc    1380
```

```
cagaagtccc tgtccctgtc tctggggaaa ggcggcggag gatctggcgg aggcggttct      1440
ggtggtggcg gatcc                                                       1455

<210> SEQ ID NO 28
<211> LENGTH: 411
<212> TYPE: DNA
<213> ORGANISM: Artificial Sequence
<220> FEATURE:
<223> OTHER INFORMATION: Synthetic construct

<400> SEQUENCE: 28
gcggccgcca tgaattttgg actgaggctg attttcctgg tgctgaccct gaaaggcgtc        60
cagtgtgaga tcgtgctgac ccagtctcct gccaccctgt ctctgagccc tggcgagaga       120
gctaccctgt cctgccgtgc ctcccaatcc gtgtcctctt acctggcctg gtatcagcaa       180
aagcccggcc aggctccccg gctgctgatc tacgatgcct ccaatagagc caccggcatc       240
cctgccagat ctccggctc tggctctggc accgactttta ccctgaccat ctcctctctg       300
gaacccgagg acttcgccgt gtactactgc cagcagcggt ccaactggcc tcccgccctg       360
acatttggcg gaggcaccaa ggtggaaatc aagcggaccg tggcggcgcc c               411

<210> SEQ ID NO 29
<211> LENGTH: 449
<212> TYPE: PRT
<213> ORGANISM: Artificial Sequence
<220> FEATURE:
<223> OTHER INFORMATION: Synthetic construct

<400> SEQUENCE: 29

Gln Val Gln Leu Val Gln Ser Gly Ala Glu Val Lys Lys Pro Gly Glu
1               5                   10                  15

Thr Val Lys Ile Ser Cys Lys Ala Ser Asp Tyr Thr Phe Thr Tyr Tyr
            20                  25                  30

Gly Met Asn Trp Val Lys Gln Ala Pro Gly Gln Gly Leu Lys Trp Met
        35                  40                  45

Gly Trp Ile Asp Thr Thr Thr Gly Glu Pro Thr Tyr Ala Gln Lys Phe
    50                  55                  60

Gln Gly Arg Ile Ala Phe Ser Leu Glu Thr Ser Ala Ser Thr Ala Tyr
65                  70                  75                  80

Leu Gln Ile Lys Ser Leu Lys Ser Glu Asp Thr Ala Thr Tyr Phe Cys
                85                  90                  95

Ala Arg Arg Gly Pro Tyr Asn Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
```

```
            210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 30
<211> LENGTH: 219
<212> TYPE: PRT
<213> ORGANISM: Artificial Sequence
<220> FEATURE:
<223> OTHER INFORMATION: Synthetic construct

<400> SEQUENCE: 30

Asp Ile Val Met Thr Gln Ser Pro Leu Ser Val Pro Val Thr Pro Gly
1               5                   10                  15

Glu Pro Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Val Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Leu Gln His
                85                  90                  95

Leu Glu Tyr Pro Phe Thr Phe Gly Pro Gly Thr Lys Leu Glu Leu Lys
            100                 105                 110

Arg Thr Val Ala Ala Pro Ser Val Phe Ile Phe Pro Pro Ser Asp Glu
        115                 120                 125
```

-continued

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 460
<212> TYPE: PRT
<213> ORGANISM: Artificial Sequence
<220> FEATURE:
<223> OTHER INFORMATION: Synthetic construct

<400> SEQUENCE: 31

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

```
Thr Cys Val Val Asp Val Ser His Glu Asp Pro Glu Val Lys Phe
            275                 280                 285

Asn Trp Tyr Val Asp Gly Val Glu Val His Asn Ala Lys Thr Lys Pro
290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
            370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
            450                 455                 460

<210> SEQ ID NO 32
<211> LENGTH: 213
<212> TYPE: PRT
<213> ORGANISM: Artificial Sequence
<220> FEATURE:
<223> OTHER INFORMATION: Synthetic construct

<400> SEQUENCE: 32

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Thr Trp Tyr Gln Gln Lys Pro Gly Gln Ala Pro Ile Leu Val Ile Tyr
            35                  40                  45

Gly Glu Asn Lys Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175
```

```
Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Ala Glu Cys
    210

<210> SEQ ID NO 33
<211> LENGTH: 449
<212> TYPE: PRT
<213> ORGANISM: Artificial Sequence
<220> FEATURE:
<223> OTHER INFORMATION: Synthetic construct

<400> SEQUENCE: 33

Gln Val Gln Leu Gln Gln Ser Gly Ala Glu Val Lys Lys Phe Gly Ala
1               5                   10                  15

Ser Val Lys Val Ser Cys Glu Ala Ser Gly Tyr Thr Phe Pro Ser Tyr
            20                  25                  30

Val Leu His Trp Val Lys Gln Ala Pro Gly Gln Gly Leu Glu Trp Ile
        35                  40                  45

Gly Tyr Ile Asn Pro Tyr Asn Asp Gly Thr Gln Thr Asn Lys Lys Phe
    50                  55                  60

Lys Gly Lys Ala Thr Leu Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Phe Gly Gly Ser Tyr Gly Phe Ala Tyr Asn Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Asn Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Asn Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Asn His Glu
                420                 425                 430

Ala Leu His Asn His Tyr Thr Gln Lys Ser Leu Ser Leu Ser Pro Gly
            435                 440                 445

Lys

<210> SEQ ID NO 34
<211> LENGTH: 215
<212> TYPE: PRT
<213> ORGANISM: Artificial Sequence
<220> FEATURE:
<223> OTHER INFORMATION: Synthetic construct

<400> SEQUENCE: 34

Asp Ile Gln Leu Thr Gln Ser Pro Ser Ser Leu Ser Ala Ser Val Gly
1               5                   10                  15

Asp Arg Val Thr Met Thr Cys Ser Ala Ser Ser Ser Val Ser Ser Ser
            20                  25                  30

Tyr Leu Tyr Trp Tyr Gln Gln Lys Pro Gly Lys Ala Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Ser Ala Ser Tyr Phe Cys His Gln Trp Asn Arg Tyr Pro
                85                  90                  95

Tyr Thr Phe Gly Gly Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Pro Arg Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 35
<211> LENGTH: 450
<212> TYPE: PRT
<213> ORGANISM: Artificial Sequence
<220> FEATURE:
<223> OTHER INFORMATION: Synthetic construct

<400> SEQUENCE: 35

```
Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Thr Pro Ser Gly Ser Thr Asn Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Val Glu Asp Thr Ala Val Tyr Ile Cys
                85                  90                  95

Gly Arg Val Pro Tyr Arg Ser Thr Trp Tyr Pro Leu Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 36
<211> LENGTH: 214
<212> TYPE: PRT
<213> ORGANISM: Artificial Sequence
<220> FEATURE:
<223> OTHER INFORMATION: Synthetic construct

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu His Ser Lys Val Pro Thr Gln Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ser Thr Tyr Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 450
<212> TYPE: PRT
<213> ORGANISM: Homo sapiens

<400> SEQUENCE: 37

Glu Val Gln Leu Val Glu Ser Gly Gly Gly Leu Val Gln Pro Gly Gly
```

-continued

```
1               5                   10                  15
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
            435                 440                 445
Gly Lys
    450

<210> SEQ ID NO 38
<211> LENGTH: 449
<212> TYPE: PRT
<213> ORGANISM: Homo sapiens

<400> SEQUENCE: 38

Gln Val Gln Leu Lys Gln Ser Gly Pro Gly Leu Val Gln Pro Ser Gln
1               5                  10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

```
              340                 345                 350
Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
            435                 440                 445

Lys

<210> SEQ ID NO 39
<211> LENGTH: 448
<212> TYPE: PRT
<213> ORGANISM: Homo sapiens

<400> SEQUENCE: 39

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
```

-continued

```
                260                 265                 270
Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445
```

METHOD OF TREATING CANCER WITH AN EGFR TARGETED IMMUNOMODULATORY FUSION PROTEIN

CROSS REFERENCE TO RELATED APPLICATIONS

The application is a continuation application of and claims priority to copending U.S. patent application Ser. No. 14/458,674 filed on Aug. 13, 2014 which in turn claims priority to U.S. patent application Ser. No. 13/799,409 filed on Mar. 13, 2013, now U.S. Pat. No. 8,815,247, which in turn claims priority to Indian Patent Application No. 1689/CHE/2012 filed on Apr. 30, 2012 and Indian Patent Application No. 1690/CHE/2012 filed on Apr. 30, 2012, the contents of all are hereby incorporated by reference herein for all purposes.

BACKGROUND OF THE INVENTION

Technical Field

The present invention relates generally to the field of generating fusion proteins to be used in cancer therapy, and more specifically, to nucleotide sequences encoding the fusion proteins, wherein the fusion or chimeric polypeptides comprises at least one targeting moiety and at least one immunomodulatory moiety that counteracts the immune tolerance of cancer cells.

Related Art

The immune system provides the human body with a means to recognize and defend itself against microorganisms and substances recognized as foreign or potentially harmful. While passive immunotherapy of cancer with monoclonal antibodies and passive transfer of T cells to attack tumor cells have demonstrated clinical efficacy, the goal of active therapeutic vaccination to induce these immune effectors and establish immunological memory against tumor cells has remained challenging. Several tumor-specific and tumor-associated antigens have been identified, yet these antigens are generally weakly immunogenic and tumors employ diverse mechanisms to create a tolerogenic environment that allows them to evade immunologic attack. Strategies to overcome such immune tolerance and activating robust levels of antibody and/or T cell responses hold the key to effective cancer immunotherapy. More important, the individual proteins and how to create an active chimeric polypeptide with an active tertiary structure needs to be explored.

SUMMARY OF THE INVENTION

The present invention provides polynucleotides, as well as polypeptides encoded thereby, that are expressed in cancer cells. These polynucleotides and expressed polypeptides are useful in a variety of therapeutic methods for the treatment of cancer. The present invention further provides methods of reducing growth of cancer cells by counteracting immune tolerance of cancer cells, wherein T cell remain active and inhibit the recruitment of T-regulatory that are known to suppress the immune system's response to the tumor. Thus the chimeric polypeptides generated by the polynucleotides sequences of the present invention are useful for treating cancer because of the expressed fusion or chimeric polypeptides.

In one aspect, the present invention provides for chimeric polypeptides containing at least one targeting moiety to target a cancer cell and at least one immunomodulating moiety that counteracts immune tolerance of cancer cell, wherein the targeting moiety and the immunomodulating moiety are linked by a amino acid spacer of sufficient length of amino acid residues so that both moieties can successfully bond to their individual target. In the alternative, the targeting moiety and the immunomodulating moiety that counteract immune tolerance of cancer cell may be bound directly to each other. The chimeric/fusion polypeptides of the invention are useful for binding to a cancer cell receptor and reducing the ability of cancer cells to avoid an immune response.

The present invention is based on preparing chimeric/fusion proteins by expression of polynucleotides encoding the fusion proteins that counteract or reverse immune tolerance of cancer cells. Cancer cells are able to escape elimination by chemotherapeutic agents or tumor-targeted antibodies via specific immunosuppressive mechanisms in the tumor microenvironment and such ability of cancer cells is recognized as immune tolerance. Such immunosuppressive mechanisms include immunosuppressive cytokines (for example, Transforming growth factor beta (TGF-β)) and regulatory T cells and/or immunosuppressive myeloid dendritic cells (DCs). By counteracting tumor-induced immune tolerance, the present invention provides effective compositions and methods for cancer treatment, optional in combination with another existing cancer treatment. The present invention provides strategies to counteract tumor-induced immune tolerance and enhance the antitumor efficacy of chemotherapy by activating and leveraging T cell-mediated adaptive antitumor against resistant or disseminated cancer cells.

In another aspect, the present invention provides a molecule including at least one targeting moiety fused with at least one immunomodulatory moiety. The targeting moiety specifically binds a target molecule, and the immunomodulatory moiety specifically binds one of the following molecules: (i) Transforming growth factor-beta (TGF-β): (ii) Programmed death-1 ligand 1 (PD-L1) or Programmed death-1 ligand 2 (PD-L2); (iii) Receptor activator of nuclear factor-КB (RANK) ligand (RANKL); (iv) Transforming growth factor-beta receptor (TGF-pR); (v) Programmed death-1 (PD-1); (vi) 4-1BB receptor or (vii) Receptor activator of nuclear factor-κB (RANK).

In a further aspect, the targeting moiety includes an antibody, antibody fragment including the light or heavy chains of the antibody, scFv, or Fc-containing polypeptide that specifically binds a component of a tumor cell, tumor antigen, tumor vasculature, tumor microenvironment, or tumor-infiltrating immune cell. Preferably, the targeting moiety is an antibody or a fragment thereof having binding affinity for a component on a tumor cell. Notably each of the heavy chain and light chain may individually be linked to a separate and distinct immunomodulatory moiety. Further, a heavy or light chain of an antibody targeting moiety may be linked to an immunomodulatory moiety which in turn can be further linked to a second immunomodulatory moiety wherein there is a linker between the two immunomodulatory moieties.

In a still further aspect, there is provided a chimeric polypeptide that comprised a tumor targeting moiety and an immunomodulatory moiety comprising a molecule that binds transforming growth factor beta (TGF-β), wherein the tumor targeting moiety is an antibody that binds to EGFR1, where in the antibody can be the full antibody, heavy chain or light chain. The tumor targeting moiety may include monoclonal antibodies that target a cancer cell, including but not limited to cetuximab, trastuzumab, ritubximab, ipilimumab, tremelimumab, muromonab-CD3, abciximab, dacli-zumab, basiliximab, palivizumab, infliximab. gemtuzumab ozogamicin, alemtuzumab, ibritumomab tiuxetan, adalim-umab, omalizumab, tositumomab, I-131 tositumomab, efali-zumab, bevacizumab, panitumumab, pertuzumab, natali-zumab, etanercept, IGN101 (Aphton), voloximab (Biogen Idec and PDL BioPharm), Anti-CD80 mAb (Biogen Idec), Anti-CD23 mAb (Biogen Idel), CAT-3888 (Cambridge Antibody Technology), CDP-791 (Imclone), eraptuzumab (Immunomedics), MDX-010 (Medarex and BMS), MDX-060 (Medarex), MDX-070 (Medarex), matuzumab (Merck), CP-675,206 (Pfizer), CAL (Roche), SGN-30 (Seattle Genet-ics), zanolimumab (Serono and Genmab), adecatumumab (Sereno), oregovomab (United Therapeutics), nimotuzumab (YM Bioscience), ABT-874 (Abbott Laboratories), deno-sumab (Amgen), AM 108 (Amgen), AMG 714 (Amgen), fontolizumab (Biogen Idec and PDL BioPharm), dacli-zumab (Biogent Idec and PDL BioPharm), golimumab (Centocor and Schering-Plough), CNTO 1275 (Centocor), ocrelizumab (Genetech and Roche), HuMax-CD20 (Gen-mab), belimumab (HGS and GSK), epratuzumab (Immuno-medics), MLN1202 (Millennium Pharmaceuticals), visili-zumab (PDL BioPharm), tocilizumab (Roche), ocrerlizumab (Roche), certolizumab pegol (UCB, formerly Celltech), ecu-lizumab (Alexion Pharmaceuticals), pexelizumab (Alexion Pharmaceuticals and Procter & Gamble), abciximab (Cen-tocor), ranibizimumab (Genetech), mepolizumab (GSK), TNX-355 (Tanox), or MYO-029 (Wyeth).

In an another aspect, the tumor targeting moiety is a monoclonal antibody that binds to HER2/Neu, CD20, CTLA4, EGFR1 and wherein the antibody can be the full antibody, heavy chain or light chain.

In yet another aspect, the targeting moiety is a molecule that specifically binds epidermal growth factor receptor (EGFR1, Erb-B 1), HER2/neu (Erb-B2), CD20, cytotoxic T-lymphocyte antigen-4 (CTLA-4) which is essential for Treg function (CD 152); H-1 and Interleukin-6 (IL-6).

In a still further aspect, the targeting moiety specifically binds a component of a regulatory T cell (treg), myeloid suppressor cell, or dendritic cell. In another aspect, the targeting moiety specifically binds one of the following molecules: (i) CD4; (ii) CD25 (IL-2ct receptor; IL-2aR); (iii) Transforming growth factor-beta receptor (TGF-pR); (vi) Transforming growth factor-beta (TGF-β): (vii) Pro-grammed Death-1 (PD-1); (viii) Programmed death-1 ligand (PD-LI or PD-L2.

In another aspect, the immunomodulatory moiety specifi-cally binds one of the following molecules: (i) Transforming growth factor-beta (TGF-β): (ii) Programmed death-1 ligand (PD-L1 or PD-L2); or 4-1BB receptor.

In yet another aspect, the immunomodulatory moiety includes a molecule that binds TGF-β and inhibits the function thereof. Specifically the immunomodulatory moi-ety includes an extracellular ligand-binding domain of Transforming growth factor-beta receptor TGF-βRII, TGF-βRIIb, or TGF-βRIII In another aspect the immunomodu-latory moiety includes an extracellular ligand-binding domain (ECD) of TGF-βRII. Still further the immunomodu-latory moiety may include H-4-1BB ligand which binds to the 4-1BB receptor to stimulate T-cells to help eradiate tumor.

In a still further aspect, the targeting moiety includes an antibody, antibody fragment, or polypeptide that specifically binds to HER2/neu, EGFR1, CD20, or cytotoxic T-lympho-cyte antigen-4 (CTLA-4) and wherein the immunomodula-tory moiety includes an extracellular ligand-binding domain of TGF-βRII.

In yet another aspect, the immunomodulatory moiety includes a molecule that specifically binds to and inhibit the activity of Programmed death-1 ligand 1 (PD-L 1) or Pro-grammed death-1 ligand 2 (PD-L2). In another aspect, the immunomodulatory moiety includes an extracellular ligand-binding domain or ectodomain of Programmed Death-1 (PD-1).

In a further aspect, the targeting moiety includes an antibody, antibody fragment, or polypeptide that specifically binds to HER2/neu, EGFR1, CD20, cytotoxic T-lymphocyte antigen-4 (CTLA-4), CD25 (1L-2a receptor; IL-2aR), or CD4 and wherein, the immunomodulatory moiety includes an extracellular ligand-binding domain or ectodomain of Programmed Death-1 (PD-1).

In a still further aspect, the targeting moiety includes an antibody or antibody fragment that specifically binds to CD20, and the immunomodulatory moiety includes a sequence from transforming growth factor-0 (TGF-β).

In one aspect, the present invention provides for opti-mized genes encoding for a fusion polypeptide comprising at least one targeting moiety and at least one immunomodu-latory moiety for treating cancer in a human subject wherein the optimized genes have been modified to increase expres-sion in a human subject. preferably the optimized genes comprise sequences for encoding a targeting moiety or an immunomodulatory moiety selected from SEQ ID NOs: 12 to 28.

In another aspect, the present invention provides for a vector comprising optimized genes for treating cancer in a human subject wherein the optimized genes have been modified to increase CG sequences. Preferably, the vector includes sequences for encoding at least one targeting moi-ety and at least one immunomodulatory moiety selected from SEQ ID NOs: 12 to 28.

In yet another aspect, the present invention provides for a method of treating cancer in a subject, the method compris-ing:
 a. providing at least one recombinant vector comprising nucleotide sequences that encode at least one targeting moiety and at least one immunomodulatory moiety selected from SEQ ID NOs: 12 to 28; and
 b. administering the recombinant vector to the subject under conditions such that said nucleotide sequences are expressed at a level which produces a therapeuti-cally effective amount of the encoded fusion proteins in the subject.

In an alternative aspect, the present invention provides an expression vector comprising polynucleotides of optimized genes that encode at least one targeting moiety and at least one immunomodulatory moiety selected from SEQ ID NOs: 12 to 28.

In yet another aspect, the present invention provides a recombinant host cell transfected with a polynucleotide that encodes a fusion protein peptide of the present invention.

In a still further aspect, the present invention contem-plates a process of preparing a fusion protein of the present invention comprising:
 a. transfecting a host cell with polynucleotide sequences that encode chimeric fusion proteins to produce a transformed host cell, wherein the polynucleotide sequences encode at least one targeting moiety and at least one immunomodulatory moiety selected from SEQ ID NOs: 12 to 28; and
 b. maintaining the transformed host cell under biological conditions sufficient for expression of the peptide.

In another aspect, the present invention relates to the use of a chimeric fusion protein, as shown in FIGS. 1 to 15, in the use of a medicament for the treatment of cancer. Preferably, the fusion protein is expressed in a host cell and such expressed proteins are administered in a therapeutic amount to reduce the effects of cancer in a subject in need thereof.

In a still further aspect, the present invention provides a method of preventing or treating a neoplastic disease. The method includes administration to a subject in need thereof one or more fusion proteins of the invention, in various aspects, the subject is administered one or more molecule of the invention in combination with another anticancer therapy, in one aspect, the anticancer therapy includes a chemotherapeutic molecule, antibody, small molecule kinase inhibitor, hormonal agent or cytotoxic agent. The anticancer therapy may also include ionizing radiation, ultraviolet radiation, cryoablation, thermal ablation, or radiofrequency ablation.

In yet another aspect, the present invention provides for a method of preparing therapeutically active antibody-peptide fusion proteins, the method comprising;
a. preparing a codon optimized sequence of the said fusion protein;
b. cloning the optimized sequence of said fusion protein in a host cell capable of transient or continued expression;
c. growing the host cell in a media under suitable conditions for growing and allowing the host cell to express the cloned protein; and
d. subjecting the expressed protein to purification and optionally checking the bi-specific binding capabilities of the protein to its targets.

In a preferred embodiment the therapeutically active antibody-peptide fusion proteins is a targeting antibody fused to one or more immunomodulating moiety that counteracts immune tolerance of a cancer cell. In one aspect, the immunomodulating moiety may be linked by an amino acid spacer of sufficient length to allow bi-specific binding of the molecule. The immunomodulating moiety may be bound to either the C-terminus of the heavy or light chain of the antibody In a preferred method as described above, the immunomodulating moiety is (i) Transforming growth factor-beta (TGF-β), (ii) Programmed death-1 (PD-1), (iii) CTLA-4 or (iv) 4-1BB or parts thereof and the targeting antibody binds epidermal growth factor receptor (EGFR1, Erb-B 1), HER2/neu (Erb-B2), CD20, CD6, CTLA-4, Mucin 1(MUC-1), Interleukin-2 (IL-2) or Interleukin-6 (IL-6).

The method of the present invention provides nucleotide sequences that encode the therapeutically active antibody-peptide fusion proteins and such expression may be conducted in a transient cell line or a stable cell line. The transient expression is accomplished by transfecting or transforming the host with vectors carrying the fusion proteins into mammalian host cells Once the fusion peptides are expressed, they are preferably subjected to purification and in-vitro tests to check its bi-specificity, that being, having the ability to bind to both the target moiety and immunomodulating moiety. Such tests may include in-vitro test such as ELISA or NK/T-cell binding assays to validate bi-functional target binding or immune cell stimulation.

Notably once the specific fusion peptides demonstrate the desired bi-specificity, such fusion peptides are selected for sub-cloning into a stable cell line for larger scale expression and purification. Such stable cell lines are previously disclosed, such as a mammalian cell line, including but not limited to HEK293, CHO or NSO.

In a further aspect, the culture medium can be improved by additions to such medium. For example, the culture medium may include a divalent transitional metallic salt which is added to the cell culture either initially or in fed-batch mode to reduce accumulation of lactate during culturing and/or reduce heterogeneity of the fusion proteins. A desirable transitional metallic salt includes a zinc ion and the addition of the metal ion may be carried out during different phases of the production.

Other features and advantages of the invention will be apparent from the following detailed description, drawings and claims.

BRIEF DESCRIPTION OF THE DRAWINGS

FIG. 1 shows the amino acid sequences of with the amino acid sequence of Anti-HER2/neu-TGFβRII fusion protein at LC constant region with the amino acid sequence of anti-HER2/neu heavy chain (SEQ ID NO: 1) and anti-HER2/neu light chain (SEQ ID NO: 2) attached to amino residues for TGF-βRII (immunomodulatory moiety) (SEQ ID NO: 4) identified in bold letters and wherein a linker (SEQ ID NO: 3) is positioned between the anti-HER2/neu light chain and TGF-βRII and shown in italics.

FIG. 2 shows the amino acid sequences of Anti-EGFR1-TGFβRII fusion protein at LC constant region with amino acid sequence of Anti-EGFR1 heavy chain (SEQ ID NO: 5) and the amino acid sequence of Anti-EGFR1 light chain (SEQ ID NO: 6) attached to amino acid residues for TGF-βRII (immunomodulatory moiety) (SEQ ID NO: 4) identified in bold letters and wherein a linker (SEQ ID NO: 3) is positioned between the Anti-EGFR1 light chain and TGF-βRII and shown in italics.

FIG. 3 shows the amino acid sequences of Anti-CTLA4-TGFβRII fusion protein at LC constant region with amino acid sequence of anti-CTLA4 heavy chain (SEQ ID NO: 7) and amino acid sequence of anti-CTLA4 light chain (SEQ ID NO: 8) attached to amino acid residues for TGF-βRII (immunomodulatory moiety) (SEQ ID NO: 4) identified in bold letters and wherein a linker (SEQ ID NO: 3) is positioned between the anti-CTLA4 light chain and TGF-βRII and shown in italics.

FIG. 4 shows the amino acid sequences of Anti-HER2/neu HC-4-1BB and LC-TGFβRII fusion protein with amino acid sequence of Anti-HER2/neu/HC-4-1BB fusion protein wherein the amino acid sequence for Anti-HER2/neu heavy chain (SEQ ID NO: 1) is attached to a linker (SEQ ID NO: 3) shown in italics and the sequence for 4-1BB (immunomodulatory moiety) (SEQ ID NO: 9) is in written text font and amino acid sequence of anti-HER2/neu light chain (SEQ ID NO: 2) attached to amino residues for TGF-βRII (immunomodulatory moiety) (SEQ ID NO: 4) identified in bold letters and wherein a linker (SEQ ID NO: 3) is positioned between the anti-HER2/neu light chain and TGF-βRII and shown in italics.

FIG. 5 shows the amino acid sequence of Anti-EGFR1 HC-4-1BB and LC-TGFβRII fusion protein with amino acid sequence of Anti-EGFR1 heavy chain-4-1BB fusion protein wherein the amino acid sequence for Anti-EGFR1 heavy chain (SEQ ID NO: 5) is attached to a linker (SEQ ID NO: 3) is shown in italics and the sequence for 4-1BB (immunomodulatory moiety) (SEQ ID NO: 9) is in written text font and amino acid sequence of light chain Anti-EGFR1 (SEQ ID NO: 6) attached to amino residues for TGF-βRII (immunomodulatory moiety) (SEQ ID NO: 4) identified in bold letters with a linker (SEQ ID NO: 3) therebetween.

FIG. 6 shows the amino acid sequence of Anti-CTLA4 HC-4-1BB and LC-TGFβRII fusion protein with amino acid sequence of Anti-CTLA4 heavy chain-4-1BB fusion protein wherein the amino acid sequence for Anti-CTLA4 heavy chain (SEQ ID NO: 7) is attached to a linker (SEQ ID NO: 3) is shown in italics and the sequence for 4-1BB (immunomodulatory moiety) (SEQ ID NO: 9) is in written text font and amino acid sequence of Anti-CTLA4 light chain (SEQ ID NO: 8) is attached to amino residues for TGF-βRII (immunomodulatory moiety) (SEQ ID NO: 4) identified in bold letters with a linker (SEQ ID NO: 3) therebetween.

FIG. 7 shows the amino acid sequence of Anti-HER2/neu HC-PD1 and LC-TGFβRII fusion protein with amino acid sequence of Anti-HER2/neu heavy chain-PD1 fusion protein wherein the amino acid sequence for the Anti-HER2/neu heavy chain (SEQ ID NO: 1) is attached to a linker (SEQ ID NO: 3) is shown in italics and the sequence for PD1 (immunomodulatory moiety) (SEQ ID NO: 10) is in written text font and amino acid sequence of Anti-HER2/neu light chain (SEQ ID NO: 2) is attached to amino residues for TGF-βRII (immunomodulatory moiety) (SEQ ID NO: 4) identified in bold letters with a linker (SEQ ID NO: 3) therebetween.

FIG. 8 shows the amino acid sequence of Anti-EGFR1 HC-PD1 and LC-TGFβRII fusion protein with amino acid sequence of Anti-EGFR1 heavy chain-PD1 fusion protein wherein the amino acid sequence Anti-EGFR1 heavy chain (SEQ ID NO: 5) is attached to a linker (SEQ ID NO: 3) shown in italics and the sequence for PD1 (immunomodulatory moiety) (SEQ ID NO: 10) is in written text font and amino acid sequence of Anti-EGFR1 light chain (SEQ ID NO: 6) attached to amino residues for TGF-βRII (immunomodulatory moiety) (SEQ ID NO: 4) identified in bold letters with a linker (SEQ ID NO: 3) therebetween.

FIG. 9 shows the amino acid sequence of Anti-CTLA4 HC-PD1 and LC-TGFβRII fusion protein with amino acid sequence of Anti-CTLA4 heavy chain-PD1 fusion protein wherein the amino acid sequence Anti-CTLA4 heavy chain (SEQ ID NO: 7) is attached to a linker (SEQ ID NO: 3) shown in italics and the sequence for PD1 (immunomodulatory moiety) (SEQ ID NO: 10) is in written text font and amino acid sequence of Anti-CTLA4 light chain (SEQ ID NO: 8) attached to amino residues for TGF-βRII (immunomodulatory moiety) (SEQ ID NO: 4) identified in bold letters with a linker (SEQ ID NO: 3) therebetween.

FIG. 10 shows the amino acid sequence of Anti-HER2/neu HC-TGFβRII-4-1BB fusion protein with amino acid sequence of Anti-HER2/neu heavy chain-TGFβRII-4-1BB fusion protein wherein the amino acid sequence for Anti-HER2/neu heavy chain (SEQ ID NO: 37) is attached to a linker (SEQ ID NO: 3) shown in italics and the sequence for TGFβRII (immunomodulatory moiety) (SEQ ID NO: 4) is identified in bold letters and the amino acid sequence for 4-1BB (immunomodulatory moiety) (SEQ ID NO: 9) is in written text font with linker between (SEQ ID No: 11) and including the amino acid sequence of Anti-HER2/neu light chain (SEQ ID NO: 2).

FIG. 11 shows the amino acid sequence of Anti-EGFR1 HC-TGFβRII-4-1BB fusion protein with amino acid sequence of Anti-EGFR1 heavy chain-TGFβRII-4-1BB fusion protein wherein the amino acid sequence for Anti-EGFR1 heavy chain (SEQ ID NO: 38) sequence is attached to a linker (SEQ ID NO: 3) shown in italics and the sequence for TGFβRII (immunomodulatory moiety) (SEQ ID NO: 4) is identified in bold letters and the amino acid sequence for 4-1BB (immunomodulatory moiety) (SEQ ID NO: 9) is in written text font with linker between (SEQ ID NO: 11) and including the amino acid sequence of Anti-EGFR1 light chain (SEQ ID NO: 6).

FIG. 12 shows the amino acid sequence of Anti-CTLA4 HC-TGFβRII-4-1BB fusion protein with amino acid sequence of Anti-CTLA4 heavy chain-TGFβRII-4-1BB fusion protein wherein the amino acid sequence Anti-CTLA4 heavy chain (SEQ ID NO: 39) is attached to a linker (SEQ ID NO: 3) shown in italics and the sequence for TGFβRII (immunomodulatory moiety) (SEQ ID NO: 4) is identified in bold letters and the amino acid sequence for 4-1BB (immunomodulatory moiety) (SEQ ID NO: 9) is in written text font with linker between (SEQ ID NO: 11) and including the amino acid sequence of Anti-CTLA4 light chain (SEQ ID NO: 8).

FIG. 13 shows the amino acid sequence of Anti-HER2/neu HC-TGFβRII-PD1 fusion protein with amino acid sequence of Anti-HER2/neu heavy chain-TGFβRII-PD1 fusion protein wherein the amino acid sequence Anti-HER2/neu heavy chain (SEQ ID NO: 37) is attached to a linker (SEQ ID NO: 3) shown in italics and the sequence for TGFβRII (immunomodulatory moiety) (SEQ ID NO: 4) is identified in bold letters and the amino acid sequence for PD-1 (immunomodulatory moiety) (SEQ ID NO: 10) is in written text font with linker between (SEQ ID No: 11) and including the amino acid sequence of Anti-HER2/neu light chain (SEQ ID NO: 2).

FIG. 14 shows the amino acid sequence of Anti-EGFR1 HC-TGFβRII-PD1 fusion protein with amino acid sequence of Anti-EGFR1 heavy chain-TGFβRII-PD1 fusion protein wherein the amino acid sequence Anti-EGFR1 heavy chain (SEQ ID NO: 38) is attached to a linker (SEQ ID NO: 3) shown in italics and the sequence for TGFβRII (immunomodulatory moiety) (SEQ ID NO: 4) is identified in bold letters and the amino acid sequence for PD-1 (immunomodulatory moiety) (SEQ ID NO: 10) is in written text font with linker between (SEQ ID No: 11) and including the amino acid sequence of Anti-EGFR1 light chain (SEQ ID NO: 6).

FIG. 15 shows the of Anti-CTLA4 HC-TGFβRII-PD1 fusion protein with amino acid sequence of Anti-CTLA4 heavy chain-TGFβRII-PD1 fusion protein wherein the amino acid sequence Anti-CTLA4 heavy chain (SEQ ID NO: 39) is attached to a linker (SEQ ID NO: 3) shown in italics and the sequence for TGFβRII (immunomodulatory moiety) (SEQ ID NO: 4) is identified in bold letters and the amino acid sequence for PD-1 (immunomodulatory moiety) (SEQ ID NO: 10) is in written text font with linker between (SEQ ID NO: 11) and including the amino acid sequence of Anti-CTLA4 light chain (SEQ ID NO: 8).

FIG. 16 shows the nucleotide sequence of Anti-HER2/neu heavy chain constant region with linker (SEQ ID NO: 12) and TGFβRII ECD (SEQ ID NO: 13) that have been codon optimized for expression in CHO cell.

FIG. 17 shows the nucleotide sequence of Anti-HER2/neu heavy chain variable region (SEQ ID NO: 14), Anti-HER2/neu light chain variable region (SEQ ID NO: 15) and Anti-EGFR1 heavy chain constant region with linker (SEQ ID NO: 16) that have been codon optimized for expression in CHO cell.

FIG. 18 shows the nucleotide sequence of Anti-EGFR1 heavy chain variable region (SEQ ID NO: 17), Anti-EGFR1 light chain variable region (SEQ ID NO: 18), Anti-CTLA4 heavy chain variable region (SEQ ID NO: 19) and Anti-CTLA4 light chain variable region (SEQ ID NO: 20) that have been codon optimized for expression in CHO cell.

FIG. 19 shows the nucleotide sequence of Anti CD20 IgG1 molecule (SEQ ID NO: 21), Anti-CD20 heavy chain variable region (SEQ ID NO: 22) and Anti-CD20 light chain variable region (SEQ ID NO: 23) that have been codon optimized for expression in CHO cell.

FIG. 20 shows the nucleotide sequence of 4-1BB (SEQ ID NO: 24) and Anti-IL6R heavy chain (SEQ ID NO: 25) that have been codon optimized for expression in CHO cell.

FIG. 21 shows the nucleotide sequence of Anti-IL6R light chain variable region (SEQ ID NO: 26), Anti-4-1BB heavy chain (SEQ ID NO: 27) and Anti-4-1BB light chain variable region (SEQ ID NO: 28) that have been codon optimized for expression in CHO cell.

FIG. 24 A shows that Anti-HER2/neu-TGFβRII and Anti-EGFR1-TGFβRII molecules bind to the TGFβ indicating that the fusion protein is functional and B shows that Anti-HER2-TGFβRII inhibits the proliferation of BT474 cell line similar to the Bmab200 (Herceptin).

FIG. 26 shows the ADCC activity of Anti-HER2-TGFβRII on BT474 cells is similar to that of Bmab200 (Herceptin).

FIG. 30 A shows the binding activity of Anti-CTLA4-TGFβRII to determine the level of PD1-Fc binding and B shows the binding activity of Anti-EGRF1-4-1BB to determine the binding of 4-1BBL.

FIG. 31 A shows the binding activity of Anti-EGFR1-4-1BB to EGFR and B shows the binding activity of PD1-Fc-4-1BB to find out PDL1-Fc.

FIG. 33 shows photographs of expressed proteins and reduction alkylation thereof.

FIG. 34 A shows the mass spectrum Mass Spectrum of light chain (LC) (Reduced) of Anti-HER2/neu-TGFβRII ECD fusion and B shows Deconvoluted Mass Spectrum of LC (Reduced) of Anti-HER2/neu-TGFβRII ECD fusion.

FIGS. 39, 40 and 41 provide lists of expected/observed tryptic peptide of the light chain, heavy chain and linked motif of the Anti-HER2/neu-TGFβRII ECD fusion protein, respectively.

FIG. 43 provides a list of expected/observed tryptic peptide of the light chain of the Anti-EGFR1-TGFβRII ECD fusion protein.

FIG. 44 shows the list of expected/observed tryptic peptide of the heavy chain of the Anti-EGFR1-TGFβRII ECD fusion protein.

FIG. 45 shows the list of expected/observed tryptic peptide of the heavy chain of the Anti-EGFR1-TGFβRII ECD fusion protein.

FIG. 46 shows the amino acid sequences of Cantuzumab-TGFβRII fusion protein at LC constant region with amino acid sequence of Cantuzumab heavy chain (SEQ ID NO: 29) and amino acid sequence of Cantuzumab light chain (SEQ ID NO: 30) attached to amino acid residues for TGF-βRII (immunomodulatory moiety) (SEQ ID NO: 4) identified in bold letters and wherein a linker (SEQ ID NO: 3) is positioned between the Cantuzumab light chain and TGF-βRII and shown in italics.

FIG. 47 shows the amino acid sequences of Cixutumumab-TGFβRII fusion protein at LC constant region with amino acid sequence of Cixutumumab heavy chain (SEQ ID NO: 31) and amino acid sequence of Cixutumumab light chain (SEQ ID NO: 32) attached to amino acid residues for TGF-βRII (immunomodulatory moiety) (SEQ ID NO: 4) identified in bold letters and wherein a linker (SEQ ID NO: 3) is positioned between the Cixutumumab light chain and TGF-βRII and shown in italics.

FIG. 48 shows the amino acid sequences of Clivatuzumab-TGFβRII fusion protein at LC constant region with amino acid sequence of Clivatuzumab heavy chain (SEQ ID NO: 33) and amino acid sequence of Clivatuzumab light chain (SEQ ID NO: 34) attached to amino acid residues for TGF-βRII (immunomodulatory moiety) (SEQ ID NO: 4) identified in bold letters and wherein a linker (SEQ ID NO: 3) is positioned between the Clivatuzumab light chain and TGF-βRII and shown in italics.

FIG. 49 shows the amino acid sequences of Pritumumab-TGFβRII fusion protein at LC constant region with amino acid sequence of Pritumumab heavy chain (SEQ ID NO: 35) and amino acid sequence of Pritumumab light chain (SEQ ID NO: 36) attached to amino acid residues for TGF-βRII (immunomodulatory moiety) (SEQ ID NO: 4) identified in bold letters and wherein a linker (SEQ ID NO: 3) is positioned between the Pritumumab light chain and TGF-βRII and shown in italics.

FIG. 50 shows the amino acid sequence of Cantuzumab HC-4-1BB and LC-TGFβRII fusion protein wherein the amino acid sequence for the Cantuzumab heavy chain (SEQ ID NO: 29) is attached to a linker (SEQ ID NO: 3) which is shown in italics and the sequence for 4-1BB (immunomodulatory moiety) (SEQ ID NO: 9) is in written text font and amino acid sequence of Cantuzumab light chain (SEQ ID NO: 30) is attached to amino residues for TGF-βRII (immunomodulatory moiety) (SEQ ID NO: 4) identified in bold letters with a linker (SEQ ID NO: 3) therebetween.

FIG. 51 shows the amino acid sequence of Cixutumumab HC-4-1BB and LC-TGFβRII fusion protein wherein the amino acid sequence for the Cixutumumab heavy chain (SEQ ID NO: 31) is attached to a linker (SEQ ID NO: 3)

Figure 22:
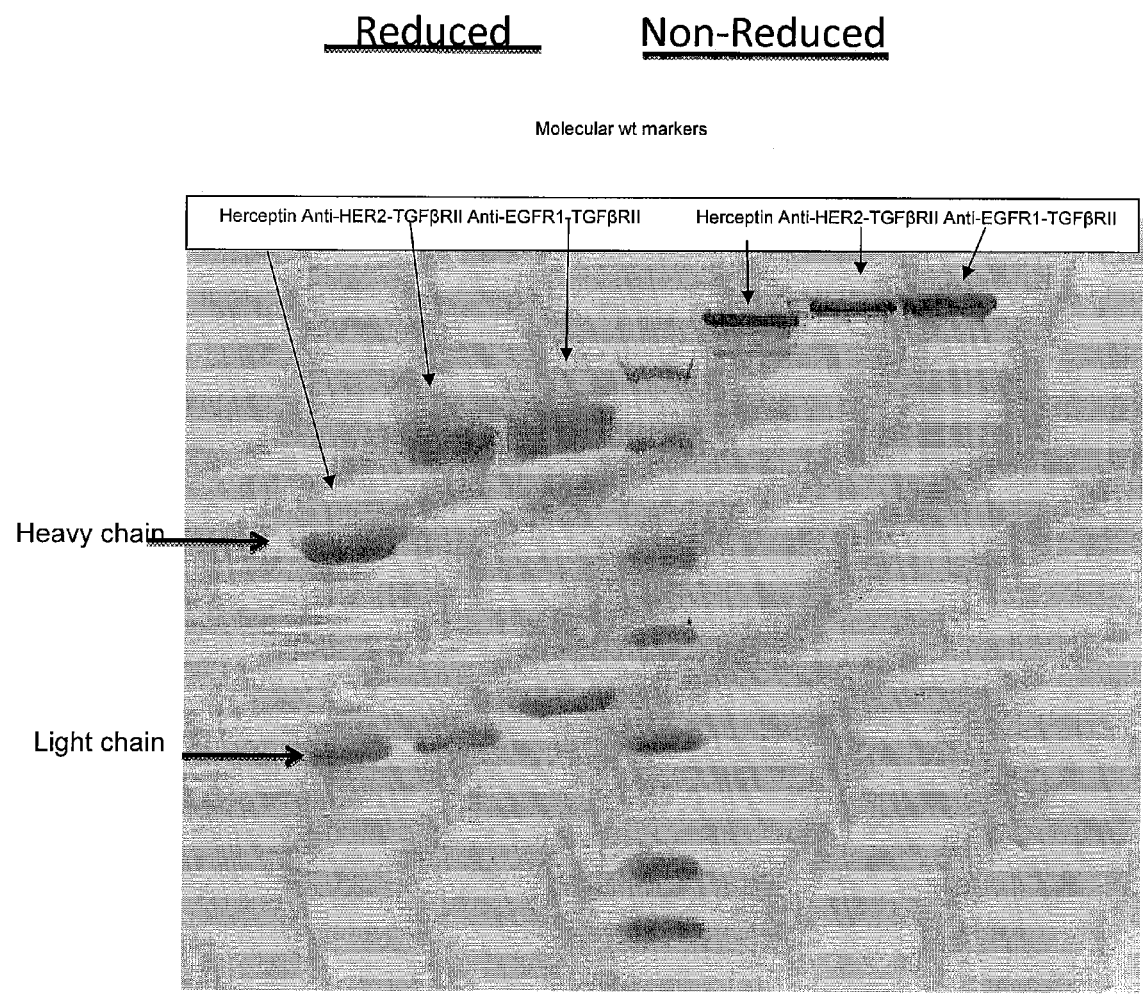
FIG. 22 shows the analysis of Protein A purified Anit-HER2/neu-TGFβRII and Anti-EGFR1-TGFβRII at 12% PAGE FIG. 23 A shows Anti-HER2/neu-TGFβRII samples analyzed by Protein A/SEC Chromtography and B Anti-EGFR1-TGFβRII samples analyzed by Protein A/SEC Chromtography.

shown in italics and the sequence for 4-1BB (immunomodulatory moiety) (SEQ ID NO: 9) is in written text font and amino acid sequence of Cixutumumab light chain (SEQ ID NO: 32) is attached to amino residues for TGF-βRII (immunomodulatory moiety) (SEQ ID NO: 4) identified in bold letters with a linker (SEQ ID NO: 3) therebetween.

FIG. 52 shows the amino acid sequence of Clivatuzumab HC-4-1BB and LC-TGFβRII fusion protein wherein the amino acid sequence for the Clivatuzumab heavy chain (SEQ ID NO: 33) is attached to a linker (SEQ ID NO: 3) shown in italics and the sequence for 4-1BB (immunomodulatory moiety) (SEQ ID NO: 9) is in written text font and amino acid sequence of Clivatuzumab light chain (SEQ ID NO: 34) is attached to amino residues for TGF-βRII (immunomodulatory moiety) (SEQ ID NO: 4) identified in bold letters with a linker (SEQ ID NO: 3) therebetween.

FIG. 53 shows the amino acid sequence of Pritumumab HC-4-1BB and LC-TGFβRII fusion protein wherein the amino acid sequence for the Pritumumab heavy chain (SEQ ID NO: 35) is attached to a linker (SEQ ID NO: 3) shown in italics and the sequence for 4-1BB (immunomodulatory moiety) (SEQ ID NO: 9) is in written text font and amino acid sequence of Pritumumab light chain (SEQ ID NO: 36) is attached to amino residues for TGF-βRII (immunomodulatory moiety) (SEQ ID NO: 4) identified in bold letters with a linker (SEQ ID NO: 3) therebetween.

FIG. 54 shows the amino acid sequence of Cantuzumab-HC-PD1 and LC-TGFβRII fusion protein wherein the amino acid sequence for the Cantuzumab heavy chain (SEQ ID NO: 29) is attached to a linker (SEQ ID NO: 3) shown in italics and the sequence for PD1 (immunomodulatory moiety) (SEQ ID NO: 10) is in written text font and amino acid sequence of Cantuzumab light chain (SEQ ID NO: 30) is attached to amino residues for TGF-βRII (immunomodulatory moiety) (SEQ ID NO: 4) identified in bold letters with a linker (SEQ ID NO: 3) therebetween.

FIG. 55 shows the amino acid sequence of Cixutumumab-HC-PD1 and LC-TGFβRII fusion protein wherein the amino acid sequence for the Cixutumumab heavy chain (SEQ ID NO: 31) is attached to a linker (SEQ ID NO: 3) shown in italics and the sequence for PD1 (immunomodulatory moiety) (SEQ ID NO: 10) is in written text font and amino acid sequence of Cixutumumab light chain (SEQ ID NO: 32) is attached to amino residues for TGF-βRII (immunomodulatory moiety) (SEQ ID NO: 4) identified in bold letters with a linker (SEQ ID NO: 3) therebetween.

FIG. 56 shows the amino acid sequence of Clivatuzumab-HC-PD1 and LC-TGFβRII fusion protein wherein the amino acid sequence for the Clivatuzumab heavy chain (SEQ ID NO: 33) is attached to a linker (SEQ ID NO: 3) shown in italics and the sequence for PD1 (immunomodulatory moiety) (SEQ ID NO: 10) is in written text font and amino acid sequence of Clivatuzumab light chain (SEQ ID NO: 34) is attached to amino residues for TGF-βRII (immunomodulatory moiety) (SEQ ID NO: 4) identified in bold letters with a linker (SEQ ID NO: 3) therebetween.

FIG. 57 shows the amino acid sequence of Pritumumab-HC-PD1 and LC-TGFβRII fusion protein wherein the amino acid sequence for the Pritumumab heavy chain (SEQ ID NO: 35) is attached to a linker (SEQ ID NO: 3) shown in italics and the sequence for PD1 (immunomodulatory moiety) (SEQ ID NO: 10) is in written text font and amino acid sequence of Pritumumab light chain (SEQ ID NO: 36) is attached to amino residues for TGF-βRII (immunomodulatory moiety) (SEQ ID NO: 4) identified in bold letters with a linker (SEQ ID NO: 3) therebetween.

FIG. 58 shows the amino acid sequence of Cantuzumab HC-TGFβRII-4-1BB fusion protein wherein the amino acid sequence for Cantuzumab heavy chain (SEQ ID NO: 29) is attached to a linker (SEQ ID NO: 3) shown in italics and the sequence for TGFβRII (immunomodulatory moiety) (SEQ ID NO: 4) is identified in bold letters and the amino acid sequence for 4-1BB (immunomodulatory moiety) (SEQ ID NO: 9) is in written text font with linker between (SEQ ID No: 11) and including the amino acid sequence of Cantuzumab light chain (SEQ ID NO: 30).

FIG. 59 shows the amino acid sequence of Cixutumumab HC-TGFβRII-4-1BB fusion protein wherein the amino acid sequence for Cixutumumab heavy chain (SEQ ID NO: 31) is attached to a linker (SEQ ID NO: 3) shown in italics and the sequence for TGFβRII (immunomodulatory moiety) (SEQ ID NO: 4) is identified in bold letters and the amino acid sequence for 4-1BB (immunomodulatory moiety) (SEQ ID NO: 9) is in written text font with linker between (SEQ ID No: 11) and including the amino acid sequence of Cixutumumab light chain (SEQ ID NO: 32).

FIG. 60 shows the amino acid sequence of Clivatuzumab HC-TGFβRII-4-1BB fusion protein wherein the amino acid sequence for Clivatuzumab heavy chain (SEQ ID NO: 33) is attached to a linker (SEQ ID NO: 3) shown in italics and the sequence for TGFβRII (immunomodulatory moiety) (SEQ ID NO: 4) is identified in bold letters and the amino acid sequence for 4-1BB (immunomodulatory moiety) (SEQ ID NO: 9) is in written text font with linker between (SEQ ID No: 11) and including the amino acid sequence of Clivatuzumab light chain (SEQ ID NO: 34).

FIG. 61 shows the amino acid sequence of Pritumumab HC-TGFβRII-4-1BB fusion protein wherein the amino acid sequence for Pritumumab heavy chain (SEQ ID NO: 35) is attached to a linker (SEQ ID NO: 3) shown in italics and the sequence for TGFβRII (immunomodulatory moiety) (SEQ ID NO: 4) is identified in bold letters and the amino acid sequence for 4-1BB (immunomodulatory moiety) (SEQ ID NO: 9) is in written text font with linker between (SEQ ID No: 11) and including the amino acid sequence of Pritumumab light chain (SEQ ID NO: 36).

FIG. 62 shows the amino acid sequence of Cantuzumab HC-TGFβRII-PD1 fusion protein wherein the amino acid sequence for Cantuzumab heavy chain (SEQ ID NO: 29) is attached to a linker (SEQ ID NO: 3) shown in italics and the sequence for TGFβRII (immunomodulatory moiety) (SEQ ID NO: 4) is identified in bold letters and the amino acid sequence for PD1 (immunomodulatory moiety) (SEQ ID NO: 10) is in written text font with linker between (SEQ ID No: 11) and including the amino acid sequence of Cantuzumab light chain (SEQ ID NO: 30).

FIG. 63 shows the amino acid sequence of Cixutumumab HC-TGFβRII-PD1 fusion protein wherein the amino acid sequence for Cixutumumab heavy chain (SEQ ID NO: 31) is attached to a linker (SEQ ID NO: 3) shown in italics and the sequence for TGFβRII (immunomodulatory moiety) (SEQ ID NO: 4) is identified in bold letters and the amino acid sequence for PD1 (immunomodulatory moiety) (SEQ ID NO: 10) is in written text font with linker between (SEQ ID No: 11) and including the amino acid sequence of Cixutumumab light chain (SEQ ID NO: 32).

FIG. 64 shows the amino acid sequence of Clivatuzumab HC-TGFβRII-PD1 fusion protein wherein the amino acid sequence for Clivatuzumab heavy chain (SEQ ID NO: 33) is attached to a linker (SEQ ID NO: 3) shown in italics and the sequence for TGFβRII (immunomodulatory moiety) (SEQ ID NO: 4) is identified in bold letters and the amino acid sequence for PD1 (immunomodulatory moiety) (SEQ ID NO: 10) is in written text font with linker between (SEQ ID No: 11) and including the amino acid sequence of Clivatuzumab light chain (SEQ ID NO: 34).

FIG. 65 shows the amino acid sequence of Pritumumab HC-TGFβRII-PD1 fusion protein wherein the amino acid sequence for Pritumumab heavy chain (SEQ ID NO: 35) is attached to a linker (SEQ ID NO: 3) shown in italics and the sequence for TGFβRII (immunomodulatory moiety) (SEQ ID NO: 4) is identified in bold letters and the amino acid sequence for PD1 (immunomodulatory moiety) (SEQ ID NO: 10) is in written text font with linker between (SEQ ID No: 11) and including the amino acid sequence of Pritumumab light chain (SEQ ID NO: 36).

DETAILED DESCRIPTION OF THE INVENTION

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

Unless otherwise defined, all technical and scientific terms used herein have the meaning commonly understood by one of ordinary skill in the art to which this invention belongs. The terminology used herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. The following terms have the meanings given:

The term "polynucleotide" as used herein means a sequence of nucleotides connected by phosphodiester linkages. Polynucleotides are presented herein in the direction from the 5' to the 3' direction. A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U). A polynucleotide of the present invention can be prepared using standard techniques well known to one of skill in the art.

The term, "optimized" as used herein means that a nucleotide sequence has been altered to encode an amino acid sequence using codons that are preferred in the production cell or organism, generally a eukaryotic cell, for example, a cell of *Pichia*, a cell of *Trichoderma*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in CHO mammalian cells; however optimized expression of these sequences in other eukaryotic cells is also envisioned herein. The amino acid sequences encoded by optimized nucleotide sequences are also referred to as optimized. The term "expression" as used herein is defined as the transcription and/or translation of a particular nucleotide sequence driven by its promoter.

The term "transfection" of a cell as used herein means that genetic material is introduced into a cell for the purpose of genetically modifying the cell. Transfection can be accomplished by a variety of means known in the art, such as transduction or electroporation.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, ocular cancer, pancreatic cancer, colorectal cancer, renal cancer, liver cancer, brain cancer, lymphoma, leukemia, lung cancer and the like.

The term "transgene" is used in a broad sense to mean any heterologous nucleotide sequence incorporated in a vector for expression in a target cell and associated expression control sequences, such as promoters. It is appreciated by those of skill in the art that expression control sequences will be selected based on ability to promote expression of the transgene in the target cell. An example of a transgene is a nucleic acid encoding a chimeric fusion protein of the present invention.

The term "expression vector" as used herein means a vector containing a nucleic acid sequence coding for at least part of a gene product capable of being transcribed. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well. The term also includes a recombinant plasmid or virus that comprises a polynucleotide to be delivered into a host cell, either in vitro or in vivo. Preferably the host cell is a transient cell line or a stable cell line and more preferably a mammalian host cell and selected from the group consisting of HEK293, CHO and NSO.

The term "subject," as used herein means a human or vertebrate animal including a dog, cat, horse, cow, pig, sheep, goat, chicken, monkey, rat, and mouse.

The term "therapeutically effective amount" as used herein means the amount of the subject compound that will elicit the biological or medical response of a tissue, system, animal or human that is being sought by the researcher, veterinarian, medical doctor or other clinician.

The term "pharmaceutically acceptable" as used herein means the carrier, diluent or excipient must be compatible with the other ingredients of the formulation and not deleterious to the recipient thereof.

The term "recombinant" as used herein means a genetic entity distinct from that generally found in nature. As applied to a polynucleotide or gene, this means that the polynucleotide is the product of various combinations of cloning, restriction and/or ligation steps, and other procedures that result in the production of a construct that is distinct from a polynucleotide found in nature.

The term "substantial identity" or "substantial similarity," as used herein when referring to a nucleic acid or fragment thereof, indicates that when optimally aligned with appropriate nucleotide insertions or deletions with another nucleic acid (or its complementary strand), there is nucleotide sequence identity in at least about 95 to 99% of the sequence.

The term "peptide," "polypeptide" and "protein" are used interchangeably to denote a sequence polymer of at least two amino acids covalently linked by an amide bond.

The term "homologous" as used herein and relating to peptides refers to amino acid sequence similarity between two peptides. When an amino acid position in both of the peptides is occupied by identical amino acids, they are homologous at that position. Thus by "substantially homologous" means an amino acid sequence that is largely, but not entirely, homologous, and which retains most or all of the activity as the sequence to which it is homologous. As used herein, "substantially homologous" as used herein means that a sequence is at least 50% identical, and preferably at least 75% and more preferably 95% homology to the reference peptide. Additional peptide sequence modification are included, such as minor variations, deletions, substitutions or derivitizations of the amino acid sequence of the sequences disclosed herein, so long as the peptide has substantially the same activity or function as the unmodified peptides. Notably, a modified peptide will retain activity or function associated with the unmodified peptide, the modified peptide will generally have an amino acid sequence "substantially homologous" with the amino acid sequence of the unmodified sequence.

The term "administering" as used herein is defined as the actual physical introduction of the composition into or onto (as appropriate) the host subject. Any and all methods of introducing the composition into the subject are contemplated according to the present invention; the method is not dependent on any particular means of introduction and is not to be so construed. Means of introduction are well-known to those skilled in the art, and preferably, the composition is administered subcutaneously or intratumorally. One skilled in the art will recognize that, although more than one route can be used for administration, a particular route can provide a more immediate and more effective reaction than another route. Local or systemic delivery can be accomplished by administration comprising application or instillation of the immunovaccines into body cavities, inhalation or insufflation of an aerosol, or by parenteral introduction, comprising intramuscular, intravenous, intraportal, intrahepatic, peritoneal, subcutaneous, or intradermal administration. In the event that the tumor is in the central nervous system, the composition must be administered intratumorally because there is no priming of the immune system in the central nervous system.

Although chemotherapeutic agents can induce "immunogenic" tumor cell death and facilitate cross-presentation of antigens by dendritic cells, tumors create a tolerogenic environment that allows them to suppress the activation of innate and adaptive immune responses and evade immunologic attack by immune effector cells. The present invention provides strategies to counteract tumor-induced immune tolerance in the tumor microenvironment and can enhance the antitumor efficacy of chemotherapy by activating and leveraging T cell-mediated adaptive antitumor immunity against disseminated cancer cells.

The present invention is based on the discovery that targeted immunomodulatory antibodies or fusion proteins of the present invention can counteract or reverse immune tolerance of cancer cells. Cancer cells are able to escape elimination by chemotherapeutic agents or tumor-targeted antibodies via specific immunosuppressive mechanisms in the tumor microenvironment and such ability of cancer cells is recognized as immune tolerance. By counteracting tumor-induced immune tolerance, the present invention provides effective compositions and methods for cancer treatment, optional in combination with another existing cancer treatment.

The present invention provides compositions and methods for producing fusion proteins that counteract immune tolerance in the tumor microenvironment and promote T cell-mediated adaptive antitumor immunity for maintenance of durable long-term protection against recurrent or disseminated cancers. These fusion proteins are designed to facilitate effective long term T cell-mediated immune responses against tumor cells by at least one of the following:

a. promoting death of tumor cells via enhancement of antibody-dependent cellular cytotoxicity (ADCC); and
b. increasing activation and proliferation of antitumor CD8+ T cells by negating immune suppression mediated by regulatory T cells and myeloid suppressor cells. These antitumor immune responses may be activated in tandem with the sensitization of tumor cells to immune effector-mediated cytotoxicity, thereby establishing a positive feedback loop that augments tumor cytoreduction and reinforces adaptive antitumor immunity.

In addition, the fusion proteins of the present invention are distinguished from and superior to existing therapeutic, molecules in at least one of the following aspects: (i) To counteract immune tolerance in the tumor microenvironment and promote T cell-mediated adaptive antitumor immunity for maintenance of long-term protection against recurrent or disseminated cancers (for prevention or treatment of diverse cancers); (ii) To produce immune cell compositions for adoptive cellular therapy of diverse cancers; and (iii) To serve as immune adjuvants or vaccines for prophylaxis of diverse cancers or infectious diseases.

The targeted immunostimulatory antibodies and/or fusion proteins of the invention provide the ability to disrupt immunosuppressive networks in the tumor microenvironment. Tumors employ a wide array of regulatory mechanisms to avoid or suppress the immune response. Cancer cells actively promote immune tolerance in the tumor microenvironment via the expression of cytokines and molecules that inhibit the differentiation and maturation of antigen-presenting dendritic cells (DC). The immunosuppressive cytokines and ligands produced by tumor cells include the following: (i) Transforming growth factor-beta (TGF-$\beta$); (ii) Programmed death-1 ligand 1 (PD-L1; B7-H1); (iii) Vascular endothelial growth factor (VEGF); and (iv) Interleukin-10 (1L-10).

In addition to blocking dendritic cell (DC) maturation, these molecules promote the development of specialized subsets of immunosuppressive CD4$^+$ T cells (regulatory T cells; Treg cells) and myeloid-derived suppressor cells (MDSC). Tregs are a minority sub-population of CD4$^+$ T cells that constitutively express CD25 [the interleukin-2 (IL-2) receptor cc-chain] and the forkhead box P3 (FOXP3) transcription factor. Tregs (CD4+CD25+FoxP3+cells) maintain immune tolerance by restraining the activation, proliferation, and effector functions of a wide range of immune cells, including CD4 and CDS T cells, natural killer (NK) and NKT cells, B cells and antigen presenting cells (APCs) in vitro and in vivo.

The accumulation of Treg cells in the tumor microenvironment reinforces tumor immune tolerance and facilitates tumor progression and metastases. The increased expression of immunosuppressive cytokines (TGF-$\beta$; PD-L1) and tumor-infiltrating Tregs is correlated with a reduction of survival of patients with diverse types of cancers. The fusion proteins of the present invention inhibit key immunosuppressive molecules expressed by the targeted tumor cell or tumor-infiltrating Treg cells and myeloid suppressor cells (DCs or MDSC). As such, they provide the targeted ability to inhibit the development or function of Tregs within the tumor microenvironment.

The present invention provides a method of preventing or treating a neoplastic disease. The method includes administration to a subject in need thereof one or more fusion proteins of the present invention in combination with another anticancer therapy, wherein the anticancer therapy is a chemotherapeutic molecule, antibody, small molecule kinase inhibitor, hormonal agent, cytotoxic agent, targeted therapeutic agent, anti-angiogenic agent, ionizing radiation, ultraviolet radiation, cryoablation, thermal ablation, or radiofrequency ablation.

As used herein, the term "antibody" includes natural or artificial mono- or polyvalent antibodies including, but not limited to, polyclonal, monoclonal, multispecific, human, humanized or chimeric antibodies, single chain antibodies, Fab fragments. F(ab') fragments, fragments produced by a Fab expression library, anti-idiotypic (anti-Id) antibodies (including, e.g., anti-Id antibodies to antibodies of the invention), and epitope-binding fragments of any of the above. The antibody may be from any animal origin including birds and mammals. In one aspect, the antibody is, or derived from, a human, murine (e.g., mouse and rat), donkey, sheep, rabbit, goat, guinea pig, camel, horse, or chicken. Further, such antibody may be a humanized version of an antibody. The antibody may be monospecific, bispecific, trispecific, or of greater multispecificity. The antibody herein specifically include a "chimeric" antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

Examples of antibodies which can be incorporated into compositions and methods disclosed herein include, but are not limited, to antibodies such as trastuzumab (anti-HER2/neu antibody); Pertuzumab (anti-HER2 mAb); cetuximab (chimeric monoclonal antibody to epidermal growth factor receptor EGFR): panitumumab (anti-EGFR antibody); nimotuzumab (anti-EGFR antibody); Zalutumumab (anti-EGFR mAb); Necitumumab (anti-EGFR mAb); MDX-210 (humanized anti-HER-2 bispecific antibody); MDX-210 (humanized anti-HER-2 bispecific antibody); MDX-447 (humanized anti-EGF receptor bispecific antibody); Rituximab (chimeric murine/human anti-CD20 mAb); Obinutuzumab (anti-CD20 mAb); Ofatumumab (anti-CD20 mAb); Tositumumab-1131 (anti-CD20 mAb); ibritumomab tiuxetan (anti-CD20 mAb); Bevacizumab (anti-VEGF mAb); Ramucirumab (anti-VEGFR2 mAb); Ranibizumab (anti-VEGF mAb); Aflibercept (extracellular domains of YEGFR1 and VEGFR2 fused to IgG1 Fc): AMG386 (angiopoietin-1 and -2 binding peptide fused to IgG1 Fc); Dalotuzumab (anti-1GF-1R mAb): Gemtuzumab ozogamicin (anti-CD33 mAb); Alemtuzumab (anti-Campath-1/CD52 mAb); Brentuximab vedotin (anti-CD30 mAb); Catumaxomab (bispecific mAb that targets epithelial cell adhesion molecule and CD3); Naptumomab (anti-5T4 mAb); Girentuximab (anti-Carbonic anhydrase ix): or Farletuzumab (anti-folate receptor). Other examples include antibodies such as Panorex™ (17-1 A) (murine monoclonal antibody); Panorex (@ (17-1 A) (chimeric murine monoclonal antibody); BEC2 (ami-idiotypic mAb, mimics the GD epitope) (with BCG): Oncolym (Lym-1 monoclonal antibody); SMART M 1 95 Ab, humanized 13' 1 LYM-1 (Oncolym), Ovarex (B43.13, anti-idiotypic mouse mAb); 3622W94 mAb that binds to EGP40 (17-1 A) pancarcinoma antigen on adenocarcinomas; Zenapax (SMART Anti-Tac (IL-2 receptor); SMART M1 95 Ab, humanized Ab, humanized); NovoMAb-G2 (pancarcinoma specific Ab): TNT (chimeric mAb to histone antigens); TNT (chimeric mAb to histone antigens); GJiomab-H (Monoclonals-Humanized Abs); GN1-250 Mab; EMD-72000 (chimeric-EGF antagonist); LymphoCide (humanized IL.L.2 antibody); and MDX-260 bispecific, targets GD-2, ANA Ab, SMART 1DiO Ab, SMART ABL 364 Ab or ImmuRAIT-CEA.

Various methods have been employed to produce antibodies. Hybridoma technology, which refers to a cloned cell line that produces a single type of antibody, uses the cells of various species, including mice (murine), hamsters, rats, and humans. Another method to prepare an antibody uses genetic engineering including recombinant DNA techniques. For example, antibodies made from these techniques include, among others, chimeric antibodies and humanized antibodies. A chimeric antibody combines DNA encoding regions from more than one type of species. For example, a chimeric antibody may derive the variable region from a mouse and the constant region from a human. A humanized antibody comes predominantly from a human, even though it contains nonhuman portions. Like a chimeric antibody, a humanized antibody may contain a completely human constant region. But unlike a chimeric antibody, the variable region may be partially derived from a human. The nonhuman, synthetic portions of a humanized antibody often come from CDRs in murine antibodies. In any event, these regions are crucial to allow the antibody to recognize and bind to a specific antigen.

In one embodiment, a hybridoma can produce a targeted fusion protein comprising a targeting moiety and an immunomodulatory moiety. In one embodiment, a targeting moiety comprising an antibody, antibody fragment, or polypeptide is linked or fused to an immunomodulatory moiety consisting of a polypeptide, with a linker or without a linker. The linker can be an amino acid linker. In one embodiment, a linker is (GGGGS)n wherein n is 1, 2, 3, 4, 5, 6, 7, or 8. For example, GGGGSGGGGSGGGGS (SEQ ID NO: 3). In another embodiment, a linker is EPKSCDK (SEQ ID NO: 11). In various aspects, the length of the linker may be modified to optimize binding of the target moiety or the function of the immunomodulatory moiety. In various aspects, the immunomodulatory moiety is a polypeptide that is fused to the C-terminus of the Fc region of the heavy chain of a targeting antibody or Fc-containing fusion protein. In another aspect, the immunomodulatory moiety is a polypeptide that is fused to the C-terminus of the light chain of a targeting antibody.

An antibody fragment can include a portion of an intact, antibody, e.g. including the antigen-binding or variable region thereof. Examples of antibody fragments include Fab, Fab', F(ab')2, and Fv fragments; Fc fragments or Fc-fusion products; diabodies; linear antibodies; single-chain antibody molecules; and multispecific antibodies formed from antibody fragment(s). An intact antibody is one which includes an antigen-binding variable region as well as a light chain constant domain (CL) and heavy chain constant domains, CHI, CH2 and CH3. The constant domains may be native sequence constant domains (e.g., human native sequence constant domains) or amino acid sequence variant thereof for any other modified Fc (e.g. glycosylation or other engineered Fc).

The fusion proteins of the present invention may be synthesized by conventional techniques known in the art, for example, by chemical synthesis such as solid phase peptide synthesis. Such methods are known to those skilled in the art. In general, these methods employ either solid or solution phase synthesis methods, well known in the art. Specifically, the methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups and any solid support are removed either sequentially or concurrently to afford the final polypeptide. By simple modification of this general procedure, it is possible to add more than one amino acid at a time to a growing chain, for example, by coupling (under condition that do not racemize chiral centers) a protected tripeptide with a properly protected dipeptide to form, after deprotection, a pentapeptide.

Typical protecting groups include t-butyloxycarbonyl (Boc), 9-fluorenylmethoxycarbonyl (Fmoc), benxyloxycarbonyl (Cbz), p-toluenesulfonyl (Tos); 2,4-dinitrophenyl, benzyl (Bzl), biphenylisopropyl oxy-carboxycarbonyl, cyclohexyl, isopropyl, acetyl, o-nitrophenylsulfonyl, and the like. Of these, Boc and Fmoc are preferred.

Typical solid supports are generally cross-linked polymeric materials. These include divinylbenzene cross-linked styrene-based polymers, for example, divinylbenzene-hydroxymethyl styrene copolymers, divinylbenzene-chloromethyl styrene copolymers, and divinylbenzene-benzhydrylaminopolystyrene copolymers. The divinylbenzene-benzhydrylaminopolystyrene copolymers, as illustrated herein using p-methyl-benzhydrylamine resin, offers the advantage of directly introducing a terminal amide functional group into the peptide chain, which function is retained by the chain when the chain is cleaved from the support.

In one method, the polypeptides are prepared by conventional solid phase chemical synthesis on, for example, an Applied Biosystems, Inc. (ABI) 430A peptide synthesizer using a resin that permits the synthesis of the amide peptide form and using t-Boc amino acid derivatives (Peninsula Laboratories, Inc.) with standard solvents and reagents. Polypeptides containing either L- or D-amino acids may be synthesized in this manner. Polypeptide composition is confirmed by quantitative amino acid analysis and the specific sequence of each peptide may be determined by sequence analysis.

Preferably, the polypeptides can be produced by recombinant DNA techniques by synthesizing DNA encoding the desired polypeptide. Once coding sequences for the desired polypeptides have been synthesized or isolated, they can be cloned into any suitable vector for expression. Numerous cloning vectors are known to those of skill in the art, and the selection of an appropriate cloning vector is a matter of choice. The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. Heterologous leader sequences can be added to the coding sequence that causes the secretion of the expressed polypeptide from the host organism. Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

The expression vector may then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, HEK293, baby hamster kidney (BHK) cells, monkey kidney cells (COS), human hepatocellular carcinoma cells (e.g., Hep G2), Madin-Darby bovine kidney ("MDBK") cells, NOS cells derived from carcinoma cells, such as sarcoma, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda,* and *Trichoplusia ni*. The proteins may also be expressed in Trypanosomes.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art. Once purified, the amino acid sequences of the proteins can be determined, i.e., by repetitive cycles of Edman degradation, followed by amino acid analysis by HPLC. Other methods of amino acid sequencing are also known in the art.

Once synthesized or otherwise produced, the inhibitory activity of a candidate polypeptide can be tested by assessing the ability of the candidate to inhibit the lipopolysaccharide-induced nuclear translocation of NF-.kappa.B by, for example, using murine endothelial cells.

The fusion proteins of the present invention can be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular cancer type targeted. The compositions also preferably include pharmaceutically acceptable vehicles, carriers or adjuvants, well known in the art, such as human serum albumin, ion exchangers, alumina, lecithin, buffer substances such as phosphates, glycine, sorbic acid, potassium sorbate, and salts or electrolytes such as protamine sulfate. Suitable vehicles are, for example, water, saline, dextrose, glycerol, ethanol, or the like, and combinations thereof. Actual methods of preparing such compositions are known, or will be apparent, to those skilled in the art. See, e.g., Remington's Pharmaceutical Sciences, Mack Publishing Company, Easton, Pa., 18th edition, 1990.

The above compositions can be administered using conventional modes of delivery including, but not limited to, intravenous, intraperitoneal, oral, intralymphatic, or subcutaneous administration. Local administration to a tumor in question, or to a site of inflammation, e.g., direct injection into an arthritic joint, will also find use with the present invention.

Therapeutically effective doses will be easily determined by one of skill in the art and will depend on the severity and course of the disease, the patient's health and response to treatment, and the judgment of the treating physician.

EXPERIMENTAL

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

The Fusion proteins comprising of IgG heavy chain linked to immunomodulator (either suppressor or activator) ligands were expressed by codon optimized genes for the expression of CHO cells. The codon optimized nucleotide sequences defined by SEQ ID NOs: 12 to 28 were expressed in (CHO) cells and the expressed chimeric/fusion proteins are shown in Table 1

| Fusion protein Details |
|---|
| Anti-HER2/neu heavy chain + TGFβ-RII ECD and Anti-HER2/neu light chain |
| Anti-EGFR1 heavy chain + TGFβ-RII ECD and Anti-EGFR1 light chain |
| Anti-CTLA4 heavy chain + TGFβ-RII ECD and Anti-CTLA4 light chain |
| Anti-CTLA4 heavy chain + PD1 ectodomain and Anti-CTLA4 light chain |
| Anti-HER2/neu heavy chain + 4-1BBL and Anti-HER2/neu light chain |
| Anti-EGFR1 heavy chain + 4-1BBL and Anti-EGFR1 light chain |
| Anti-CTLA4 heavy chain + 4-1BBL and Anti-CTLA4 light chain |
| PD1 ectodomain-Fc-4-1BBL |
| TGFβRII ECD-Fc-4-1BBL |

| Fusion protein Details |
|---|
| Anti-EGFR1 heavy chain + PD1 ectodomain and Anti-EGFR1 light chain |
| Anti-CD20 heavy chain + 4-1BBL and Anti-CD20 light chain |
| Anti-HER2/neu heavy chain + PD1 ectodomain and Anti-HER2/neu light chain |
| Anti-IL6Rheavy chain + PD1 ectodomain and Anti-IL6R light chain |
| Anti-IL6Rheavy chain + TGFβ-RII ECD and Anti-IL6R light chain |
| Anti-4-1BB heavy chain + PD1 ectodomain and Anti-4-1BB light chain |

The expressed protein were characterized by using SDS PAGE and the expressed fusion proteins Anit-HER2/neu-TGFβRII and Anti-EGFR1-TGFβRII were purified from culture supernatants using ProteinA column and the results are shown in FIG. 22. Notably, Anti-EGFR1-TGFβRII light chain mass is higher and it may be because of the presence of two glycosylation sites on the variable regions light and heavy chain. Both the Anti-HER2/neu-TGFβRII & Anti-EGFR1-TGFβRII heavy chains mass are higher because of the TGFβRII. Also Anti-HER2/neu-TGFβRII heavy chain has four N-glycosylation sites while Anti-EGFR1-TGFβRII has five N-glycosylation sites.

Example 2

Figure 23:
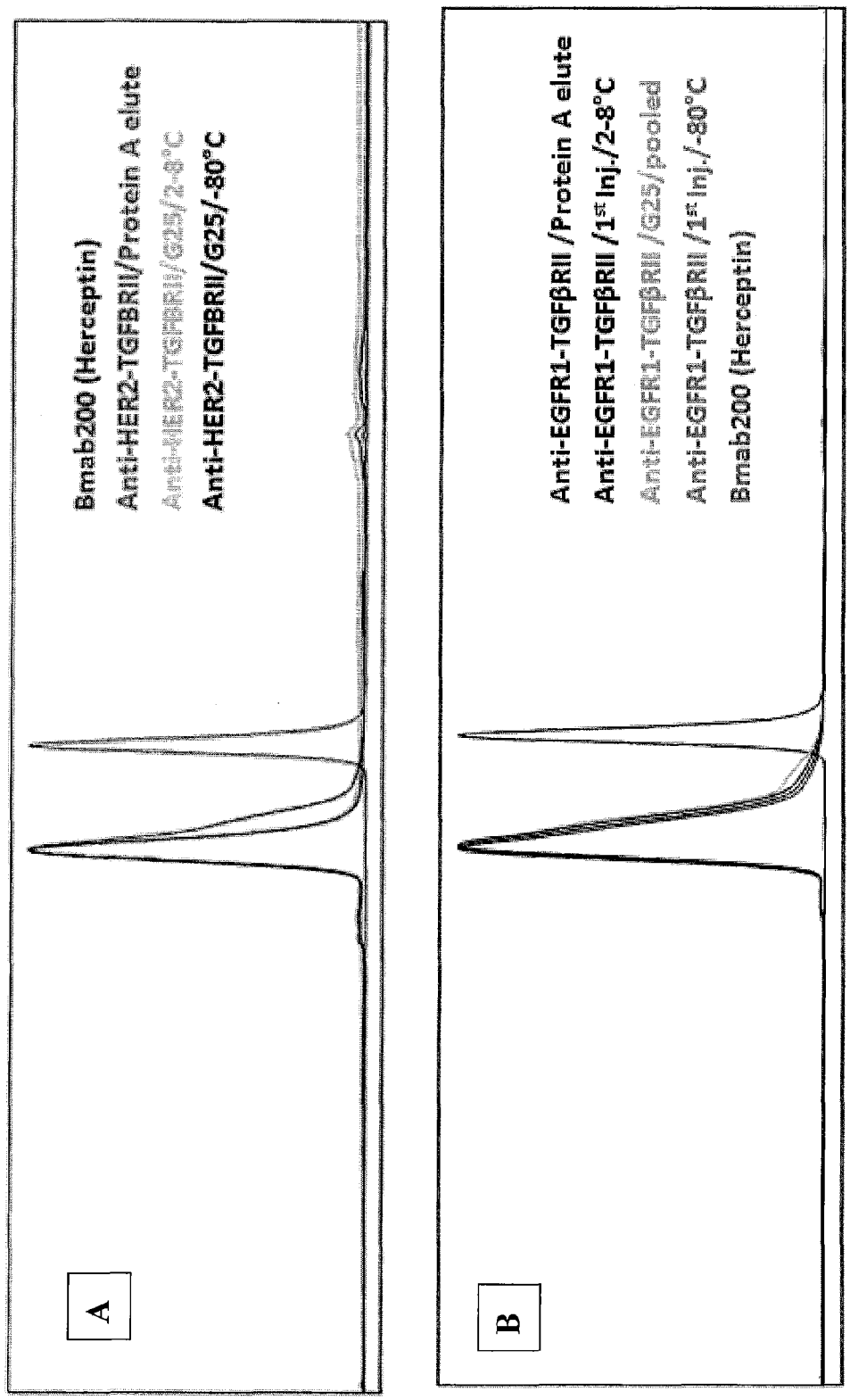

Protein A/SEC chromatography. The Anti-HER2/neu-TGFβRII and Anti-EGFR1-TGFβRII samples were analyzed by ProteinA/SEC chromatography and the results are shown in FIG. 23. FIG. 23 A shows a sharp peak of elution of Bmab200(Herceptin) vs a broader elution peak is believed to be a measure of heterogeneity due to presence of glycosylation as there are three additional N-glycosylation sites that are present in the TGFβRII region. Notably storage at −80 C did not causing aggregation. The shift in the position or appearance of the peak early in SEC column indicates that the increase in the molecular weight is because of the fusion partner. This once again confirms that the full length molecule is being expressed. FIG. 23 B shows a sharp peak of elution of Bmab200(Herceptin) vs a broader elution peak which is believed to be a measure of heterogeneity due to presence of glycosylation sites as there are three additional N-glycosylation sites are present in the TGFβRII region. Again, storage at −80 C did not causing aggregation. The shift in the position or appearance of the peak early in SEC column indicates that the increase in the molecular weight is because of the fusion partner. This once again confirms that the full length molecule is being expressed.

Example 3

Figure 25:
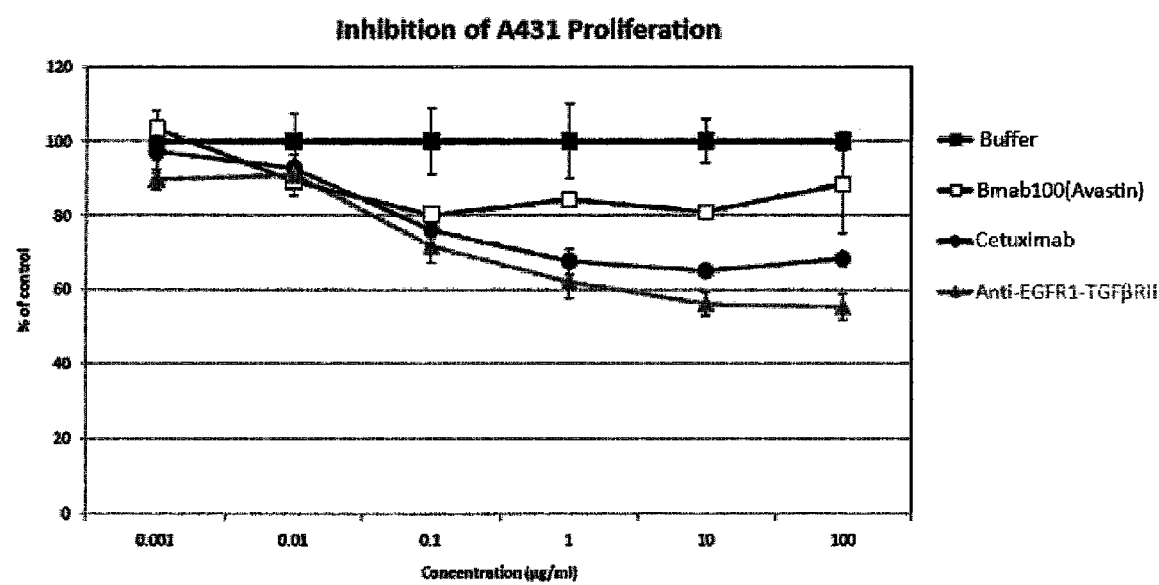
FIG. 25 shows that Anti-EGFR1-TGFβRII-inhibits the proliferation of A431 cell line similar to the Cetuximab.

Functional assays for the Fusion proteins. ELISA experiment was carried out to check the binding ability of Anti-HER2/neu-TGFβRII and Anti-EGFR1-TGFβRII to TGFβ. FIG. 24 A shows that Anti-HER2/neu-TGFβRII and Anti-EGFR1-TGFβRII molecules bind to the TGFβ indicating that the fusion protein is functional. FIG. 24 B shows that Anti-HER2-TGFβRII inhibits the proliferation of BT474 cell line similar to the Bmab200 (Herceptin). FIG. 25 shows that Anti-EGFR1-TGFβRII-inhibits the proliferation of A431 cell line similar to the Cetuximab.

Example 4

Figure 27:
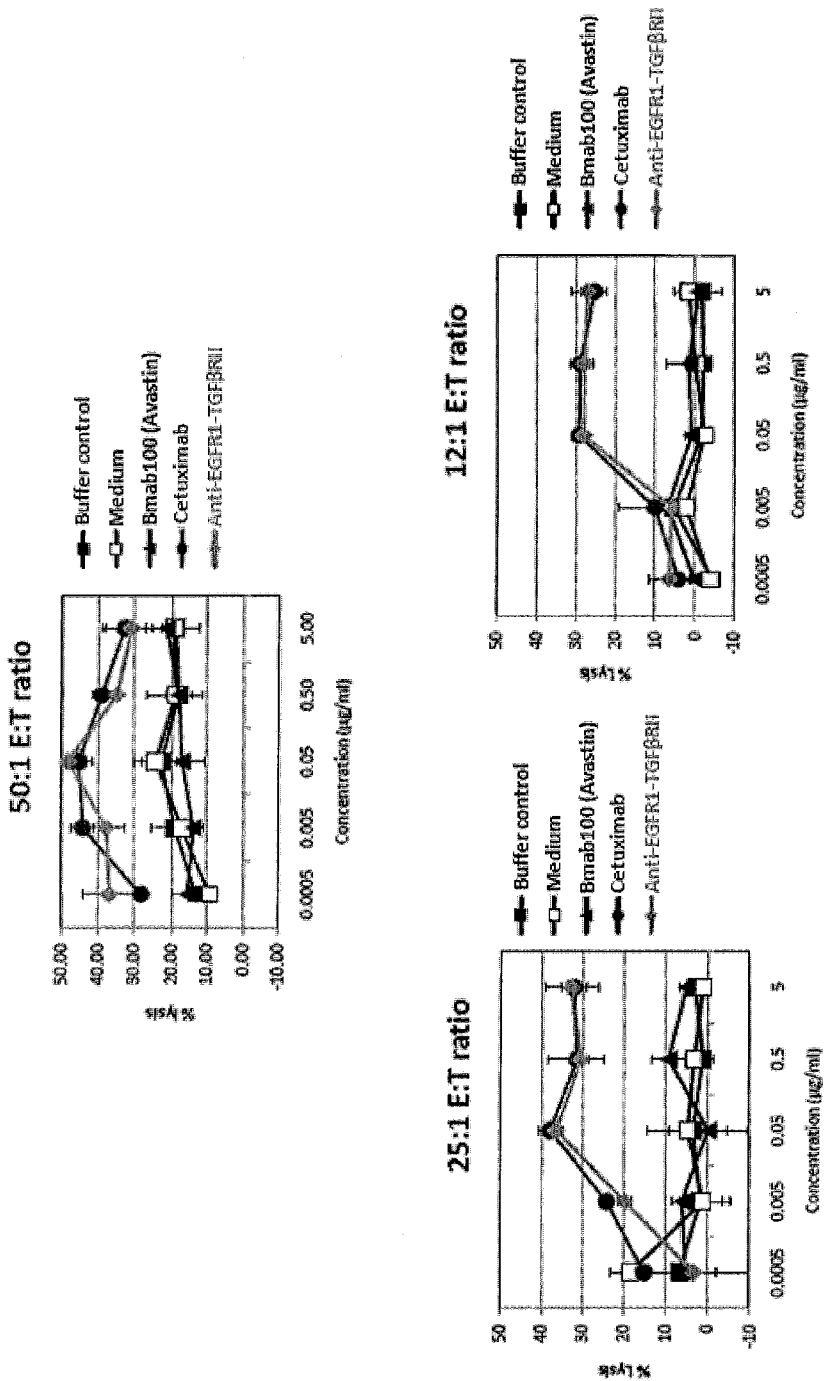
FIG. 27 shows the ADCC activity of Anti-EGFR1-TGFβRII on A431 cells wherein the ADCC activities are similar to that of Cetuximab.
Figure 28:
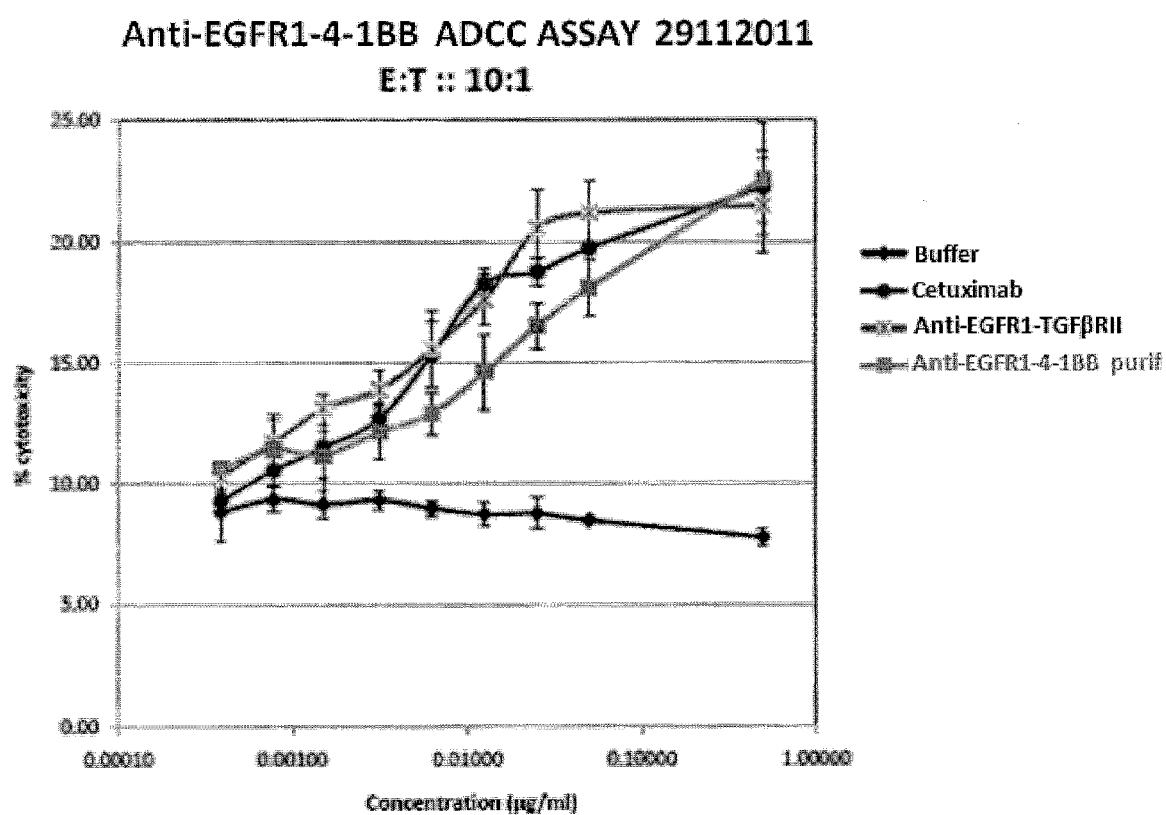
FIG. 28 shows the ADCC activity of ADCC activity of Anti-EGFR1-4-1BB in comparison with Anti-EGFR1-TGFβRII and cetuximab.

Antibody dependent cellular cytotoxicity ADCC activity for Anti-HER2/neu-TGFβRII fusion protein was conducted to determine that the protein binds to the target receptors on the cells. The results are shown in FIG. 26 wherein the activity is determined in BT474 cells and it is evident that ADCC activity (% lysis of cells) of Anti-HER2-TGFβRII on BT474 cells is similar to that of Bmab200(Herceptin). FIG. 27 shows ADCC activity of Anti-EGFR1-TGFβRII on A431 cells wherein the ADCC activities are similar to that of Cetuximab. FIG. 28 shows the ADCC activity of ADCC activity of Anti-EGFR1-4-1BB in comparison with Anti-EGFR1-TGFβRII and cetuximab.

Example 5

Figure 29:
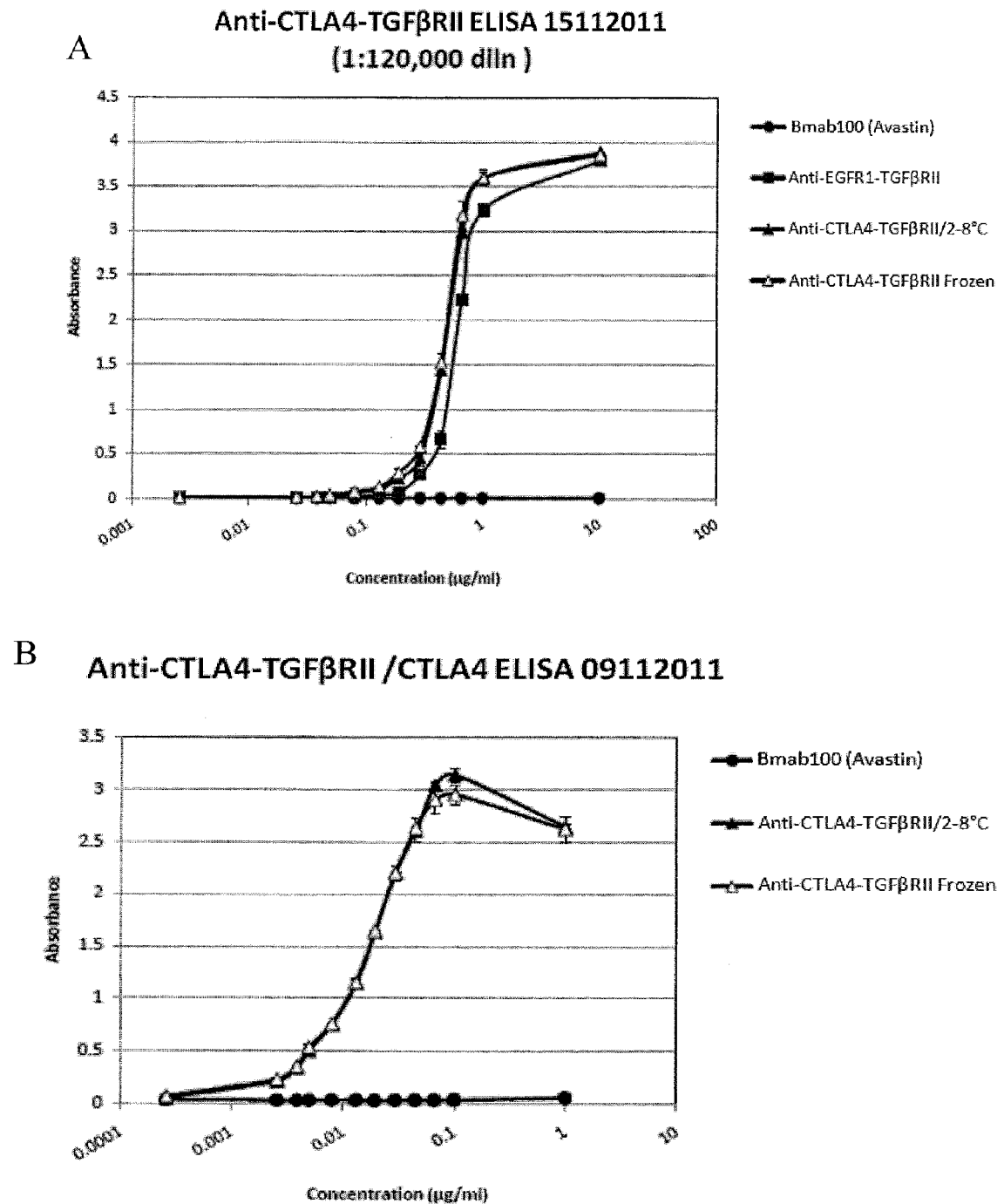
FIG. 29 A shows that the binding activity of Anti-CTLA4-TGFβRII to TGFβ1 is comparable to Anti-EGFR1-TGFβRII and B shows that the binding activity of Anti-CTLA4-TGFβRII to CTLA4.
Figure 32:
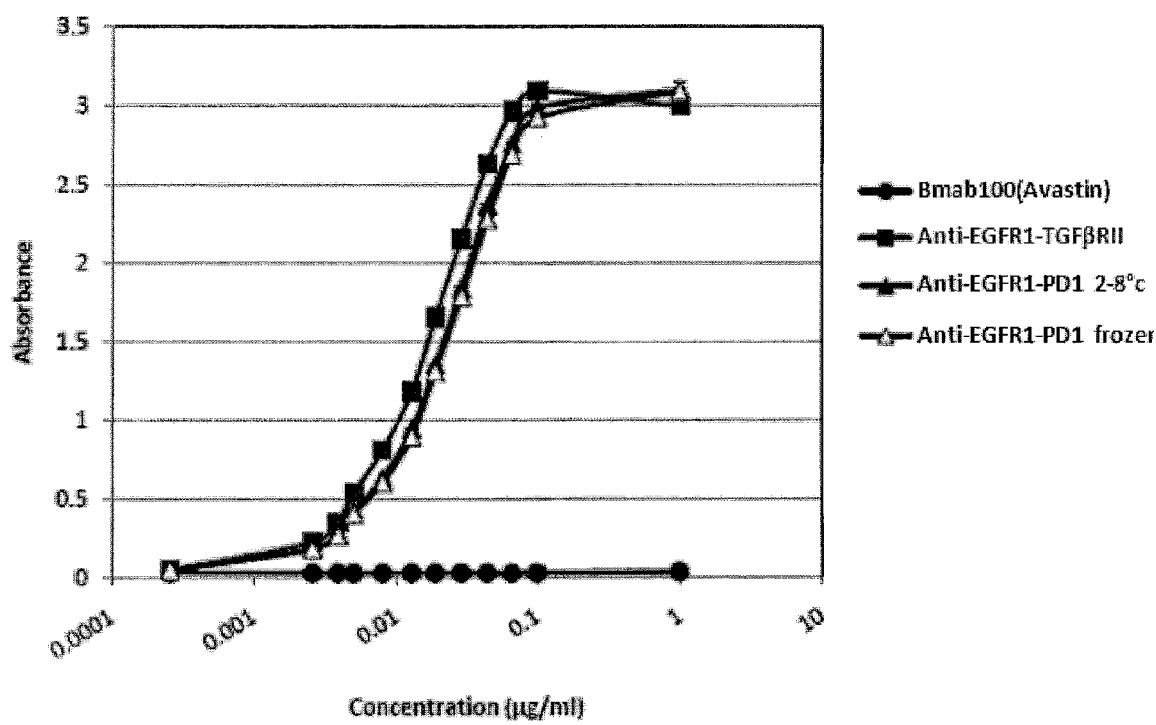
FIG. 32 shows the binding activity of Anti-EGFR1-PD1 to EGFR and PD1.

Binding Activity of the expressed proteins. The aim of this assay is to test the functionality of the fusion proteins to bind to the target receptors on the cells in a dose dependent manner. FIG. 29 A shows that the binding activity of Anti-CTLA4-TGFβRII to TGFβ1 is comparable to Anti-EGFR1-TGFβRII and B shows that the binding activity of Anti-CTLA4-TGFβRII to CTLA4. FIG. 30 A shows the binding activity of Anti-CTLA4-TGFβRII to determine the level of PD1-Fc binding and B shows the binding activity of Anti-EGRF1-4-1BB to determine the binding of 4-1BBL. FIG. 31 A shows the binding activity of Anti-EGFR1-4-1BB to EGFR and B shows the binding activity of PD1-Fc-4-1BB to find out PDL1-Fc. FIG. 32 shows the binding activity of Anti-EGFR1-PD1 to EGFR and PD1.

Example 6

Confirmation of primary structure of molecule. As shown in FIG. 33, the expressed proteins are evaluated to determine the molecular weight and the presence of glycosylation. The samples were analyzed by reducing and non-reducing SDS PAGE. The heavy and light chains of the antibody are separated by reduction alkylation so that the reduced structures can be evaluated. Tryptic digestion of the fusion proteins provides for the identification of the primary sequence. MS/MS analysis of the proteins is performed.

Figure 35:
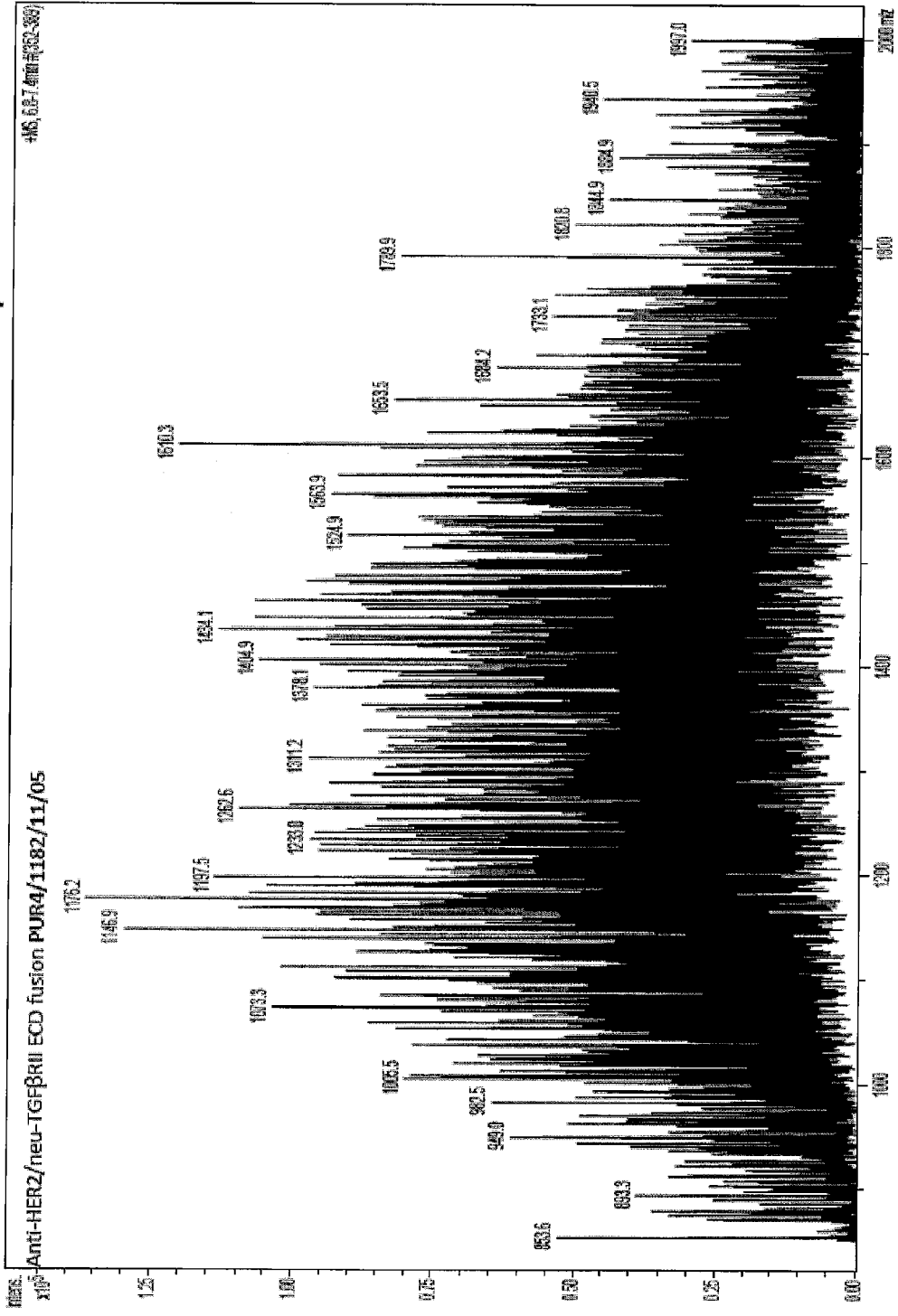
FIG. 35 shows the Mass Spectrum of heavy chain (HC) (Reduced) of Anti-HER2/neu-TGFβRII ECD fusion.

Mass Spectrometry Analysis of Anti-HER2/neu-TGFβRII and Anti-EGFR1-TGFβRII. The fusion protein shown in FIG. 1 was expressed and tested. FIG. 34 A shows the mass spectrum Mass Spectrum of light chain (LC)(Reduced) of Anti-HER2/neu-TGFβRII ECD fusion and B shows Deconvoluted Mass Spectrum of LC (Reduced) of Anti-HER2/neu-TGFβRII ECD fusion. FIG. 35 shows the Mass Spectrum of heavy chain (HC) (Reduced) of Anti-HER2/neu-TGFβRII ECD fusion.

Figure 36:
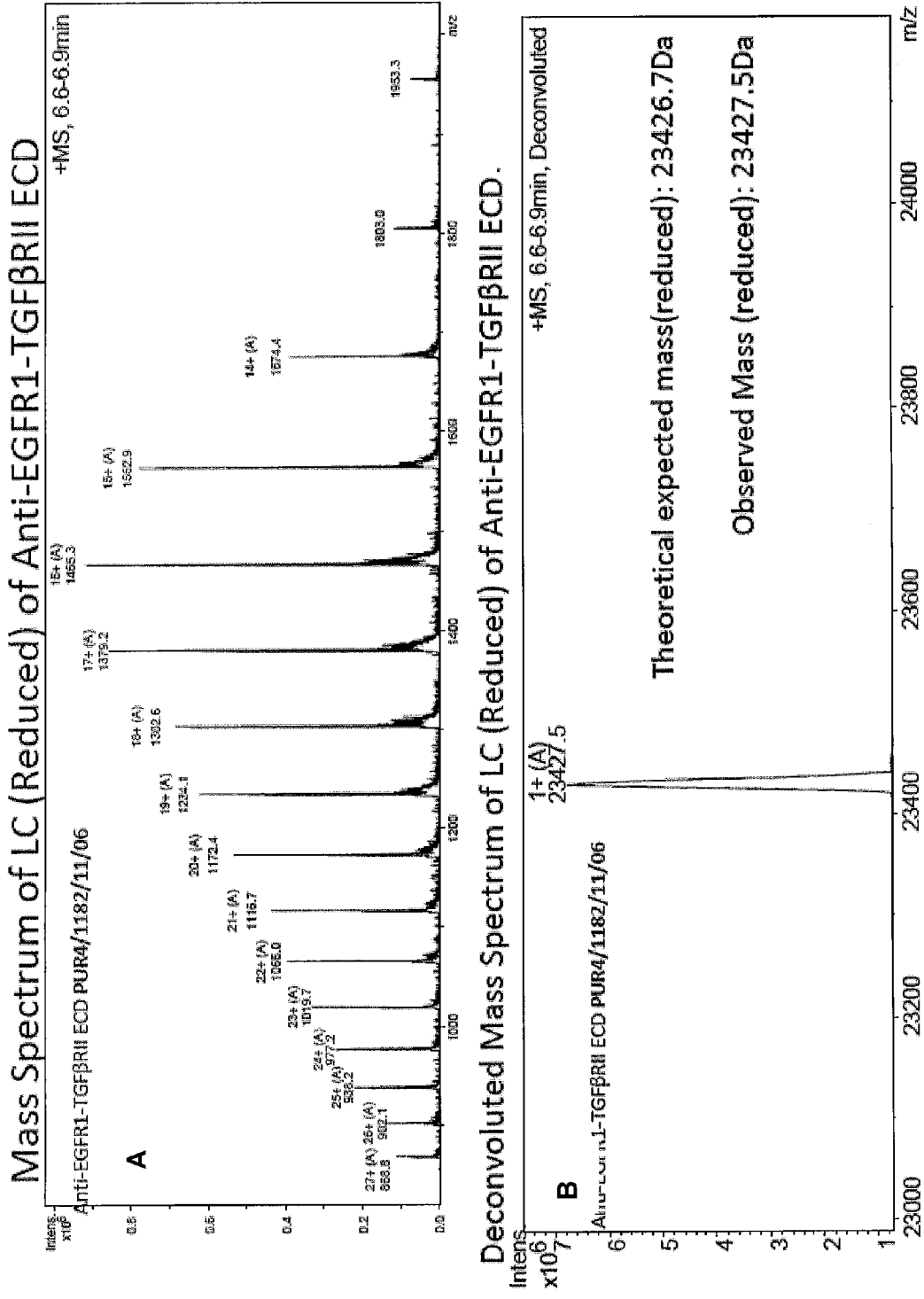
FIG. 36 A shows the Mass Spectrum of LC (Reduced) of Anti-EGFR1-TGFβRII ECD and B shows the Deconvoluted Mass Spectrum of LC (Reduced) of Anti-EGFR1-TGFβRII ECD.
Figure 37:
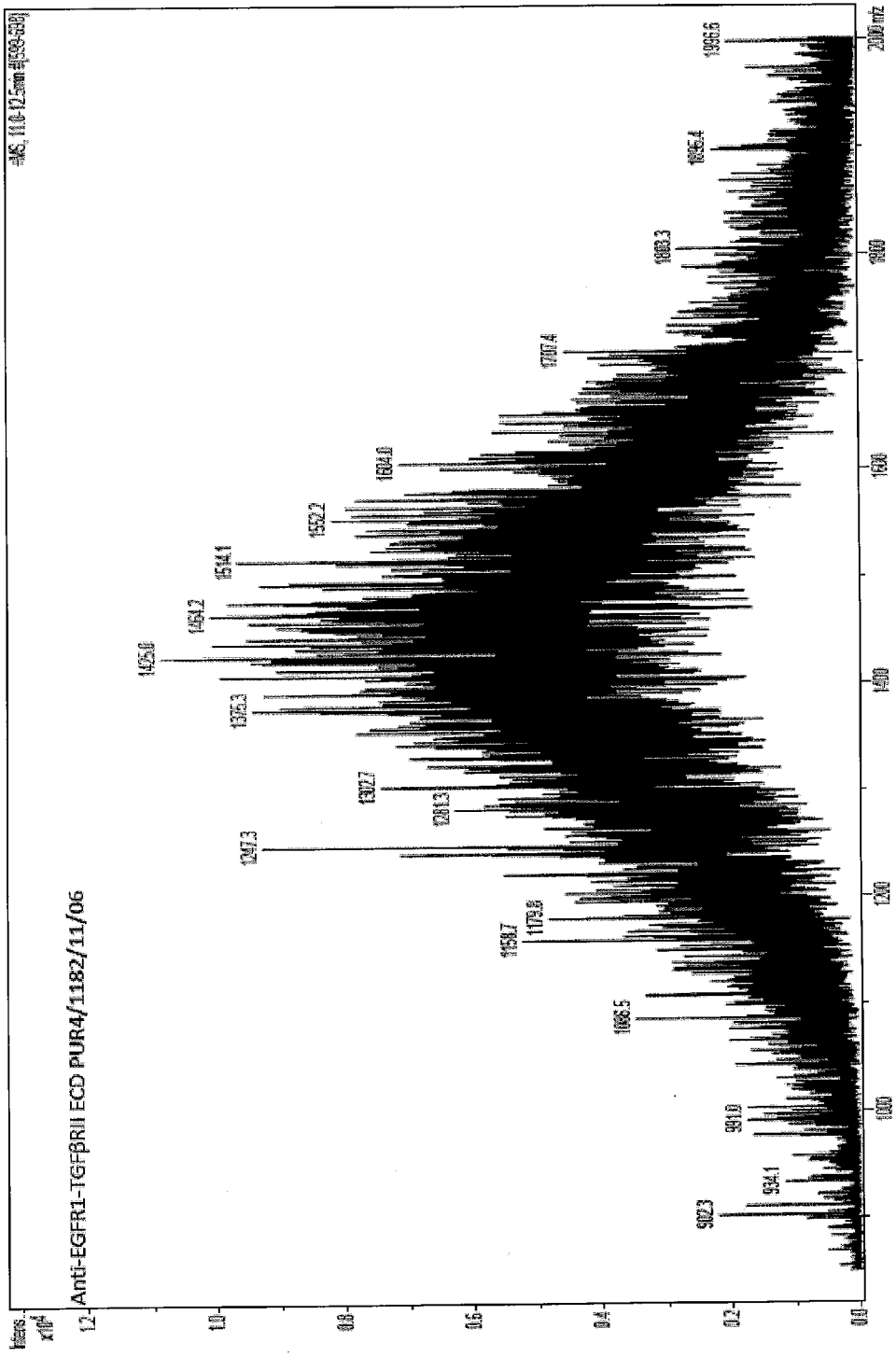
FIG. 37 shows the Mass Spectrum of HC (Reduced) of Anti-EGFR1-TGFβRII ECD.

The fusion protein shown in FIG. 2 was expressed and tested. FIG. 36 A shows the Mass Spectrum of LC (Reduced) of Anti-EGFR1-TGFβRII ECD and B shows the Deconvoluted Mass Spectrum of LC (Reduced) of Anti-EGFR1-TGFβRII ECD. FIG. 37 shows the Mass Spectrum of HC (Reduced) of Anti-EGFR1-TGFβRII ECD.

Example 7

Figure 38:
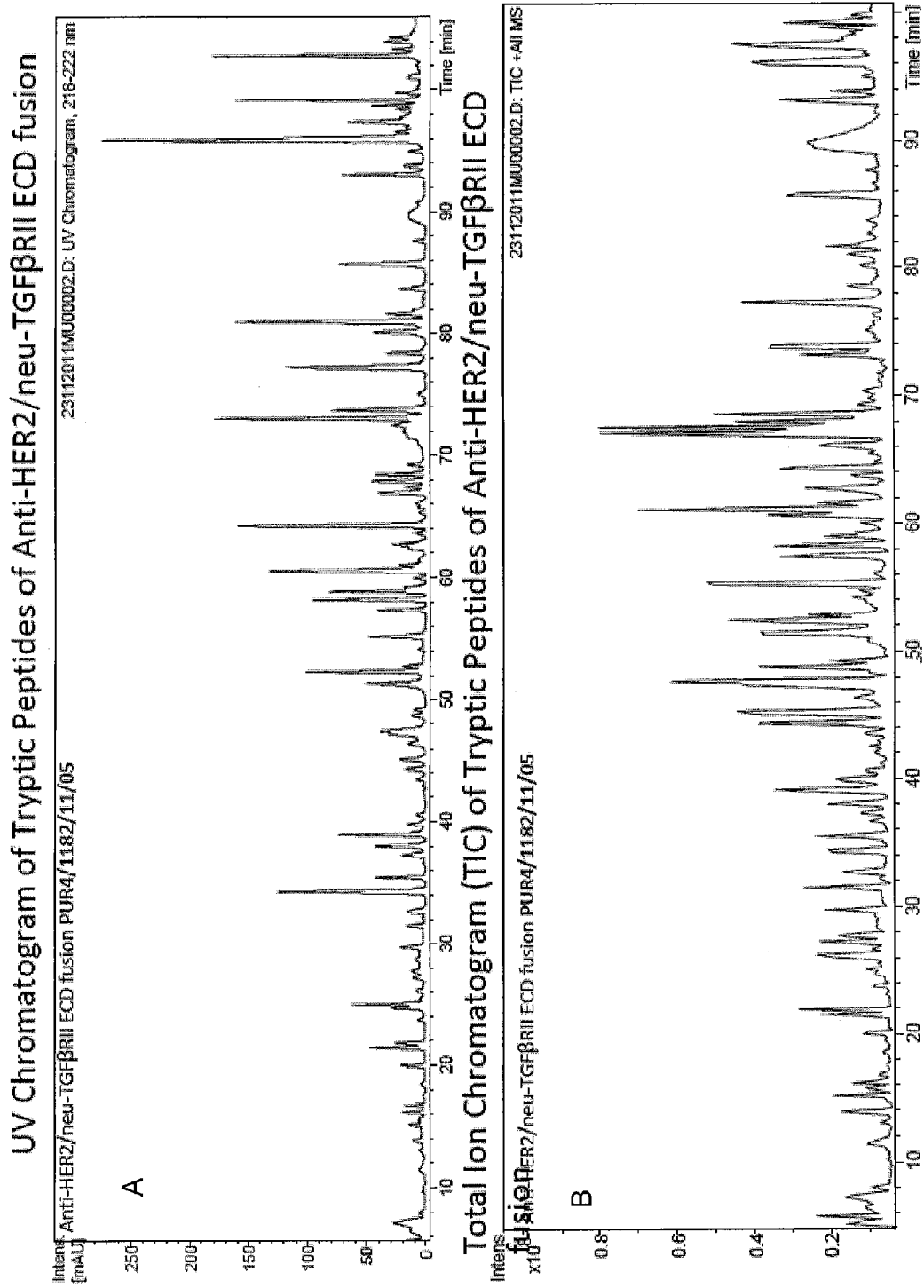
FIG. 38 A shows the UV Chromatogram of Tryptic Peptides of Anti-HER2/neu-TGFβRII ECD fusion protein and B shows the Total Ion Chromatogram (TIC) of Tryptic Peptides of Anti-HER2/neu-TGFβRII ECD fusion protein.
Figure 42:
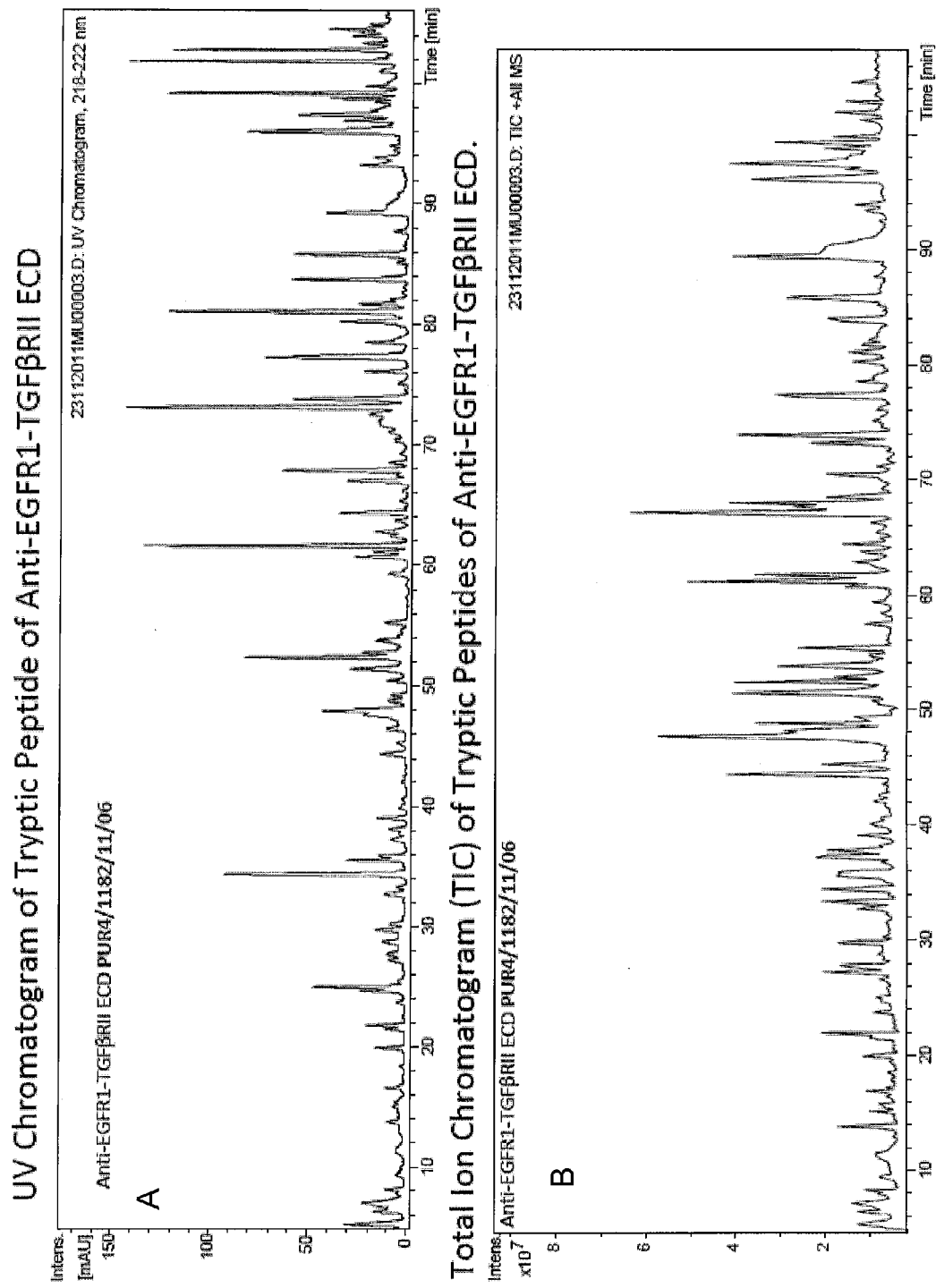
FIG. 42 A shows the UV Chromatogram of Tryptic Peptides of Anti-EGFR1-TGFβRII ECD fusion protein and B shows the Total Ion Chromatogram (TIC) of Tryptic Peptides of Anti-EGFR1-TGFβRII ECD fusion protein.

The fusion proteins having amino acid sequences as described in FIGS. 1 and 2 were inspected using UV chromatography and providing chromatograms resulting from the chromatographic separation of the tryptic digest of the fusion proteins and tested with UV 218-222 nm wavelength. Total Ion Current (TIC) corresponding to UV trace was also evaluated. FIG. 38 A shows the UV Chromatogram of Tryptic Peptides of Anti-HER2/neu-TGFβRII ECD fusion protein and B shows the Total Ion Chromatogram (TIC) of Tryptic Peptides of Anti-HER2/neu-TGFβRII ECD fusion protein. FIGS. 39, 40 and 41 provide lists of expected/observed tryptic peptide of the light chain, heavy chain and linked motif of the Anti-HER2/neu-TGFβRII ECD fusion protein, respectively. Notably, all the expected peptides of the molecules were identified including the light and heavy chain peptides and the peptides of the linked motif (TGF FIG. 42 A shows the UV Chromatogram of Tryptic Peptides of Anti-EGFR1-TGFβRII ECD fusion protein and B shows the Total Ion Chromatogram (TIC) of Tryptic Peptides of Anti-EGFR1-TGFβRII ECD fusion protein. FIGS. 43, 44, and 45 provide lists of expected/observed tryptic peptide of the light chain, heavy chain and linked motif of the Anti-EGFR1-TGFβRII ECD fusion protein, respectively. Again all the expected peptides of the molecules were identified including the light and heavy chain peptides and the peptides of the linked motif (TGF βRII).

Example 8

The host cell line used for the expression of recombinant fusion protein expression is CHO cells or the derivative of the CHO cells. The CHO cells referred here is either freedom CHO-S cells; CHO-S Cells are CHO-derived cells adapted to high density, serum-free suspension culture in chemically-defined medium that are capable of producing high levels of secreted, recombinant protein or CHO K1 cells; having the same as ATCC No. CCL-61. It is basically an adherent cell line. The vectors used for stable cell line:

The Freedom pCHO 1.0 vector, designed by ProBioGen AG, to express one or two genes of interest downstream of the vector's two different hybrid CMV promoters. This vector contains the dihydrofolate reductase (DHFR) selection marker and a puromycin resistance gene, allowing selection using MTX and Puromycin simultaneously.

The light chain or the light chain fusion protein coding nucleic acid sequences are cloned into the restriction enzyme sites AvrII and BstZ17 under the control of EF2/CMV promoter. The heavy chain or the heavy chain fusion protein coding nucleic acid sequences are cloned, in restriction enzyme sites EcoRV and PacI under the control of CMV/EF1 promoter.

The construct(s) are transfected into Freedom CHO-S cells/CHOK1 cells. The high producer single, clonal cell strain is selected for producing the recombinant fusion protein. Prepare the MCB and characterize for cell viability, productivity, stability and other parameters. The cells are used for culturing followed by purification.

Example 9

The cell culture is performed in feed-batch mode. In the cell culture, the mammalian host cells used is Chinese Hamster Ovary (CHO) cells and culture medium are supplied initially. The CHO cells are genetically engineered to produce the Antibody-peptide fusion protein. The zinc sulphate hepta hydrate salt is added in the medium at a concentration of 0.4 mM. In contrast, there is no addition of any zinc salt in the control medium. The production fermentation run starts with an initial cell count of 0.3-0.45×$10^6$ cells/ml at 37±1° C., the first 3-4 days are dedicated to grow the cells in batch phase. Next step involves lowering the temperature to 31±1° C. and continuing the run till 7th day. Lactate reduces by almost 10-40% throughout the run. The produced fusion protein is then collected from the media using the technique of affinity chromatography.

Example 10

The cell culture is performed in a feed-batch mode is employed. In the cell cultures the mammalian host cells and culture medium which is Hyclone CDM4Mab are supplied initially. The salts (zinc) is also added in the medium (0.3 mM). The production fermentation run starts with an initial cell count of $0.3\text{-}0.45 \times 10^6$ cells/nil at $37 \pm 1°$ C., the first 3-4 days are dedicated to growing the cells in batch phase. Next step involves lowering the temperature to $31+1-1°$ C. and continuing the run till 7th day.

Example 11

Purification of antibody-peptide fusion immunostimulatory molecules using protein A column. Supernatant culture secreted from recombinant CHO cell line containing the fusion monoclonal antibodies is tested for titer and endotoxins under sterile conditions. The supernatant is subjected to affinity chromatography using Mab Select Xtra Protein A affinity resin, washed and equilibrated with binding buffer. The pH of the supernatant is adjusted using 0.5M phosphate to the same pH as the column; the supernatant is allowed to bind to the column/pass through the column at the flow rate of 0.5 ml/minute to achieve the maximum binding. All the Antibody-proteins fusion molecules bind through the Fc region while impurities are eliminated as flow through. The column is washed with equilibration buffer and the bound fusion molecules are eluted using 0.1 M glycine at pH 3.0. The pH of the eluted proteins is adjusted to neutral pH or the stable formulation pH and the purified protein are stored at $-20°$ C. or at $2\text{-}8°$ C.

Example 12

Differentiating Trastuzumab from Trastuzumab-TGF βRII Receptor Fusion Molecule A breast cancer tumor overexpressing the ErbB2 receptor will either by constitutive activation or heterodimerization with other members of the ErbB family of receptors lead to tumor progression. This will involve the binding of growth factors associated with the ErbB signaling pathway. In addition to this, the tumor creates a milieu wherein the immune system is suppressed by activating TGF β and specific cytokines involved in the subdued immune response. A novel molecule is generated wherein Trastuzumab (anti ErbB2) is fused with the TGF βRII receptor as a fusion protein. While it is hypothesized that Trastuzumab will act as a targeted molecule homing into the ErbB2 overexpressing breast cancer cells, the TGFβRII receptor will sequester TGFβ leading to immune activation. The experiment will utilize the growth of Herceptin resistant ErbB2 expressing cell lines (selected by growing BT474 cells in the presence of Herceptin) in the presence of TGFβ, cytotoxic CD8 positive cells and NK cells. While Trastuzumab will be ineffective in inducing cytotoxicity Trastuzumab TGFβRII receptor fusion molecule will sequester the TGFβ thereby preventing the inhibition of cytotoxic CD8 and NK cells. This will lead to enhanced cytotoxicity observed in Trastuzumab-TGFβRII receptor fusion treated cells over cells treated with Trastuzumab alone. The readout for the experiment will use Alamar Blue a resazurin dye which will get activated directly proportional to live cells present. Another method could be to measure cytotoxicity by using cytotox glo which measures protease release which directly corresponds to proportional dead cells. Yet another method could be the use of the flow cytometer directly measuring apoptotic and necrotic cell population by using Annexin V and propidium iodide. Results from these multiple experiments will elucidate understanding of the activity of the conjugate molecule as compared to Trastuzumab alone.

Although the invention has been described with reference to the above example, it will be understood that modifications and variations are encompassed within the spirit and scope of the invention. Accordingly, the invention is limited only by the following claims.

---

That which is claimed is:

1. A method of treating cancer by reducing proliferation of cancer cells, the method comprising contacting cancer cells with a therapeutic amount of chimeric fusion protein, wherein the chimeric fusion protein comprises a targeting moiety to target a cancer cell and an immunomodulating moiety that counteracts immune tolerance, wherein the targeting moiety and the immunomodulating moiety are linked by an amino acid spacer of sufficient length of amino acid residues so that both moieties can successfully bind to their individual targets, wherein the immunomodulating moiety is TGFβRII comprising SEQ ID NO: 4, wherein the amino acid spacer is selected from SEQ ID NO: 3 or SEQ ID NO: 11; and wherein the targeting moiety consists of a light chain of an Anti-EGFR1 antibody; wherein SEQ ID NO: 4 is attached via the amino acid spacer to the C-terminus of the light chain SEQ ID NO: 6 of the Anti-EGFR1 antibody.

2. The method of claim 1, further comprising administering the chimeric fusion protein in combination with another existing cancer treatment.

3. The method of claim 1, wherein the amount of TGF-β in a cancerous tumor of the subject is reduced.

4. The method of claim 1, wherein suppression of an immune system of the subject in the cancer cell is reduced.

5. The method of claim 1, wherein cytotoxic lymphocytes and Natural Killer cells are activated in the subject.

6. The method of claim 1, wherein lysis of cancer cells is increased.

* * * * *